United States Patent
Knowland et al.

(10) Patent No.: US 9,939,533 B2
(45) Date of Patent: *Apr. 10, 2018

(54) SYSTEM AND METHOD FOR THE DETECTION OF GAMMA RADIATION FROM A RADIOACTIVE ANALYTE

(71) Applicant: Lucerno Dynamics, LLC, Cary, NC (US)

(72) Inventors: Joshua G. Knowland, Cary, NC (US); Charles W. Scarantino, Raleigh, NC (US); Ronald K. Lattanze, Morrisville, NC (US)

(73) Assignee: Lucerno Dynamics, LLC, Cary, NC (US)

( * ) Notice: Subject to any disclaimer, the term of this patent is extended or adjusted under 35 U.S.C. 154(b) by 544 days.

This patent is subject to a terminal disclaimer.

(21) Appl. No.: 14/678,550

(22) Filed: Apr. 3, 2015

(65) Prior Publication Data

US 2015/0276937 A1 Oct. 1, 2015
US 2016/0238716 A9 Aug. 18, 2016

Related U.S. Application Data

(63) Continuation-in-part of application No. 13/840,925, filed on Mar. 15, 2013, now Pat. No. 9,002,438.

(Continued)

(51) Int. Cl.
*A61B 6/00* (2006.01)
*G01T 1/161* (2006.01)
*G01T 1/164* (2006.01)

(52) U.S. Cl.
CPC ............ *G01T 1/161* (2013.01); *A61B 6/4258* (2013.01); *A61B 6/463* (2013.01); *G01T 1/1612* (2013.01); *G01T 1/1648* (2013.01); *A61B 6/467* (2013.01)

(58) Field of Classification Search
CPC ...... G01T 1/161; G01T 1/1648; G01T 1/1612; A61B 6/463; A61B 6/4258; A61B 6/467

(Continued)

(56) References Cited

U.S. PATENT DOCUMENTS 4,629,894 A   12/1986 LeLong
4,692,890 A   9/1987 Arseneau (Continued)

FOREIGN PATENT DOCUMENTS

JP        2002196080 A    7/2002
WO    WO 2007140352 A2   12/2007

(Continued)

OTHER PUBLICATIONS

S.D. Wollenweber, R.D. Hichwa, and L.L.B. Ponto, "A Simple On-Line Arterial Time-Activity Curve Detector for [O-15] Water PET Studies", IEEE Transactions on Nuclear Science, vol. 44, No. 4, pp. 1613-1617, Aug. 1997.

(Continued)

Primary Examiner — Sanjay Cattungal
(74) Attorney, Agent, or Firm — Williams Mullen; Andrew R. Shores

(57) ABSTRACT

A system and method for the measurement of radiation emitted from an in-vivo administered radioactive analyte. Gamma radiation sensors may be used to determine the proper or improper administration of a radioactive analyte in some cases, the system employs a sensor having a scintillation material to convert gamma radiation to visible light, which enables embodiments of the sensor to be ex vivo. A light detector converts the visible light to an electrical signal. This signal is amplified and is processed to measure the captured radiation. Temperature of the sensor may be recorded along with this radiation measurement for temperature compensation of ex vivo embodiments. The sensor (Continued)

enables collection of sufficient data to support separate application to predictive models, background comparisons, or change analysis.

22 Claims, 62 Drawing Sheets

Related U.S. Application Data

(60) Provisional application No. 61/653,014, filed on May 30, 2012.

(58) Field of Classification Search
USPC .......................................................... 600/436
See application file for complete search history.

(56) References Cited

U.S. PATENT DOCUMENTS

| | | | |
|---|---|---|---|
| 4,881,171 | A | 11/1989 | Jatteau et al. |
| 5,007,427 | A | 4/1991 | Suzuki et al. |
| 5,309,357 | A | 5/1994 | Stark et al. |
| 5,428,223 | A | 6/1995 | Jatteau et al. |
| 5,583,343 | A | 12/1996 | Avraham |
| 5,647,363 | A | 7/1997 | Rabito et al. |
| 5,821,538 | A | 10/1998 | DeAntoni et al. |
| 6,668,544 | B1 | 12/2003 | Baerts |
| 8,680,476 | B2 | 3/2014 | Webster et al. |
| 2002/0137991 | A1 | 9/2002 | Scarantino et al. |
| 2003/0012731 | A1 | 1/2003 | Suddarth et al. |
| 2003/0189657 | A1 | 10/2003 | Hammadou |
| 2005/0143927 | A1 | 6/2005 | Cammia et al. |
| 2005/0287065 | A1 | 12/2005 | Suddarth et al. |
| 2006/0076523 | A1 | 4/2006 | Higashiisogawa et al. |
| 2009/0150315 | A1 | 6/2009 | Wirtz et al. |
| 2009/0226915 | A1 | 9/2009 | Guyon |
| 2009/0250602 | A1 | 10/2009 | Black et al. |
| 2009/0266993 | A1 | 10/2009 | Baerwolff Hartmut et al. |
| 2010/0010343 | A1 | 1/2010 | Daghighian et al. |
| 2010/0198061 | A9 | 8/2010 | Daghighian et al. |
| 2010/0268078 | A1 | 10/2010 | Scarantino et al. |
| 2011/0196234 | A1 | 8/2011 | Buono et al. |
| 2011/0301863 | A1 | 12/2011 | Auribault et al. |
| 2014/0018675 | A1 | 1/2014 | Keppel et al. |

FOREIGN PATENT DOCUMENTS

| | | |
|---|---|---|
| WO | WO 2009158143 A1 | 12/2009 |
| WO | WO 2010 039298 | 1/2010 |

OTHER PUBLICATIONS

Extended European Search Report dated Nov. 11, 2016.
Son, C., An implantable Wireless Microdosirmeter for Radiation Oncology, School of Electrical and Computer Engineering, Mems 2008, Jan. 13-17, 2008, pp. 256-259.
Bashak, Abishek, Low-Power Implantable Ultrasound Imager for Online Monitoring of Tumor Growth, 33rd Annual Intl Conference of the IEEE EMBS, Boston, MA., . . . Aug. 30-Sep. 3, 2011, pp. 2858-2861.
Weber, A. Wolfgang, Use of PET for monitoring Cancer Therapy and for Predicting Outcome, The Journal of Nuclear Medicine, vol. 46, No. 6, Jun. 2005 pp. 983-995.
Delbeke, Dominique, Procedure Guideline for Tumor Imaging with 18F-FDG PET/CT 1.0, The Journal of Nuclear Medicine, vol. 47, No. 5, May 2006, pp. 885-895.
Dunwald Lisa, PET Tumor Metabolism in locally advanced breast cancer patients undergoing neoadjuvant chemotherapy: Value of static versus kinetic measures of . . . flurodeoxyglucose uptake, Clinical Cancer Research, vol. 17, No. 8, Apr. 15, 2011, pp. 24700-2409.
Valasqquez, Linda M., Repeatability of 18F-FDG PET in a multi-center Phase I study of patients with advanced gastrointestinal malignancies, The Journal of Nuclear Medicine . . . vol. 50, No. 10, Oct. 2009, pp. 1646-1654.
International Search Report dated Feb. 19, 2004.
Osman, Medhat M. FDG dose extravasatins in PET/CT: frequency and impact on SUV measurements, Front. Oncol, Nov. 16, 2011 . . . http://journal.frontiersin.org/article/10.3389/fonc.2011.0004/full.
Office Action dated Aug. 15, 2014.

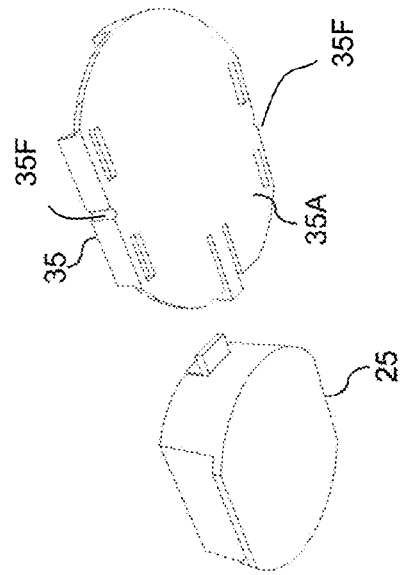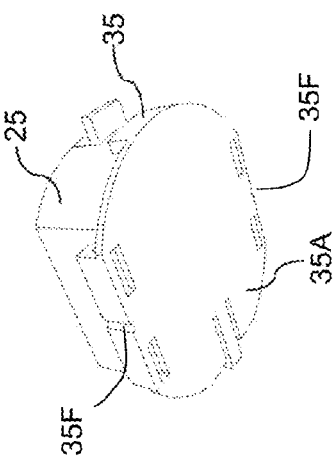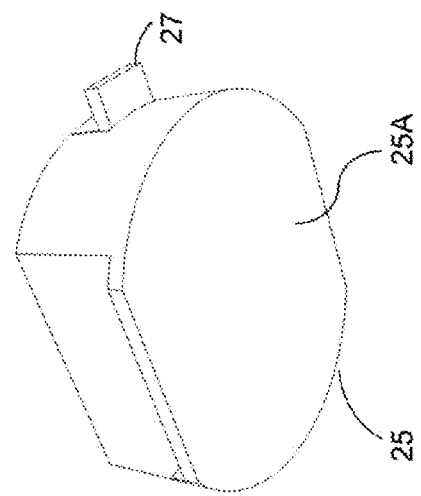
FIG. 4B
FIG. 4C
FIG. 4A

SYSTEM AND METHOD FOR THE DETECTION OF GAMMA RADIATION FROM A RADIOACTIVE ANALYTE

RELATED APPLICATIONS

The present application is a continuation-in-part of U.S. application Ser. No. 13/840,925 filed on Mar. 15, 2013, which claims the benefit of priority to U.S. Provisional Application No. 61/653,014, filed on May 30, 2012, both of which are hereby incorporated in their entirety.

STATEMENT REGARDING GOVERNMENT SUPPORT

None.

FIELD OF THE INVENTION

The present invention relates to measurement and prediction of biological processes, and more particularly to a system and method for using localized radio-labeled tracer temporal uptake to measure and predict biological processes, and ensuring the proper injection or administration of radio-labeled tracer.

BACKGROUND

Oncologists are interested in knowing if the prescribed cancer therapy is having the intended effect, in order to improve outcomes, minimize side effects, and avoid unnecessary expenses. Cytotoxic treatments kill tumor cells. Cytostatic treatments inhibit cell growth leaving tumors the same size, but preventing the spread of the disease, Cytostatic treatments inhibit cell growth leaving tumors the same size, but preventing the spread of the disease. Immunotherapy treatments use the body's immune system to attack the cancer and initially result in an inflammatory response in the tumor area before there is evidence that the body is effectively attacking the tumor. Historically, measuring the tumor has been the primary way for oncologists to assess treatment effectiveness; however, we now understand that the size of the tumor is often not the best or earliest indicator of the therapy effectiveness. With cytotoxic treatment the tumor size reduction only occurs after cancer cells die and the body's natural processes eliminate dead cells; this process can often take weeks. With cytostatic treatment, cancer cells stop growing leaving the clinician unsure of the state of the underlying cancer. With immunotherapy, the body's inflammatory response often masks the tumor from proper evaluation.

The tools available to oncologists and researchers today to assess tumor response to treatments are not ideal. Palpating the tumor is easy and inexpensive, but it is limited to tumors close to the surface, relies on a physician's memory and notes, and primarily measures size. The lack of reproducibility of this palpating process, coupled with historical reasons, contributed to the initial acceptance of significant changes in tumor size as an indicator of therapy assessment. Wolfgang A. Weber, et al., "Use of PET for Monitoring Cancer Therapy and for Predicting Outcome," 46 J. Nucl. Med. (No. 6) 983.995 (June 2005). Imaging tools (CT, MRI, x-ray) provide more precise measurements for tumors both close to the surface and in deep tissue, but again primarily measure size, not the ideal indicator. Molecular imaging (PET/CT scan) captures the positron emissions from injected radio-labeled tracers captured by live cancer cells and is routinely used for pre-therapy staging of cancer. Visually identifying metastatic disease is the primary means of staging cancer; however, a semi-quantitative PET/CT measurement known as Standardized Uptake Value (SUV) is also being used to stage cancer. For example, SUVs are used to help determine whether or not lung nodules are malignant. SUVs are basically a ratio of the amount of radio-labeled tracer in an area of interest (tumor) compared to the level in the rest of the body. While molecular imaging is a primary tool for the pre-therapy need to stage a patient's cancer, it is also rapidly becoming the most advanced tool for oncologists and researchers to assess tumor response, since molecular imaging can capture the metabolic or proliferative condition of the cancer and the size of the tumor. Using an SUV taken from the PET images acquired approximately 60-minutes after injection or administration of a radio-labeled tracer in the staging scans and then comparing this value to an SUV from a follow-up PET/CT is currently the best available indicator for therapy effectiveness.

Despite the increasing trend to use comparative PET/CT scans in assessing tumor response in more and more cancer types as clinical evidence continues to grow, there are still limitations with this state of the art assessment tool. PET/CT scans are expensive and their use is often challenged. Additionally, there are several issues with SUV calculations. According to Dr. Dominique Delbeke: "[t]be reproducibility of SUV measurements depends on the reproducibility of clinical protocols, for example, dose infiltration, time of imaging after 18F-FDG administration, type of reconstruction algorithms, type of attenuation maps, size of the region of interest, changes in uptake by organs other than the tumor, and methods of analysis (e.g., maximum and mean)." Dominique Delbeke, et al., "Procedure Guideline for Tumor Imaging with 18F-FDG PET/CT 1.0," 47 J. Nucl. Med. (No. 5) 885-895 (May 2006). Infiltrated injection (extravasation) of radio-labeled tracer is a complication that often goes unnoticed by clinicians. Medhat Osman, "FDG Dose Extravasations in PET/CT: Frequency and Impact on SUV Measurements," Frontiers in Oncology (Vol. 1:41) 1 (2011). An infiltration is a common problem that can occur when the radio labeled tracer infuses the tissue near the venipuncture site, and can result from the tip of the catheter slipping out of the vein or passing through the vein. Additionally, the blood vessel wall can allow part of the tracer to infuse the surrounding tissue. As a result, the radio-labeled dose being delivered is inaccurate and thus so are the SUV calculations, which can severely impact patient treatment and research conclusions. These infiltrations may in fact contribute to the wide variability in researcher's efforts to characterize SUV thresholds for clinical decision making. In one study, it was determined that the "thresholds for metabolic response in the multicenter multiobserver non-QA settings were −34% and 52% and in the range of −26% to 39% with centralized QA". Linda M. Velasquez, et al., "Repeatability of 18F-FDG PET in a Multicenter Phase I Study of Patients with Advanced Gastrointestinal Malignancies," 50 J. Nucl. Med. (No. 10) 1646-1654 (October 2009). In local practices and even in practices and research centers employing Quality Assurance checks, these issues with SUV calculations have left oncologists and researchers needing to see significant changes in SUV values to be somewhat assured they are making sound treatment decisions or reaching proper research conclusions.

While using SUVs comparisons from PET/CT static images are currently the most advanced way in clinical practices to assess tumor response to treatment, the use of dynamic images (PET images taken at various times during the uptake of the radio-labeled tracers) has provided researchers with kinetic information regarding the uptake of radio-labeled tracers. In the academic community, this kinetic information is proving to be an even better method of assessing treatment and predicting patient outcomes than using static SUVs. (See Lisa K. Dunnwald, "PET Tumor Metabolism in Locally Advanced Breast Cancer Patients Undergoing Neoadjuvant Chemotherapy: Value of Static versus Kinetic Measures of Fluorodeoxyglucose Uptake," Clin. Cancer Res. 2011;17:2400-2409 (published online first Mar. 1, 2011)). Unfortunately, this dynamic PET approach takes approximately three times as long as a static PET/CT scan and thus would require several more PET scanners at each hospital; it is clinically and economically impractical for widespread adoption and clinical use. So while there have been great improvements in the past few decades regarding cancer treatment options, today's oncologists and researchers continue to lack a timely, cost-effective, and fast way to evaluate the effectiveness of the treatments they deliver or the research they are conducting.

In light of the problems associated with current tumor measurement and prediction systems, it is an object of the present invention to provide a way to identify improperly administered radio-labeled tracer injections (infiltrations or extravasation), which negatively impact tumor uptake and PET results, and an easier, less costly, and more efficient system and method for measuring and predicting the status and/or changes in biological processes.

SUMMARY

Disclosed are systems for identifying improperly administered radio-labeled tracer injections and for measuring radio-labeled tracer uptake into a biological system in an easy, quick and relatively inexpensive manner along with requiring less radio-labeled tracer and inflicting less discomfort on the patient. The system can also be used to measure biological processes in laboratory animals with higher through put and less expense than can be accomplished today. Physicians and researchers are better able to make proper treatment and research decisions in a cost effective and efficient manner. Although embodiments of the system of the present invention described below relate to quality control checks for identifying improperly administered radio-labeled tracer injections and measuring and predicting changes in a tumor, for example, embodiments of the system of the present invention can be used to measure processes in nearly any biological system. For example, the system can be used for non-tumor brain scans, assessing inflammation, evaluating kidney function, etc.

Any number of embodiments of the present invention provide a hardware and software system which provides an indication of success in the administration of radio-labeled tracer injections and is used to gather real-time measurements of radio-labeled tracer uptake in a biological process, for example a tumor. Sensors measure the localized uptake of a radio-labeled tracer which is injected into the patient or subject. In an embodiment, for example, sensors can be placed in the following locations: (a) directly over the tumor; (b) on the upper right arm, approximately 10 cm above the antecubital fossa; (c) on the upper left arm, approximately 10 cm above the antecubital fossa; and (d) over another area of interest. By placing a sensor on the upper arm, above the injection site of the radiotracer, the device can assess whether or not a relatively common complication in radiotracer injection has occurred. Properly administered injections of radio-labeled radiotracers pass underneath the injection arm sensor within several seconds of the injection; infiltrations or extravasations remain in the arm tissue outside the vascular system and are detected by the arm sensor.

In any number of embodiments, measurements taken at the sensors can be performed quickly and repeated often. The system of the present invention reduces the amount of expensive radioactive tracer necessary for accurate measurement readings verse the amount required for other measurement methods and eliminates the necessity of using a large PET scanner or similar piece of equipment for follow-up scans (PET/CT scanners may continue to be used to stage diagnosed cancers and to check the subject for metastasis). Measurements made by the present approach reveal the kinetics of the tumor, Biological differences in tumors cause different amounts of radioactive analyte to be consumed locally as compared to normal tissue. The present invention senses and quantifies this consumption, then processes the data into an easy-to-read graph for the oncologist within minutes. Comparing graphs over time—baseline versus subsequent scans—shows the changes in tumor parameters. Changes in biological parameters within the tumor can give the physician insight into whether treatment is working or not. Additionally, the present invention can use predictive algorithms to predict likely changes in biological parameters based on one measurement scan, which speeds the time required to know the likely effectiveness of treatment.

In any number of embodiments, the system can comprise: (i) one or more Measurement Sensors; (ii) a Measurement Control Device; (iii) Computer Software capable of executing measurement and prediction data; and (iv) Database Server Control Software.

In one embodiment, a Measurement Sensor can be a device comprising a scintillation material; a light detector; and an embedded processor with associated embedded software, memory, logic and other circuitry on a printed circuit board. In an embodiment, for example, the sensor's electronics are enclosed in a light-proof enclosure and there can be a multi-conductor cable to enable data communications. Mechanical design of the housing can be used to accurately control the placement of the scintillation material.

In one embodiment, a measurement control device can be, for example, a device comprising a display screen, a keypad and data communications connectors. The control device can further comprise an embedded processor with associated embedded software, memory, a real-time clock, and other associated logic and circuitry on a printed circuit board. In an embodiment, there can be multiple data communications connectors to enable the attachment of multiple measurement sensors. Another embodiment of the control device also includes a data communications connector to enable connection to a computer.

In any number of embodiments, the specialized computer software used in the system of the present invention is capable of: (1) performing diagnostic tests on the measurement control device; (2) transferring measurement data from the measurement control device and saving it to a record file; (3) gathering ancillary test data from the user or other sources (radiation dose administered, patient weight, patient blood-glucose readings, PET scan data, etc.) and including it in the data record file; and (4) transferring the data record file to the database server control software.

In any number of embodiments, the database server control software can be capable of accepting incoming data record files from the computer software and applying one or more Algorithms to the data received. Simple algorithms include, but are not limited to smoothing and/or noise reduction, radioactive decay correction, amplitude correction based on control signals, etc. More complex algorithms can be machine learning algorithms such as Classification Decision Trees, Rule Learning, Inductive Logic, Bayesian Networks, etc. Measurement data can be stored in a central database while the Algorithm output can be used to generate reports for the user. These reports can indicate estimated parameters or even estimated future parameters of a tumor or other biological process.

Some system embodiments may be directed to the ex vivo real-time detection of gamma radiation emitted by a subject from administration and uptake over a period of time of a radioactive analyte that decays in vivo by positron emission. These systems may include at least one ex vivo measurement sensor, at least one computer processor having a non-transient memory and a clock, the computer processor in operable communication with the measurement sensor, a temperature compensator, and computer program code, An ex vivo measurement sensor may have a sensor housing, a scintillation material, a light detector, a temperature sensor, a signal amplifier, and a sensor power source. The light detector, temperature sensor, signal amplifier, and sensor power source may generally be in operable communication. The scintillation material and light detector may be disposed within the sensor housing in a light proof manner, with the scintillation material adapted to receive a level of gamma radiation over the period of time from the in vivo radioactive analyte and to emit photons representative of the gamma radiation level. The light detector may be disposed with respect to the scintillation material so as to receive and convert the photons into signal data representative of the frequency level over time of gamma radiation received. The signal amplifier may be adapted to amplify the signal data, the measurement sensor having at least one sensor output for such amplified signal data.

The at least one computer processor may include a non-transient memory and a clock, with the computer processor being in operable communication with the measurement sensor. The memory may have control computer program code executable by the at least one computer processor. The control computer program code may include a number of software modules, such as a first module for measurement, a second module for data management (with "module" intended to simply mean portion of software program code directed to the function).

A temperature compensator may be coupled with the temperature sensor, such that the temperature sensor is adapted to measure an ambient temperature. The system may thus communicate the ambient temperature to the temperature compensator, so that the temperature compensator generates a temperature correction factor based on comparison of the ambient temperature to a reference temperature. The temperature compensator may be further adapted to apply the temperature correction factor to the signal data to produce temperature compensated signal data.

The first module may be adapted to receive the signal data in a record file format, and the second module may be adapted to receive the signal data of a record file from the first module and to transmit the compensated signal data to a desired storage. The computer program code may further include a third module adapted to receive stored data of a record file from the second module, and to apply such stored data to calculate changes in the compensated signal data over a desired period. This module may also apply stored data to a predictive model to generate predictive data values over a desired period for such record file as a predictive outcome, and to transmit such changes to a desired storage.

Optionally, the ex vivo measurement sensor may include a radiation shielding mask for gamma radiation. The shielding mask may define an aperture in the form of a collimator for gamma radiation incident into the scintillation material. An alignment feature or device may be included for removable alignment of the measurement sensor with respect to the subject, in some cases, the alignment feature may include a light emitter disposed within the sensor so as permit alignment of the collimator aperture to a desired portion of the subject by illumination of the subject. Optionally, the light emitter may be a light emitting diode (LED) disposed within the aperture, and optionally the ex vivo measurement sensor may further include light proof sealant about the LED to prevent the light from the output of the diode for ambient light) to strike the scintillation material, while permitting the scintillation material to receive incident gamma radiation.

Optionally, the ex vivo measurement sensor may further include a radiation shielding mask for gamma radiation, with the shielding mask defining an aperture in the form of a collimator for gamma radiation incident into the scintillation material; and the system further may include a stand alignment device or feature for the removable mounting of the ex vivo measurement sensor in a configuration relative to the subject so as to permit alignment of the collimator aperture to a desired portion of the subject.

Optionally, the third module may detect infiltration conditions, in one approach, the third module may calculate changes in the compensated signal data in order to determine infiltration of radioactive analyte, in another approach, the predictive model may include data representative of radiation frequency over time associated with infiltration of the analyte within the subject for determining an infiltration. Such a predictive model may include data representative of spike of radiation frequency over time associated with administration of the analyte for determining proper administration of the analyte. An alarm or indicator may be included to announce the determination of infiltration. Also optionally, some embodiments may include an arm-band for removable affixation of the ex vivo measurement sensor to an arm of the subject.

Optionally, a noise reduction filter may be included for filtering the amplified signal data based on amplitude or pulse height. Such a filter may be implemented with a voltage comparator. Alternatively, the filter may comprises an analog to digital converter and control computer program code adapted to compare digital amplified signal data to a reference level.

A further system embodiment may also be directed to the ex vivo real-time detection of gamma radiation emitted at an area of interest by a subject from administration and uptake over a period of time of a radioactive analyte that decays in vivo by positron emission. Such an embodiment may include a primary ex vivo measurement sensor and a secondary ex vivo measurement sensor. The primary ex vivo measurement sensor may include a sensor housing with a radiation shield, the sensor housing with the radiation shield defining a cavity, the radiation shield further defining an aperture into the cavity, a collimator disposed within the aperture so as to admit a collimated gamma radiation into the cavity from the area of interest, a scintillation material disposed within the cavity such that the collimated gamma radiation is incident on the scintillation material, a light detector disposed within the sensor housing to detect light emitted from the scintillation material, a temperature sensor, a signal amplifier, and a sensor power source. The light detector, temperature sensor, signal amplifier, and sensor power source in operable communication.

In general, the scintillation material and light detector may be disposed within the sensor housing with the scintillation material adapted to receive a level of gamma radiation over the period of time from the in vivo radioactive analyte, and to emit photons representative of the gamma radiation level. As above, the light detector disposed with respect to the scintillation material is adapted to receive and convert the multiplied photons into signal data representative of the frequency level over time of gamma radiation received. The signal amplifier may amplify the signal data, and the measurement sensor may have at least one sensor output or port for such amplified signal data.

In this embodiment, the secondary ex vivo measurement sensor may be unshielded for measuring background gamma radiation. In addition, a collimator alignment system may be provided in operable engagement with the sensor housing for aligning the collimator to the area of interest, A temperature compensator may be coupled with the temperature sensor, such that the temperature sensor is adapted to measure an ambient temperature. The system may thus be adapted to communicate the ambient temperature to the temperature compensator, so that the temperature compensator generates a temperature correction factor based on comparison of the ambient temperature to a reference temperature. The temperature compensator may be further adapted to apply the temperature correction factor to the signal data to produce temperature compensated signal data.

The at least one computer processor includes a non-transient memory and a clock, with the computer processor in operable communication with the primary and secondary measurement sensors. The memory may have or store control computer program code executable by the at least one computer processor, the control computer program code may have a first module for measurement and a second module for data management. The first module may be adapted to receive the signal data in a record file format. The second module is adapted to receive the signal data of a record file from the first module and to transmit the compensated signal data to a desired storage. Also included may be third and fourth modules of computer program code, the third module adapted to receive stored data of a record file from the second module, (i) to apply such stored data to a predictive model to generate predictive data values over a desired period for such record file as a predictive outcome, and to transmit such predictive outcome to a desired storage; and (ii) to apply such stored data to calculate changes in the compensated signal data over a desired period, and to transmit such changes to a desired storage and the fourth module adapted to subtract signal data from the secondary ex vivo measurement sensor from signal data from the primary ex vivo measurement sensor.

This embodiment may include options corresponding to the options of the foregoing embodiment, though as appropriate for the primary ex vivo measurement sensor.

BRIEF DESCRIPTION OF THE DRAWINGS

FIGS. 4A-4C illustrate optional aspects of the system.
FIG. 41 shows an embodiment of a radiation shielding mask, while

DETAILED DESCRIPTION

Disclosed is a system for measuring gamma radiation emitted from an in-vivo administered radioactive analyte. If repeated measurements are made, these measurements will show changes in the measured radiation over time. These repeated measurements can be used to calculate parameters related to the data. The repeated measurements can also be used as inputs to predictive algorithms to predict future parameters.

The system is a hardware and software system which can be used to gather real-time or dynamic measurements of radio-labeled tracer uptake in a biological process, for example a tumor, muscle, or other tissue. It employs a sensor for the detection of gamma radiation emitted by a subject from a systemic or local administration of a radioactive analyte that generally decays in vivo by positron emission. A sensor for gamma ray detection enables the use of ex vivo or in-vivo devices, while ex-vivo devices can be safer for the subject due to their less intrusive design. Elements and capabilities of embodiments of the system are described in more detail below.

Figure 1:
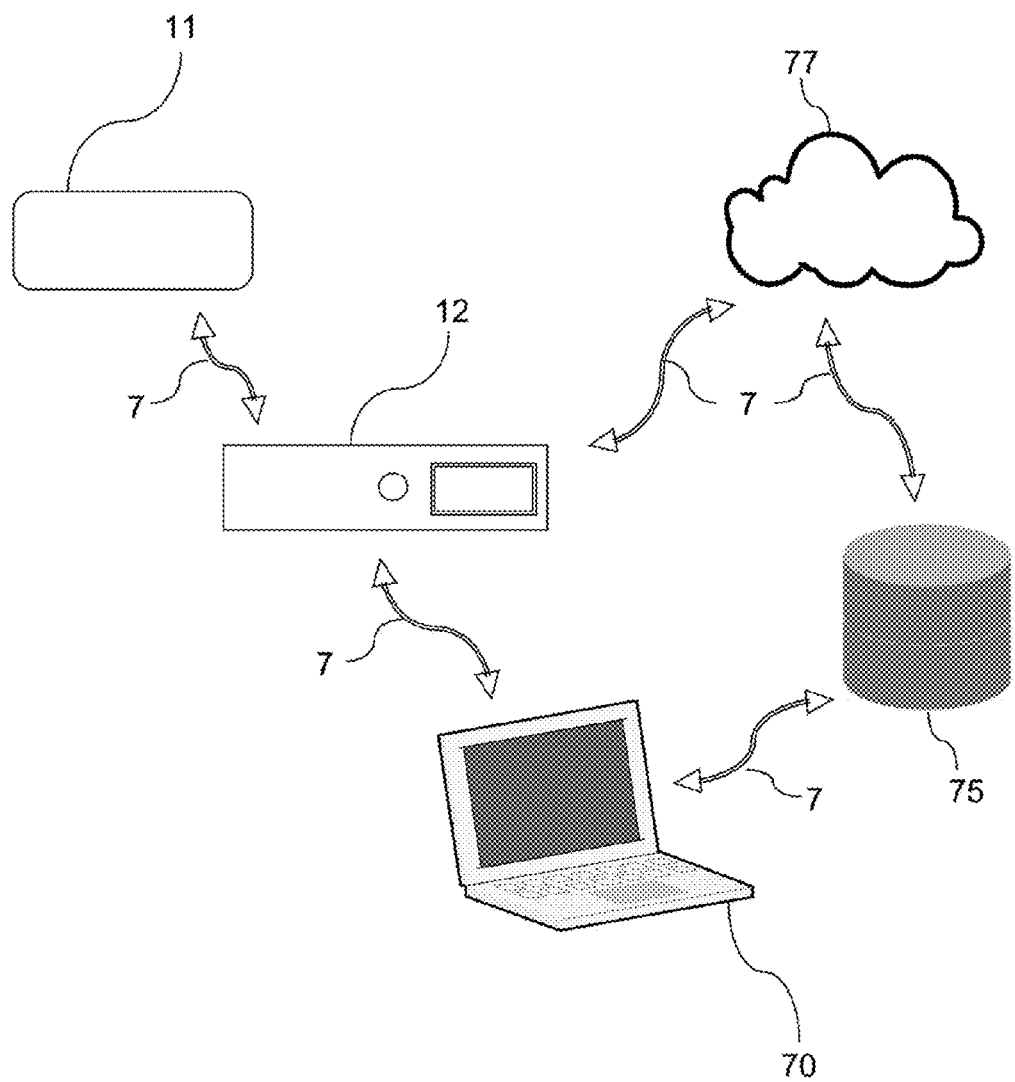
FIG. 1 is an illustration of an overview of the system.

The system 10 employs a scintillation material 20 that converts gamma radiation to visible light. A light detector 21 then converts the visible light to an electrical signal. This signal is amplified and is processed to measure the captured radiation. In ex vivo embodiments, temperature of the sensor is recorded along with this radiation measurement, and this data may be collected by a measurement controller or control device 12 into a record file 80. This record file 80, along with others like it from previous measurement sessions, may be used as inputs to calculate data parameters or as input to predictive models to predict data parameters. Record file 80 is intended simply to denote a collection of data by subject 5, and such other criteria applicable to the circumstances, such as tumor location, condition, time of test, etc, An embodiment of system 10 shown in FIG. 1 is directed to the detection of gamma radiation emitted by a subject 5 (not shown) from systemic administration of a radioactive analyte that decays in vivo by positron emission. The system 10 may include one or more measurement sensors 11 (or device for the detection of radiation), a measurement control device 12, an optional processing station 70, and optional database 75. Communication links 7 may be wired or wireless, depending on the application, and may extend data reporting or other communication to networks or the internet 77. The system 10 may include a visible, audible, or other means of indicating the status of the radioactive analyte injection, including the likelihood of injection infiltration.

Figure 2:
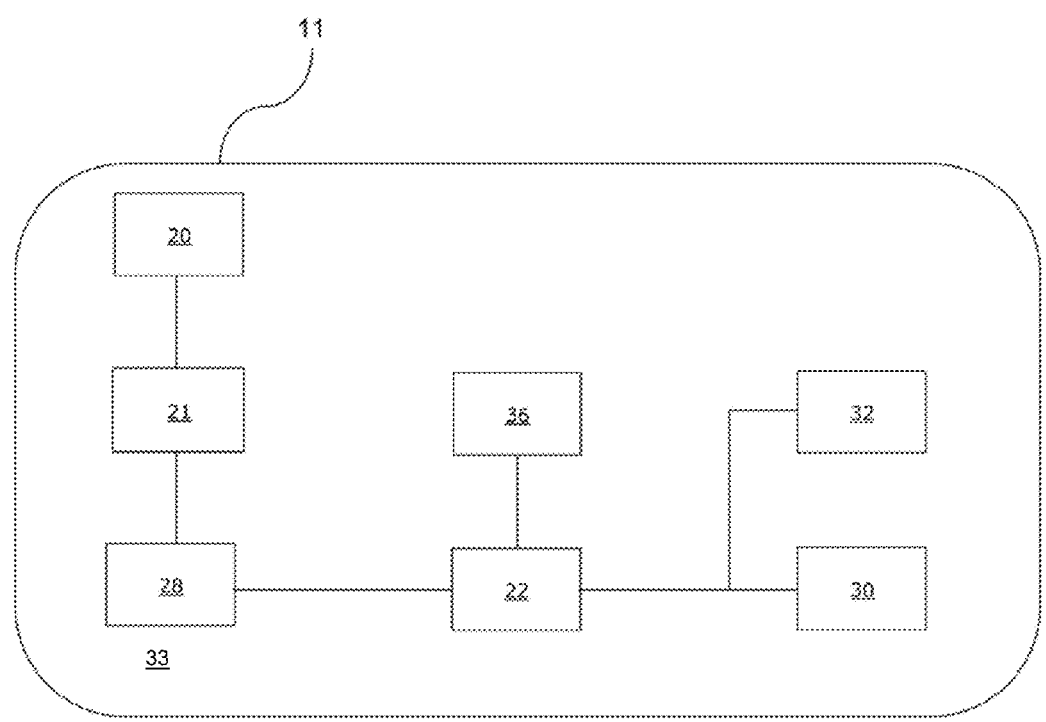
FIG. 2 is a schematic of a measurement sensor of an embodiment of the system.

With reference to FIG. 2, measurement sensor 11 may have a sensor housing 25 (not shown), a scintillation material 20, a light detector 21, a temperature sensor 36, a signal amplifier 33, a sensor processor 22, a non-transient sensor memory 30, and a sensor power supply 32. Light detector 21, temperature sensor 36, signal amplifier 33, sensor processor 22, sensor memory 30, and sensor power supply 32 may be in operable communication, whether by wiring, circuit board tracing, etc.

Figure 3:
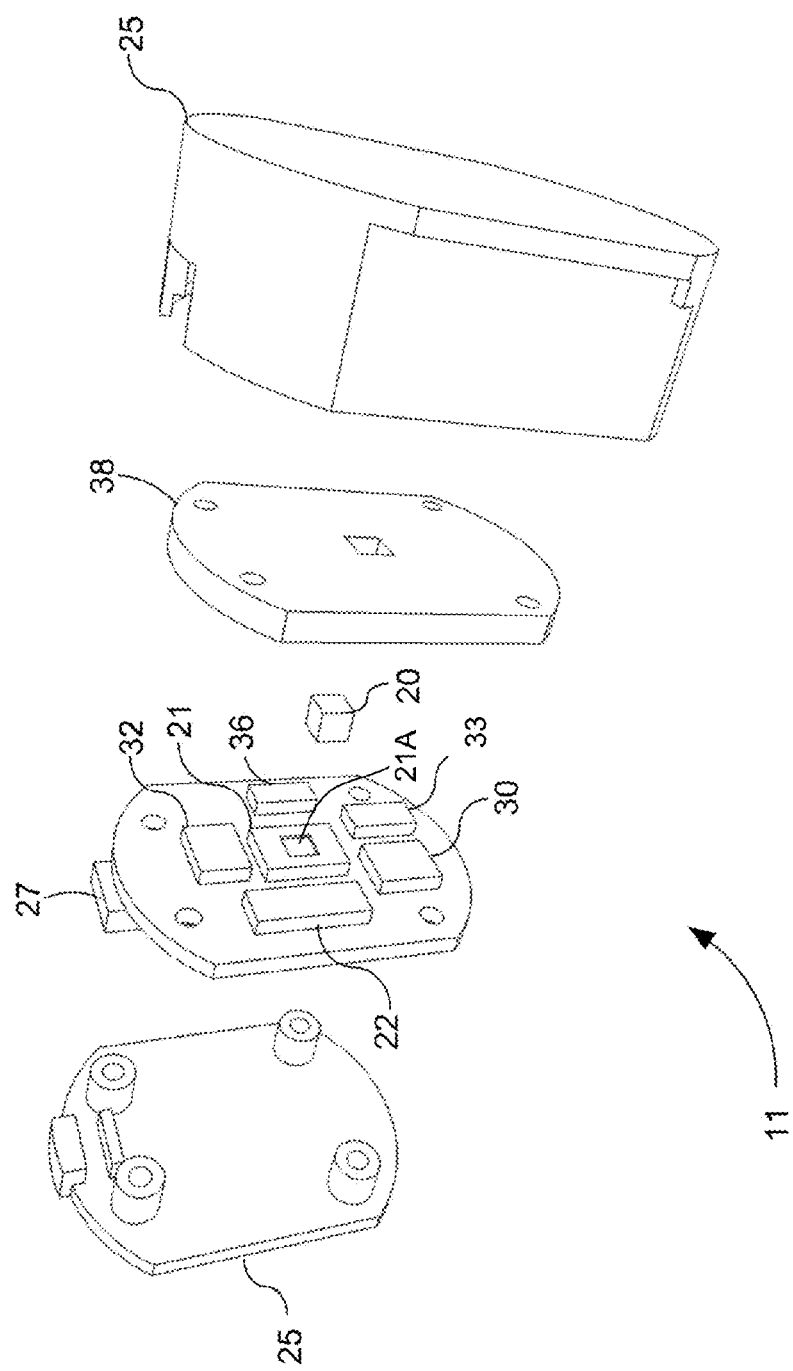
FIG. 3 is shows an embodiment of a measurement sensor of the system.
Figure 57:
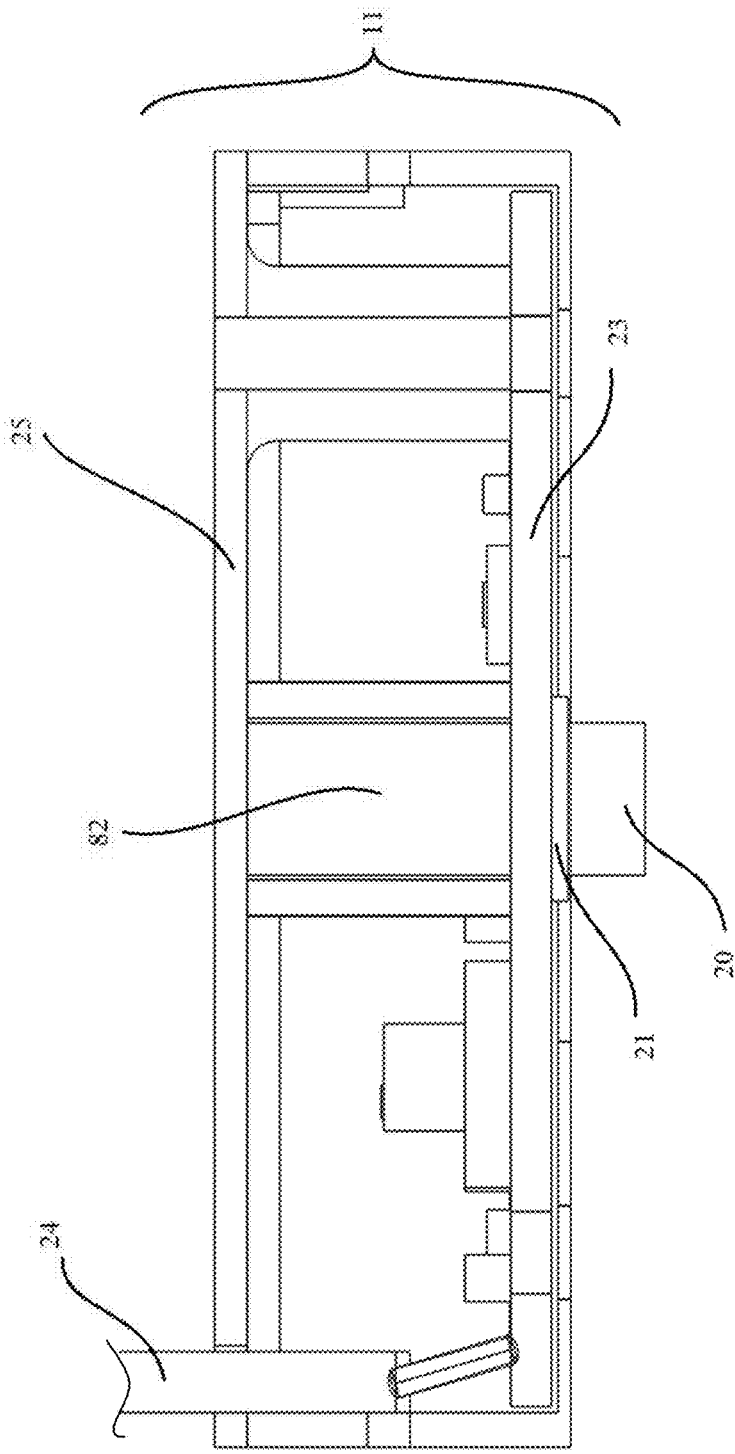
FIG. 57 shows a cut away view of an embodiment of a measurement sensor with backscatter material.
Figure 58:
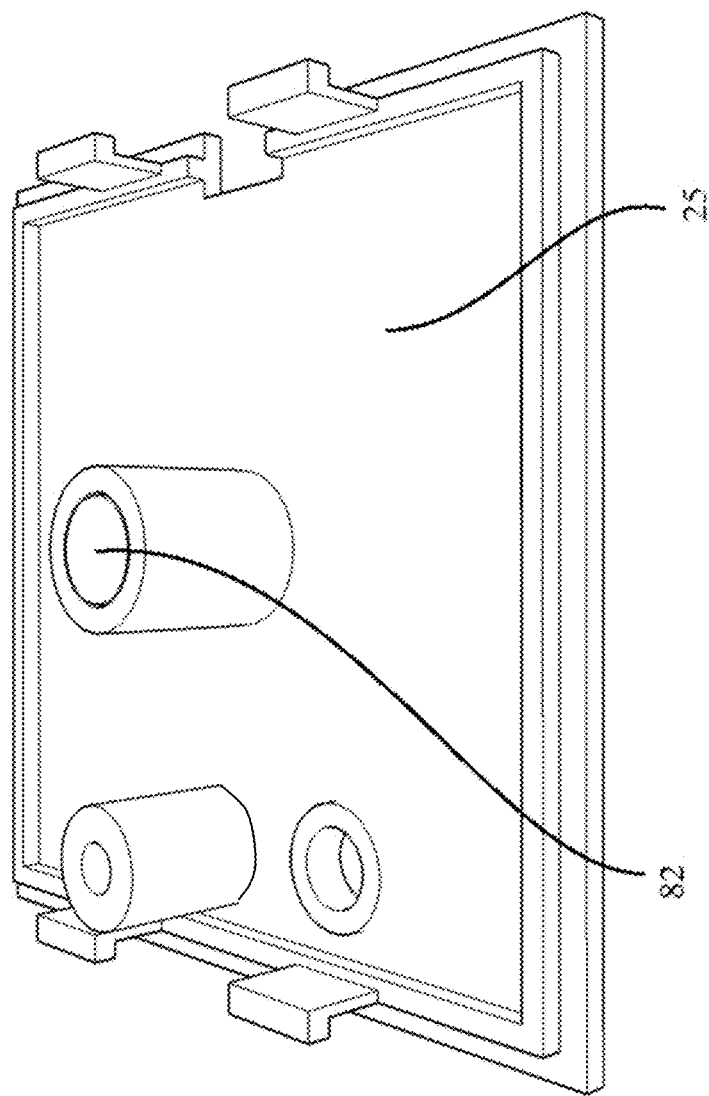
FIG. 58 shows an embodiment of a measurement sensor housing with integrated locating structure for a backscatter material.

As shown in the exploded illustration of FIG. 3, scintillation material 20 and light detector 21 may be disposed or located within housing 25 for use, depending on the application. Sensor housing 25 may be fabricated of metal (e.g., nickel, copper, brass, bronze, steel, aluminum, nickel-silver, beryllium-copper, etc.) or plastic (PE, PP, PS, PVC, ABS, etc.). Such sensor housing 25 may optionally be light proof, so as to protect scintillation material 20 and light detector 21 from ambient or surrounding light. Optionally, sensor housing 25 may define an outer surface and comprises a light-proof coating on the outer surface. Sensor housing 25 may also protect such internal components from environmental degradation, such as the exposure of scintillation material 20 to elevated humidity. Sensor housing 25 may include or incorporate a shielding mask 38 or shield for the radiation of concern, such as the ex vivo detection of gamma radiation. Shielding mask 38 may be fabricated from materials such as iridium, platinum, tungsten, gold, palladium, lead, silver, molybdenum, copper, nickel, bronze, brass, iron, steel, zinc, titanium, and aluminum. As shown in FIGS. 57 and 58, any number of embodiments the sensor housing 25 could include a structure for placement and alignment of a backscatter material 82.

In use, and as shown in FIGS. 4A-C, embodiments of sensor housing 25 may include an adhesive 25A adapted for the removable attachment of the housing to the skin of the subject 5. Optionally, system 10 may include a measurement sensor carrier 35 adapted to removably engage with the measurement sensor 11. The measurement sensor carrier 35 may define a carrier surface with a portion of which may comprise an adhesive 35A adapted for removable attachment of the measurement sensor carrier 35 to the skin of a subject 5 (not shown). Optionally, measurement sensor carrier 35 includes or defines one or more alignment features 35F that permit the repeated alignment of the measurement sensor carrier 35 to the subject, For example in the embodiment as shown, measurement sensor carrier 35 defines two features 35F that could be used to align a marker to make a mark or stain dot on the skin of subject 5. For a repeated trial, measurement sensor carrier 35 might be placed in a position so that alignment features 35F might align with the marks on the skin of subject 5, ensuring that measurement sensor 11 is in the proper location. Measurement feature 35F may include a variety of approaches depending on the application, such as pads for temporary tattoo markings, peripheral outline ridges, guides permitting the marking of orientation axes, etc. Additionally, embodiments of sensor housing 25 may include a means of attachment to an arm band 78 for attachment to the arm of subject 5. This arm band may include hook and loop fasteners 79 or other means of securing to subject 5. An embodiment may include a pocket or other means of securing the sensor 11 with respect to the arm band.

Sensor power supply 32, or the other power supplies discussed herein, may be a battery, a hardwire power connection, transformer, or some form or source of power generation. In some embodiments, sensor power supply 32 in particular, may be a microelectromechanical machine adapted to generate electricity from subject 5, possibly employing the motion of subject 5, or blood pressure, etc.

Scintillation material 20 may be placed within a gamma radiation flux, with scintillation material 20 being adapted to receive a level of gamma radiation from the in vivo radioactive analyte and to emit photons representative of or corresponding to the gamma radiation level. Light detector 21 may be juxtaposed, located, or generally disposed with respect to the scintillation material 20 so as to be adapted to receive and convert the multiplied photons into signal data representative of the level of gamma radiation received. It is contemplated that some applications may include mechanisms or structure for directing light from scintillation material 20 to light detector 21, such as fiber optics, prisms, reflectors, etc. Optionally, and as shown in FIG. 3, light detector 21 may have an active area 21A sensitive or receptive to light as described herein, and the scintillation material 20 may be configured and sized to substantially match the active area. Which may improve efficiency and reduce the effect of stray light or background signals.

The scintillation material 20 may be selected for or adapted to the radiation detection application. In some embodiments for gamma radiation, scintillation material 20 may be selected from a group consisting of bismuth germanate, gadolinium oxyorthosilicate, cerium-doped lutetium oxyorthosilicate, cerium-doped yttrium oxyorthosilicate, sodium iodide, thallium-doped sodium iodide, polyvinyltoluene, and cadmium zinc telluride.

Measurement sensors 11 may include a signal amplifier 33 that is adapted to amplify the signal data, a sensor memory 30 including a measurement sensor identifier 16 (FIG. 6), and at least one sensor output port 27 for communication or output of the amplified signal data Depending on the mode of communication desired, sensor output port 27 may be any of a variety of ports, such as electrical jack, computer communication (e.g., CAT-5), optical, infrared, radio transmitter, etc.

Figure 5A:
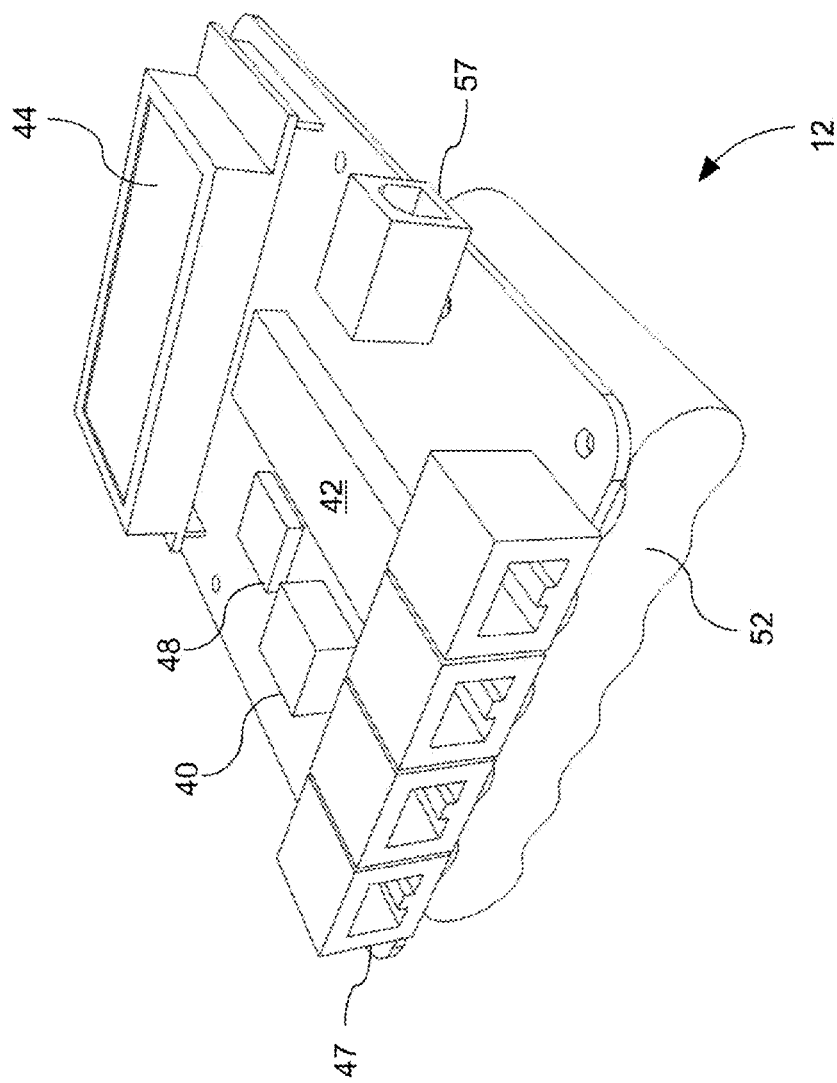
FIGS. 5A-5C illustrate embodiments of measurement control devices.
Figure 5B:
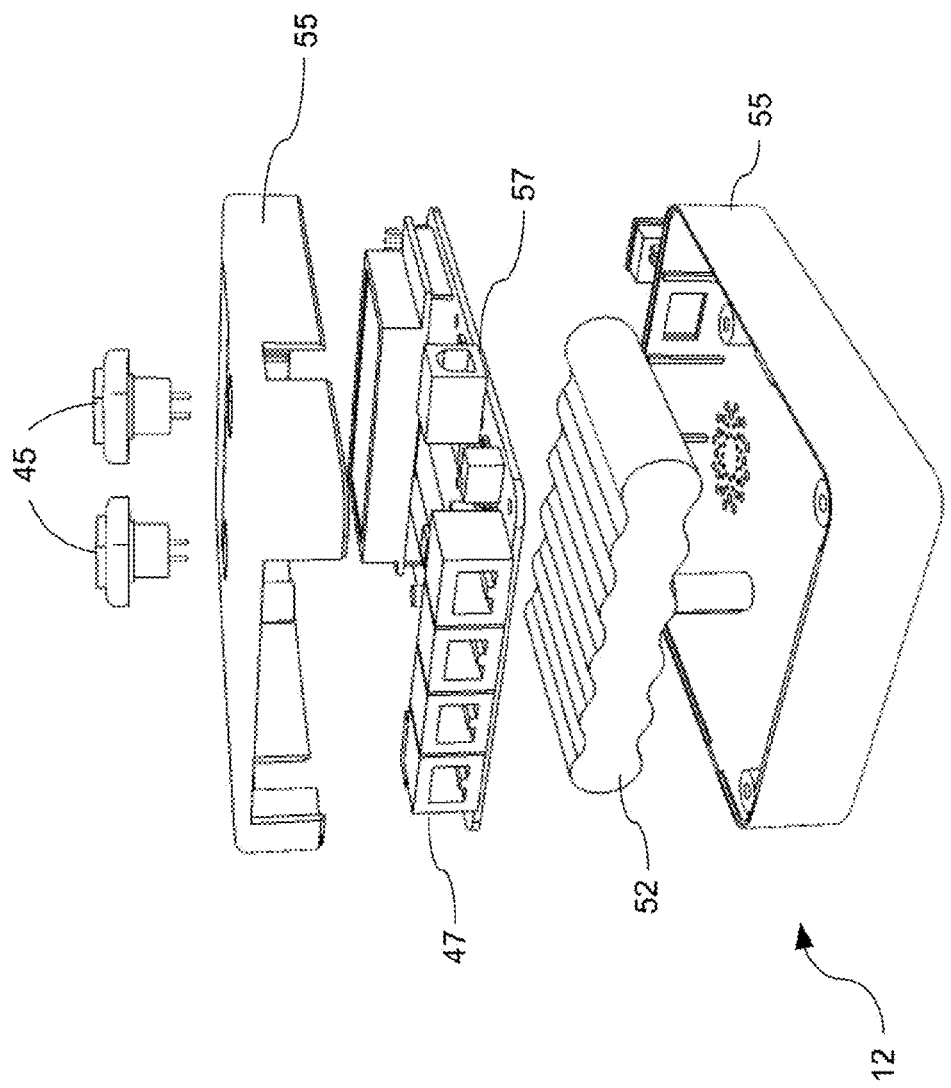
Figure 5C:
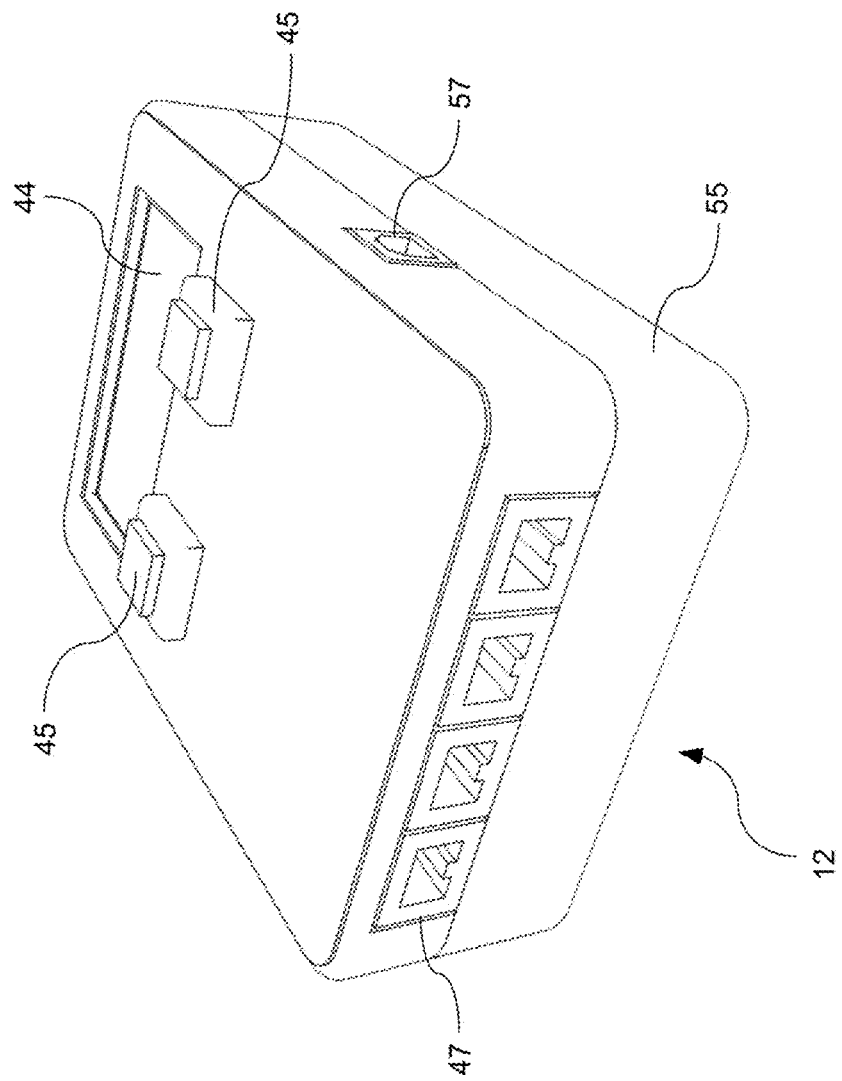

In reference to the examples in FIGS. 5A-C, the system 10 may include a controller or measurement control device 12 having a control processor 42, a non-transient control memory 40, a control power supply 52, and a clock 48, all in operable communication, whether by wiring, circuit board tracing, etc. The measurement control device 12 may include a control input port 47 operably engaged with the sensor output port 27 (not shown) and adapted to receive amplified signal data from the measurement sensor 11. Operable engagement may include wired or wireless communication, in any of a variety of communication protocols. For example, control input port 47 may be operably engaged with the sensor output port 27 by cable (e.g., multiconductor cable 24), circuit board tracing, or by wireless communication. In addition to amplified signal data, it may be desirable to communicate other data or information from measurement sensor 11 to measurement control device 12, such as operating parameters, power storage, equipment status, or other sensor data. Optionally, measurement control device 12 may include a display 44 and data entry device 45, such as a touch screen, or other input/output structure. Embodiments may include a controller or measurement control device 12 and one or more sensors 11 contained within the same housing, and operably engaged.

The control memory 40 may, among other things, include control computer program code 56 (FIG. 6) executable by the control processor 42. Control computer program code 56, for example, may include a first module 61 for implementing measurement functions and a second module 62 for data management. For example, the first module 61 may be adapted to receive a previously assigned measurement sensor identifier 16 (discussed below), the signal data, and a subject identifier and to associate the signal data, sensor identifier, and measurement sensor identifier 16 in a record file 80 format. The second module 62 may be adapted to receive the signal data of a record file 80 from the first module 61 and to transmit the compensated signal data to a desired storage. Such storage may be local memory (e.g., sensor or control), external memory, a remote computer memory, networked memory (wireless or wired), or memory accessed via the internet.

The system 10 may include a temperature compensator 50 coupled with the temperature sensor 36, the temperature sensor 36 adapted to measure an ambient temperature within the system 10 adapted to communicate the ambient temperature to the temperature compensator 50. In this way, the temperature compensator 50 may be adapted to generate a temperature correction factor based on comparison of the ambient temperature to a reference temperature. As discussed below, components within measurement sensor 11 may be temperature sensitive. The temperature compensator 50 may also be adapted to apply the temperature correction factor to the signal data to produce temperature compensated signal data. Temperature compensation may not be required for embodiments directed to in vivo sensing. Additionally, some embodiments of the system 10 may include a means of temperature response calibration which would nullify the impact of temperature on the operation of system 10. This nullification could be accomplished by measuring the response a sensor 11 has with respect to temperature, and then modifying the parameters of amplifier 33 or other circuit components so as to counteract this temperature response.

Optionally, as shown in FIGS. 7-8, and FIGS. 29-33, embodiments of measurement sensor 11 may include an internal disposed light shield 28. Such an embodiment may include a printed circuit board assembly 23P having a board 23 defining a plane with a first surface 23A and an opposing second surface 23B. Light shield 28 may be adapted for mounting onto the first surface 23A of the board 23, thereby shielding the scintillation material 20 and light detector 21 from ambient light. The scintillation material 20 and light detector 21 may be ensconced in or surrounded by light shield 28. For example, given that the scintillation material 20 has a first width parallel with the plane and the light detector 21 has a second width parallel with the plane, then light shield 28 may define a first cavity 28A with a third width equal or greater than the first width such that the first cavity 28A is adapted to receive the scintillation material 20, and the light shield 28 may also define a second cavity 28B with a fourth width equal or greater than the second width such that the second cavity 28B is adapted to receive the light detector 21. First and second cavities 28A., 28B may be in communication and in such proximal relation that the light shield 28 optically aligns the scintillation material 20 to the light detector 21 when the scintillation material 20 is received by the first cavity 28A and the light detector 21 is received by the second cavity 28B. These components may be operably engaged with the printed circuit board assembly 23P when mounted. For purposes herein, the term "width" is intended to connote an effective width that permits the nesting described, and not any particular required cross sectional shape. In other words, the term "width" is intended to permit the reception of the components as described, and not to limit cross section shape of those components beyond their interrelation. In an embodiment of the light shield 28, a light proof sealant 81 may be used to seal the cavities after assembly of the scintillation material 20 and light detector 21. This light proof sealant 81 may, for example, be an epoxy, caulk, potting compound, etc.

Such a light shield 28 may be made from materials selected from a group of metals (e.g., copper, brass, bronze, steel, aluminum, nickel-silver, beryllium copper, silver, gold, nickel), or plastic (e.g., ABS, Acetal, Acrylic, Fluoroplastic, Polycarbonate, Nylon, PVC, Polypropylene, Polystyrene, Polyethylene ABS, Acetal, Acrylic, Fluoroplastic, Polycarbonate, Nylon, PVC, Polypropylene, Polystyrene, Polyethylene). Optionally, the light shield 28 may be made from one material and plated or coated in another, to enhance its ability to be soldered or mounted on printed circuit board assembly 23P.

If made from metal or metal clad or plated plastic, the light shield 28 may be fixed into place on printed circuit board assembly 23P as a surface-mount-component using either leaded or lead-free solder, or as a through-hole-component using portions of the light shield 28 that protruded through holes in the circuit board, the holes then filled with solder. If made from plastic, the light shield 28 may be fixed into place on the printed circuit board assembly 23P as a snap-on part with portions of the shield that protrude through holes in the printed circuit board assembly 23P that spring into position and resist reversing out of the holes, as a swage-on part with portions of the shield that protrude through such holes and that are then melted or swaged to prevent them from reversing out of the holes. Additionally, light shield 28 may be mounted detached from the printed circuit board, incorporating wired connections thereto.

Optionally, light shield 28 may have one or more through-holes in it to allow pressure to equalize during assembly or to allow for out-gassing during assembly. Such holes may then be covered, possibly with light-proof foil tape or sealant 81, after assembly to complete the light-proof nature of the shield.

Figure 7:
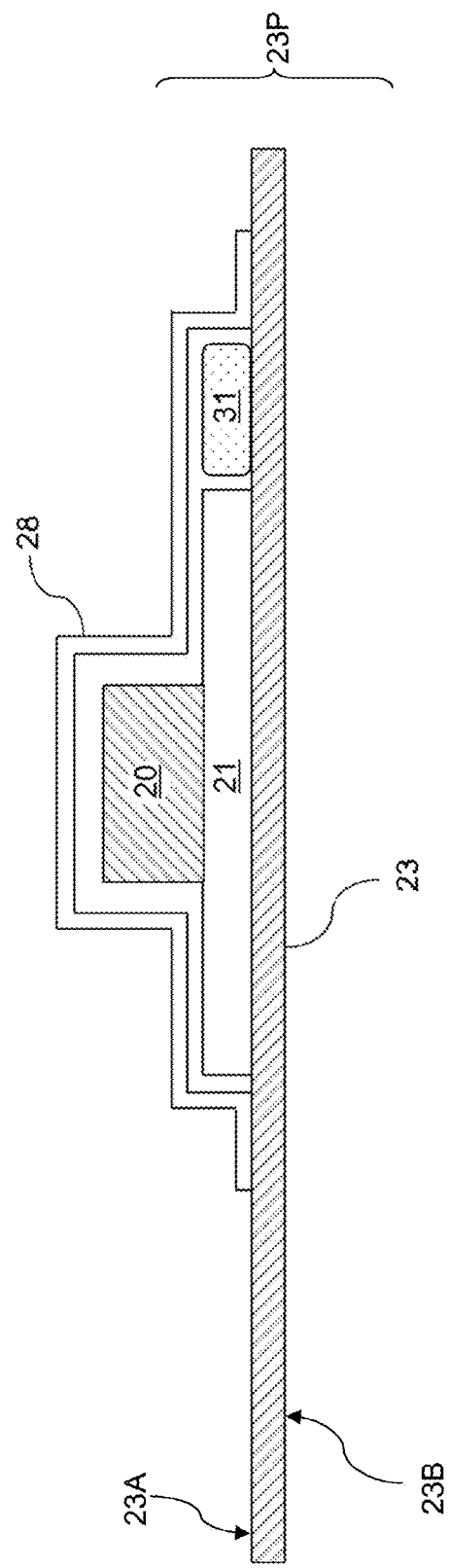
FIG. 7 shows an embodiment of a printed circuit board and light shield.
Figure 8B:
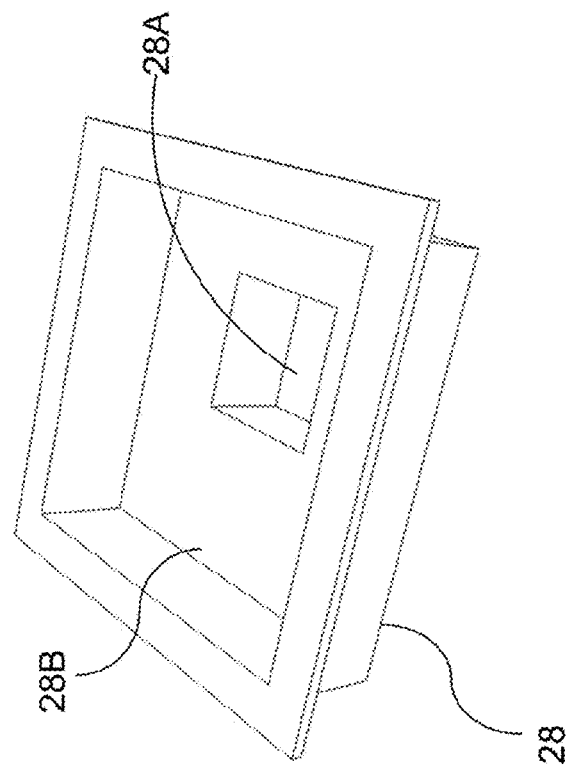
FIGS. 8A-8B illustrate an embodiment of a light shield.
Figure 8A:
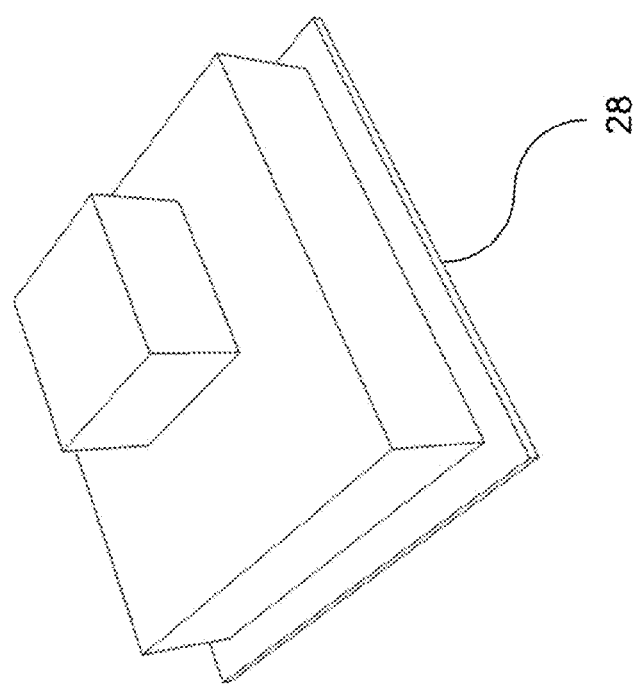

As shown in FIG. 7, light shield 28 may also enclose a light emitter 31 (e.g., LED, light bulb, laser diode) such that the light emitter could be used to generate pulses of light within the enclosure of the light shield 28 to test the light detector 21. Thus, system 10 may include a light emitter 31 in operable communication with the sensor power supply 22, the light emitter 31 disposed within first or second cavity 28A, 28B (or other proximal cavity), such that the light shield 28 is adapted to receive the light emitter 31 in a location that is proximal to the light detector 21.

In some embodiments, the control computer program code 56 further comprises a third module 63 adapted to receive stored data of a record file from the second module 62. The third module 63 may apply such stored data to a predictive model to generate predictive data values over a desired period for such record file as a predictive outcome, and to transmit such predictive outcome to a desired storage. In other embodiments, the third module 63 may to apply such stored data to calculate changes in the compensated signal data over a desired period, and to transmit such changes to a desired storage. In other embodiments, the third module 63 may to apply such stored data to calculate changes in the compensated signal data from background data over a desired period, and to transmit such changes to a desired storage. Such background data may be drawn from a second measurement sensor 11, a previously calculated background radiation level, or a separate radiation sensor, depending on the application, in other embodiments, the third module 63 may be adapted to apply such stored data to calculate the quality of a radioactive analyte injection, such as to monitor changes in compensated signal data or otherwise calculate the likelihood of injection infiltration. A result of this may be transmitted to a display and/or a desired storage. This could alert or inform the user of the status, whether by visual, audible or other indication means.

Figure 24:
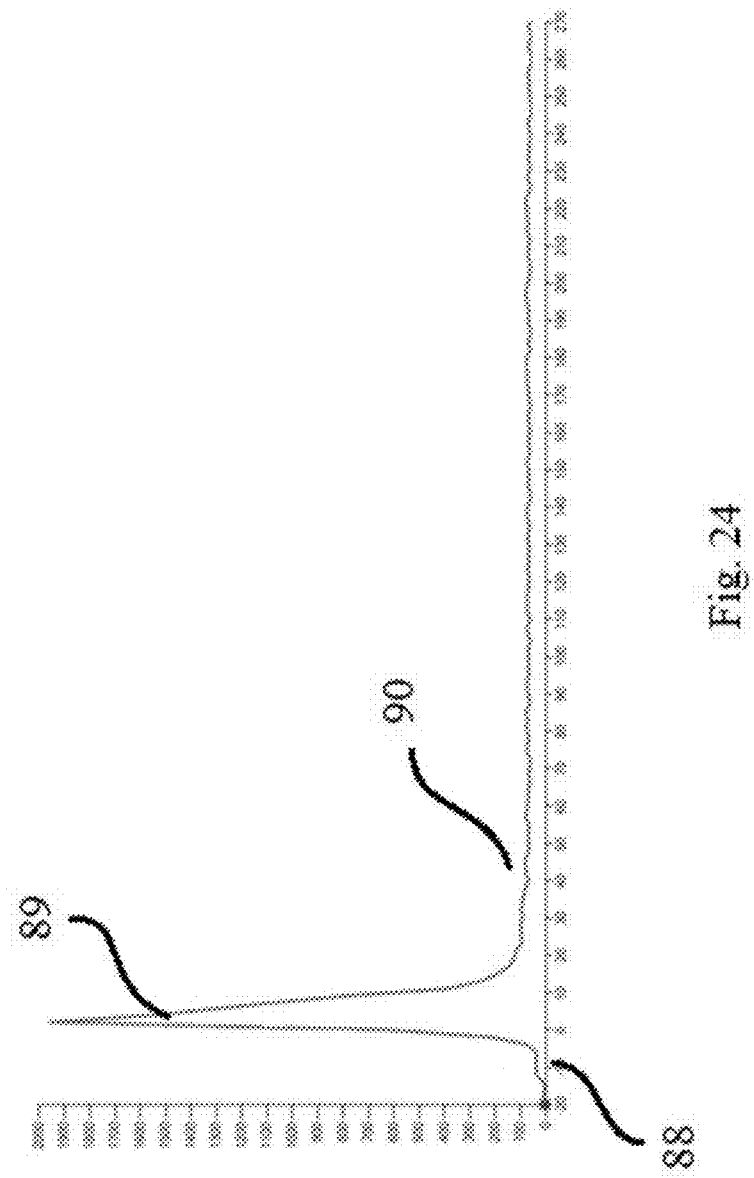
FIG. 24-26 show the output from an injection arm sensor from administration or injection of a radioactive analyte, with FIG. 24 a proper administration and FIGS. 25 & 26 showing improperly administered radioactive analyte.
Figure 25:
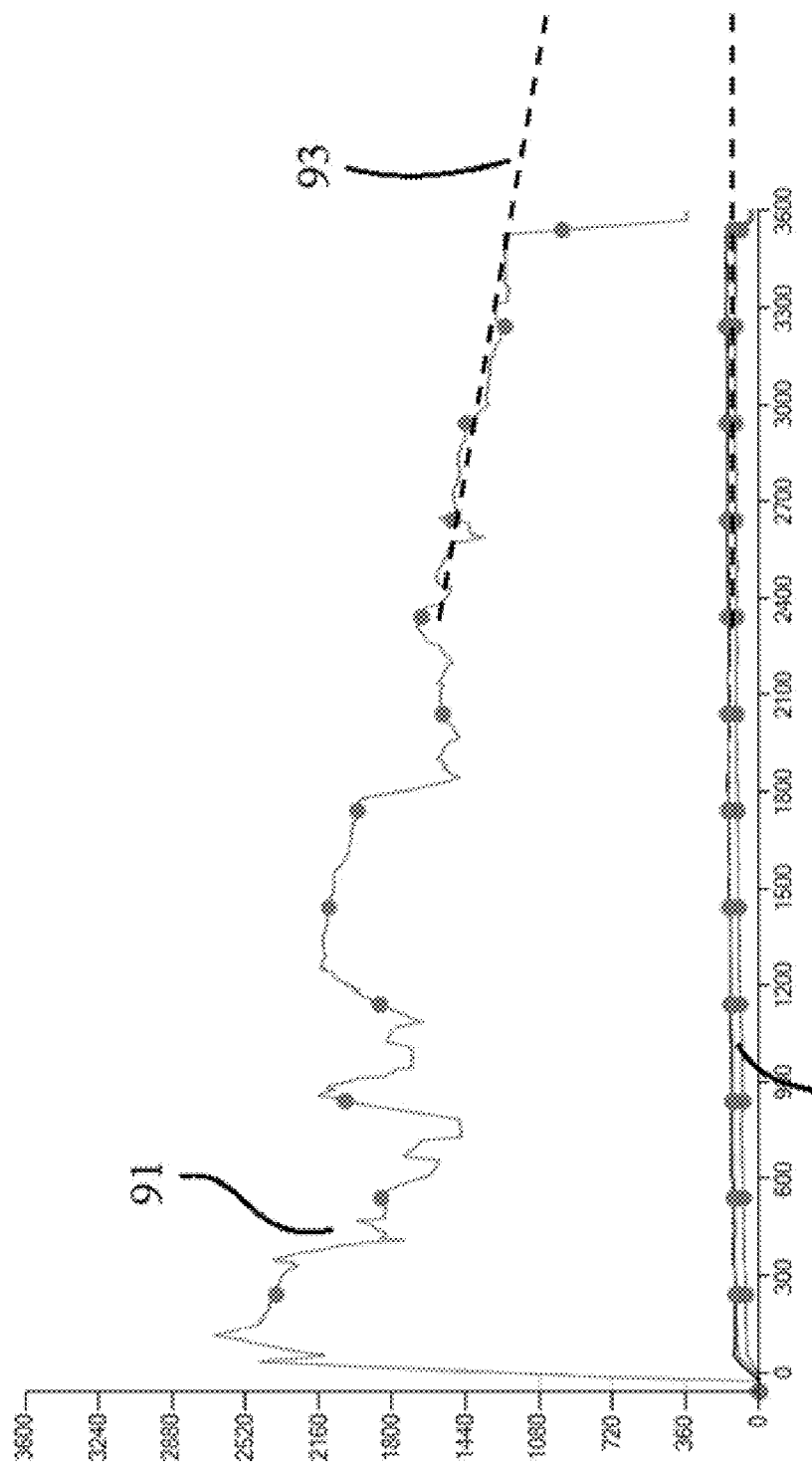
Figure 26:
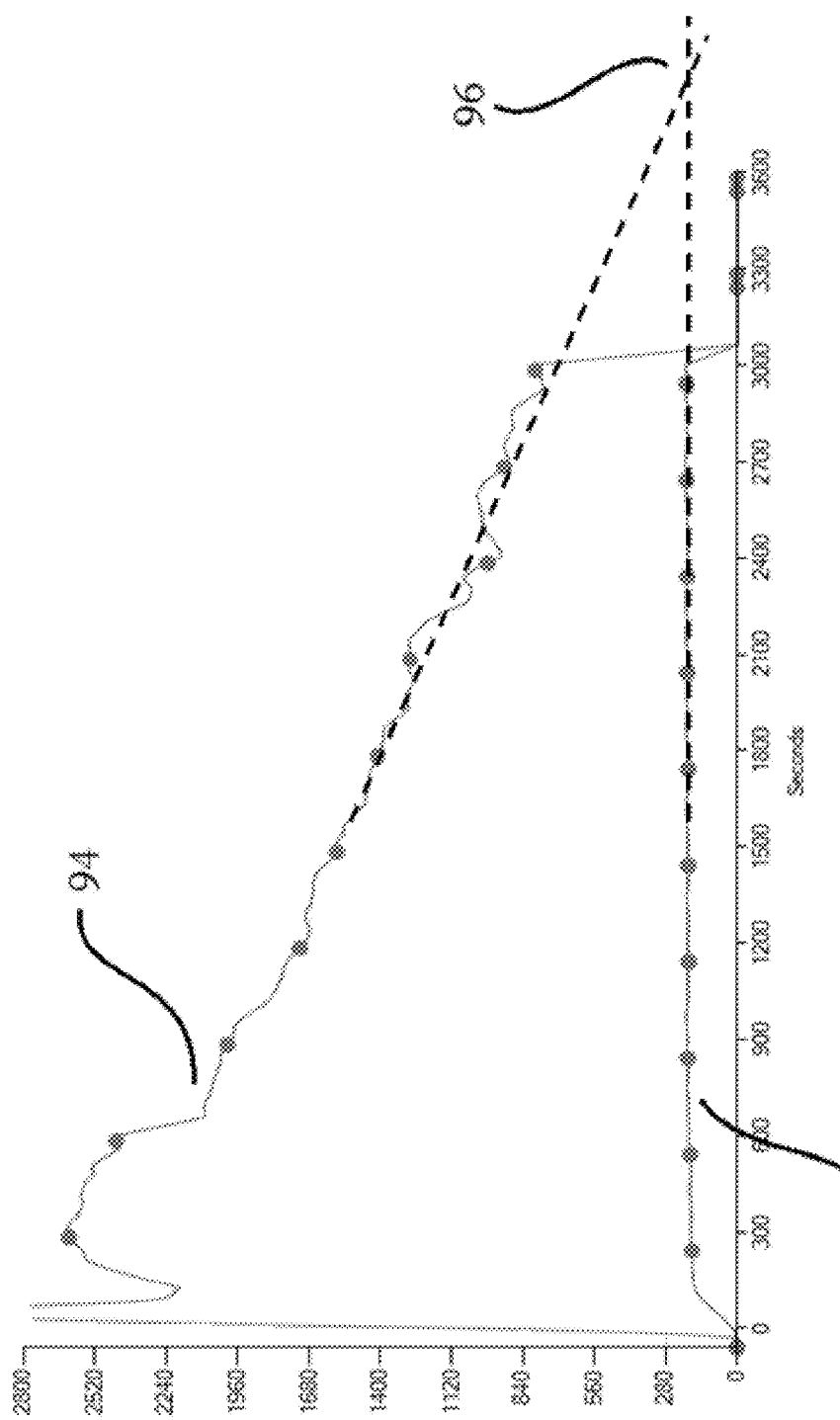

FIG. 24 shows the radiation pulse count amplitude or output over time from an injection arm sensor 11 with a properly administered radioactive analyte, with a low level prior to injection 88, an injection spike 89, and a low level post injection 90. This signal data forms a distinctive parametric pattern (i.e., amplitude, slope, time), which is characteristic of the proper administration of a radioactive analyte. The injection spike 89, followed by the low level post injection demonstrates dispersal of the radioactive analyte after a proper administration or injection. FIG. 25 shows an output from an injection arm sensor 11 with an improperly administered radioactive analyte (i.e., infiltration or extravasation) in 91, as well as non-administration arm low levels 92, and illustrating the approximate extremely high level of counts or amplitude at the approximate time 93 at which a PET Scan might typically be taken. FIG. 26 shows an output from an injection arm sensor 11 with another improperly administered radioactive analyte (i.e., infiltration or extravasation) in 94, as well as non-administration arm low levels 95, and illustrating the approximate normal low level of counts or amplitude (obtained by extrapolating from available measurements, as shown by the dashed lines) at the approximate time 96 at which a PET Scan might typically be taken, The parametric patterns and data characteristic of improper administration can thus be distinguished in comparison to the parametric pattern and data of proper administration. Without the present approach, the improper administration would be impossible for clinicians to detect. In addition to infiltration or extravasation, improper administration may include or be characterized by other inaccuracies in the desired dispersion of radioactive analyte (e.g., protocol deviation).

Figure 9:
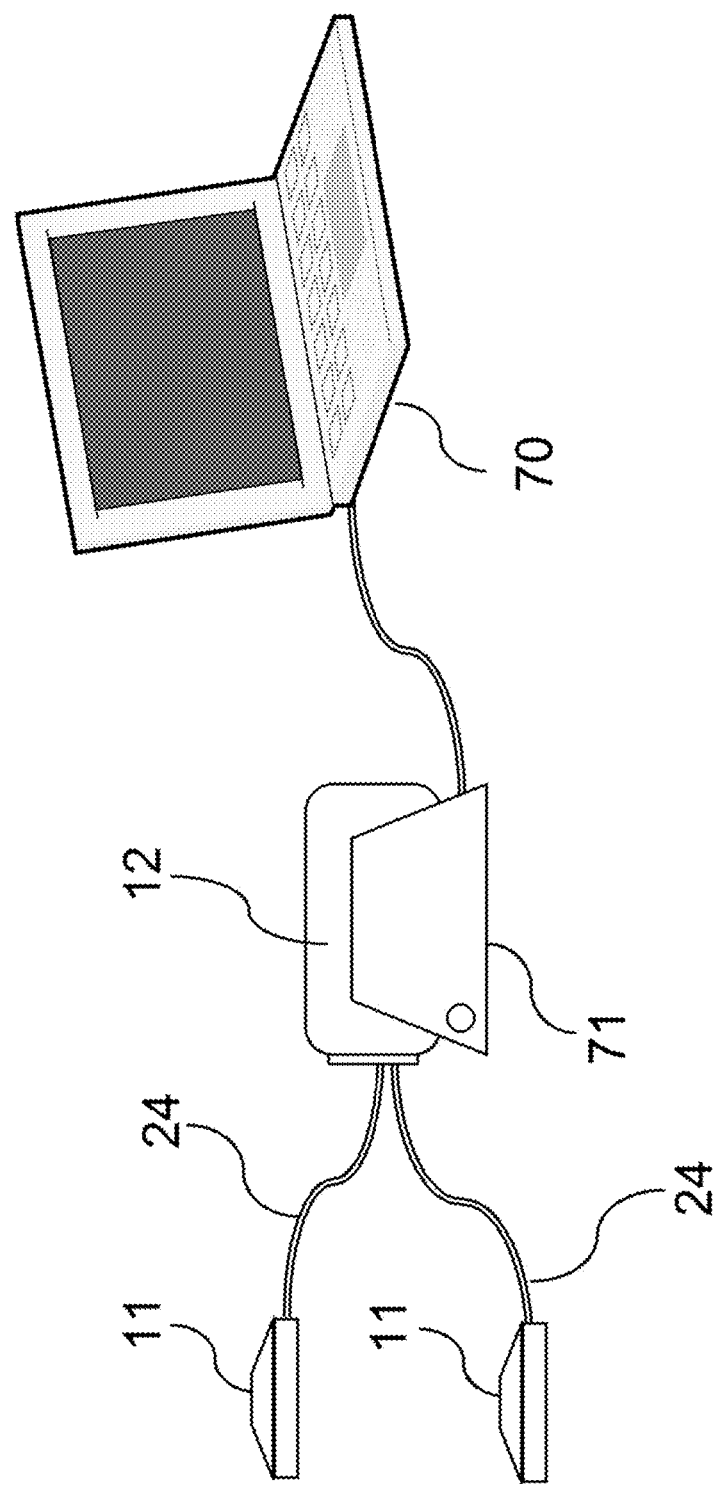
FIG. 9 shows an aspect of embodiments of the system.

In some embodiments, system 10 may include a processing station 70 (FIGS. 1 & 9). Processing station 70 may be a computer in communication with measurement control device 12. Embodiments of processing station 70 may include a station processor, a non-transient station memory, and a station power supply; the station processor, station memory, and station power supply are in operable communication. The processing station 70 may have a station input port operably engaged with the control output port and adapted to receive data from the measurement control device 12. In some embodiments, the role of measurement control device 12 and station 70 may be merged.

Similar to measurement control device 12, the processing station 70 may include station computer program code 76 executable by the station processor, the station computer program code including a third module 63 adapted to receive stored data of a record file from the second module 62, to apply such stored data to a predictive model to generate predictive data values over a desired period for such record file as a predictive outcome.

Optionally, processing station 70 may include a docking device 71 for the measurement control device 12. The docking device 71 may be in operable communication with the station processor. Docking device 71 could be adapted to receive the measurement control device in the form of a holder, retainer, charger, or cradle. When measurement control device 12 is docked, the docking device 71 may provide an electrical connector that engages with measurement control device 12 for data communication and power exchange. In one embodiment, the third module 63 may be adapted to calculate the quality of the radioactive analyte injection. Whether by identifying certain changes or modelling, such as to calculate the likelihood of injection infiltration. The station computer program code could then transmit the result of this calculation to a desired storage. Additionally, the station computer program code could alert the user of the calculation result using visual, audible or other indication means.

In some embodiments, a predictive model may be a classification machine learning model. In other embodiments, predictive model may be an unsupervised cluster analysis. Such an unsupervised cluster analysis, or other predictive model, may be adapted to predicting future outcome, predicting an effect of tumor treatment, and predicting metastasis.

Some embodiments may involve multiple measurement sensors 11. For example, a system 10 may include a first and second measurement sensor 11, the first measurement sensor 11 adapted to the detection of test gamma radiation emitted by a subject from systemic or local administration of a radioactive analyte that decays in vivo by positron emission proximate to a test area. The second measurement sensor 11 may be adapted to the detection of background gamma radiation emitted by a subject from systemic or local administration of a radioactive analyte that decays in vivo by positron emission proximate to a background area. Depending on the application, the control computer program code 56 or station computer code 76 may further include a fourth module 64 adapted to receive stored data of a record file from the second module 62 including data from the first and second measurement sensors 11 and to subtract signal data from the second measurement sensor 11 from signal data from the first measurement sensor 11. In other applications, the fourth module 64 may be adapted to receive stored data of a record file from the second module 62 including data from the first and second measurement sensors 11, and to subtract signal data from the second measurement sensor 11 from signal data from the first measurement sensor 11. Such embodiments may permit the subtraction of background radiation from sensor data. Additionally, such embodiments may permit the estimation of the likelihood that the system or local radioactive analyte injection resulted in infiltration.

In some embodiments, the signal data may be a plurality of pulses at a pulse frequency over time. The first module 61 may be adapted to communicate a sampling frequency instruction to the sensor processor 22, the sampling frequency instruction being a function of the pulse frequency of the signal data. In some embodiments, the first module 61 is adapted to communicate an increasing sampling frequency instruction upon an increase in pulse frequency.

An aspect of present approach is a sensor or device for the detection of radiation, the device comprising a measurement sensor 11 with a housing 25, a scintillation material 20, a light detector 21, a light shield 28, a temperature sensor 36, a signal amplifier 33, a sensor processor 22, a non-transient sensor memory 30, and a sensor power supply 32. Light detector 21, temperature sensor 36, signal amplifier 33, sensor processor 22, sensor memory 30, and sensor power supply 32 may be in operable communication by a printed circuit board assembly 231. Printed circuit board assembly 23P may have a board 23 defining a plane having a first surface 23A and an opposing second surface 23B. Light shield 28 may be adapted for mounting onto the first surface 23A of the board 23, thereby shielding the scintillation material 20 and light detector 21 from ambient light. The scintillation material 20 and light detector 21 may be ensconced in or surrounded by light shield 28. For example, given that the scintillation material 20 has a first width parallel with the plane and the light detector 21 has a second width parallel with the plane, then light shield 28 may define a first cavity 28A with a third width equal or greater than the first width such that the first cavity is adapted to receive the scintillation material 20, and the light shield 28 may also define a second cavity 28B with a fourth width equal or greater than the second width such that the second cavity 28B is adapted to receive the light detector 21. First and second cavities 28A, 28B may be in communication and in such proximal relation that the light shield 28 optically aligns the scintillation material 20 to the light detector 21 when the scintillation material 20 is received by the first cavity 28A and the light detector 21 is received by the second cavity 28B. These components may be operably engaged with the printed circuit board assembly 23P when mounted, The scintillation material 20 and light detector 21 are thus disposed within the light shield 28 with the scintillation material 20 adapted to receive a level of gamma radiation and to emit photons representative of the gamma radiation level. Light detector 21 is disposed with respect to the scintillation material 20 so as to be adapted to receive and convert the multiplied photons into signal data representative of the level of radiation received.

As above, the signal amplifier 33 may be adapted to amplify the signal data, the sensor memory 30 including a measurement sensor identifier, the measurement sensor 11 having at least one sensor output port 27 for such amplified signal data. Optionally, the light shield 28 may be mounted to the first surface 23A of the board with solder. In some embodiments, light shield 28 is selected from a group consisting of metal: copper, brass, bronze, steel, aluminum, nickel-silver, beryllium copper, silver, gold, and nickel.

Figure 10A:
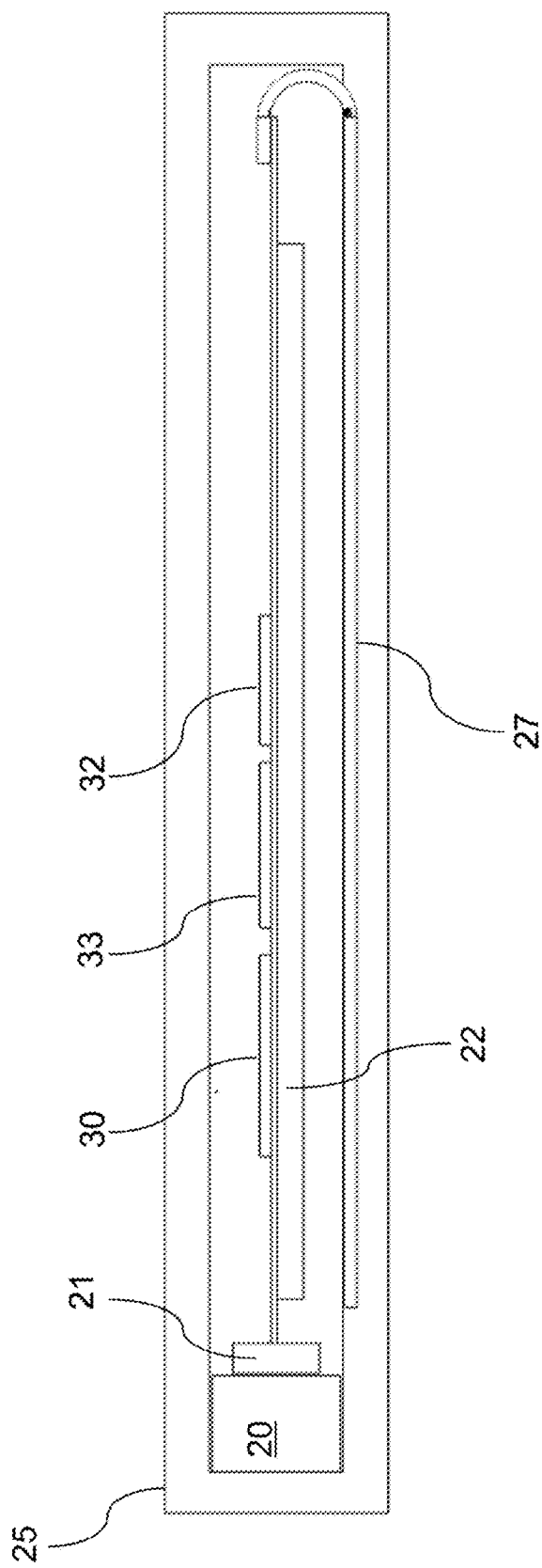
FIGS. 10A-10B show embodiments of a measurement sensor.
Figure 10B:
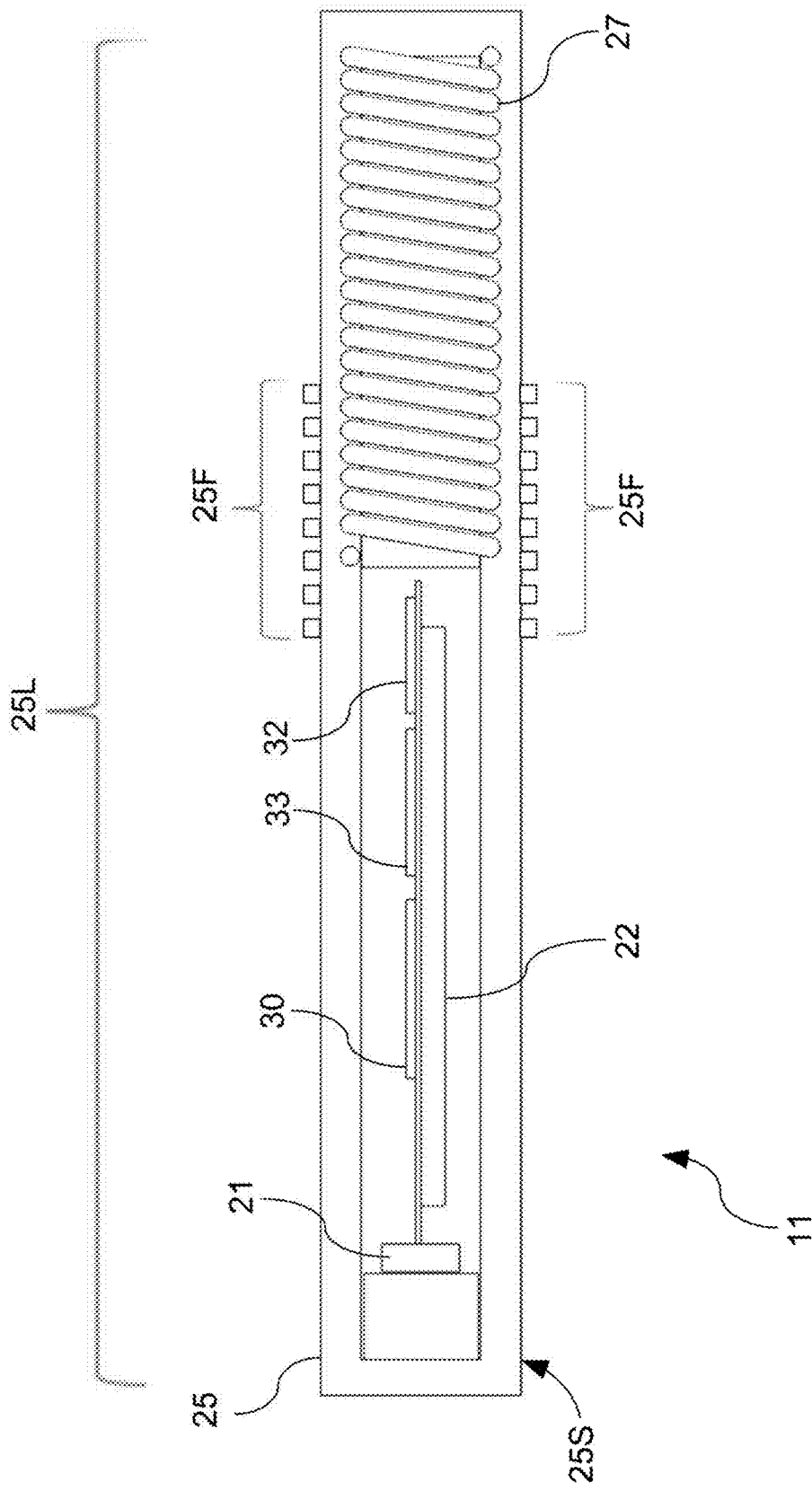

An aspect of some embodiments of system 10 for the detection of gamma radiation emitted by a subject is that at least one measurement sensor 11 may have a hermetically sealed sensor housing 25 of biocompatible material, a scintillation material 20, a light detector 21, a signal amplifier 33, a sensor processor 22, a non-transient sensor memory 30, and a sensor power supply 32, as shown in FIGS. 10A-10B. Light detector 21, signal amplifier 33, sensor processor 22, sensor memory 30, and sensor power supply 32 may be in operable communication, whether by direct wiring, circuit board tracing, wireless interaction, etc. Optionally, sensor housing 25 biocompatible material may be selected from a group consisting of glass, polyether ether ketone, and ultrahigh-molecular-weight polyethylene appropriate for the application, such as meeting implantable standards for in vivo applications, for example. As a further option, sensor housing 25 may comprise an anchor 25F for securing an in vivo application in a desired location for testing or sensing.

Similar to as discussed above with reference to FIG. 3, light detector 21 may have an active area 21A and the scintillation material 20 may be configured to substantially match the active area 21A. The scintillation material 20 and light detector 21 may be disposed within the sensor housing 25 with the scintillation material 20 adapted to receive a level of gamma radiation from the in vivo radioactive analyte and to emit photons representative of the gamma radiation level, the light detector 21 disposed with respect to the scintillation material 20 so as to be adapted to receive and convert the multiplied photons into signal data representative of the level of gamma radiation received. The signal amplifier 33 may be adapted to amplify the signal data. The sensor memory 30 may include a measurement sensor identifier 16, the measurement sensor 11 having at least one wireless sensor output port 27 for such amplified signal data.

Such an embodiment of measurement sensor 11 may work with an ex vivo measurement control device 12 having a control processor 42, a non-transient control memory 40, a control power supply 52, and a clock 48. Similar to as discussed above with reference to FIG. 5A-C, the control processor 42, control memory 40, control power supply 52, and clock 48 may be in operable communication, whether by direct wiring, circuit board tracing, or otherwise. The measurement control device 12 may have a wireless control input port 47 operably engaged with the wireless sensor output port 27 and adapted to receive amplified signal data from the measurement sensor 11.

Figure 6:
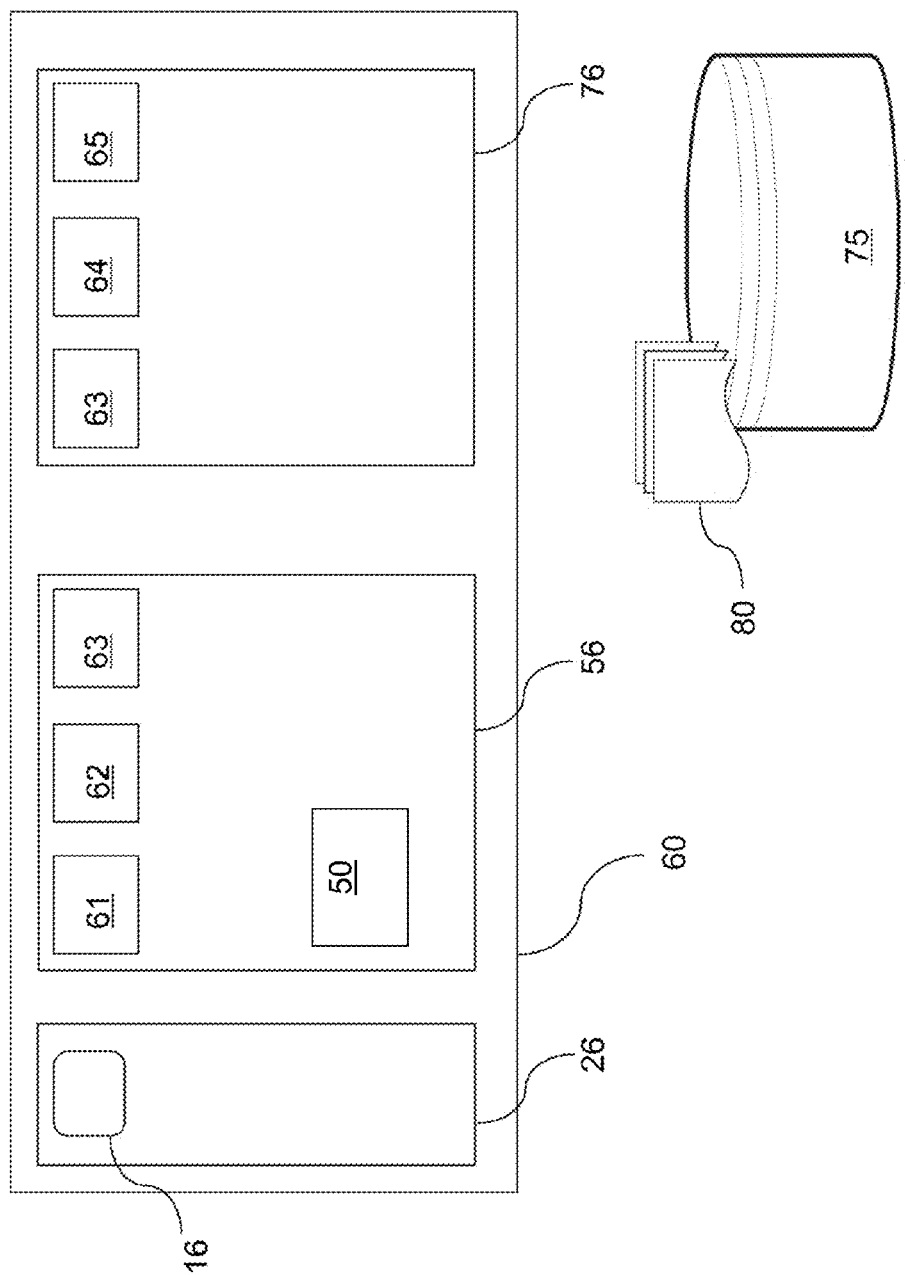
FIG. 6 illustrates an embodiment of computer program code of the system.

The control memory 40 may include control computer program code or software 56 executable by the control processor 42 (FIG. 6). Such control computer program code or software 56 may include a first module 61 for measurement and a second module 62 for data management. The first module 61 may be adapted to receive the measurement sensor identifier 16, the amplified signal data, and a subject identifier and to associate the signal data, sensor identifier 16, and measurement sensor identifier in a record file 80 format, The second module 62 may be adapted to receive the amplified signal data of a record file 80 from the first module 61 and to transmit the amplified signal data to a desired storage, Optionally, the system 10 may include an in vivo measurement sensor 11 with a sensor housing 25 that is substantially tubular, which defines a sensor housing outer surface 25S and a sensor housing length 25L (FIG. 10B). In some such embodiments, the wireless sensor output port 27 may comprise an antenna running substantially along the length 25L of the sensor housing 25, along with supporting transmitters, etc. Substantially along the length simply means by general orientation or along a substantial portion, but it need not extend for the full length or be a straight antenna. It is contemplated, for example, that one embodiment of sensor output port 27 may comprise a coiled antenna oriented along a portion of length 25L, as shown in FIGS. 10A-10B. The anchor 25F may comprise at least one raised ring about a portion of a circumference of the sensor housing 25, which may or may not encircle the full circumference. The at least one raised ring or anchor 25F may disposed on the outer surface 25S and having a height from the outer surface of about 0.1-3.0 mm to anchor sensor housing 25 in place. Other embodiments of anchor 25F may include features such as adhesive, raised ridges, bumps, or eyelets, to minimize movement with respect to a patient or subject 5. Sensor housing 25 may also be provided in other general shapes.

In such an embodiment, optionally computer program code or software 56 (FIG. 6) may further comprise a third module 63 adapted to receive stored data of a record file 80 from the second module 62, to apply such stored data to a predictive model to generate predictive data values over a desired period for such record file as a predictive outcome, and to transmit such predictive outcome to a desired storage. In another option, control computer program code or software 56 may comprise a third module 63 adapted to receive stored data of a record file 80 from the second module 62, to apply such stored data to calculate changes in the amplified signal data over a desired period, and to transmit such changes to a desired storage. In yet another option, control computer program code or software 56 may comprise a third module 63 that is adapted to receive stored data of a record file 80 from the second module 62, to apply such stored data to calculate changes in the amplified signal data from background radiation data over a desired period, and to transmit such changes to a desired storage. In some embodiments, this third module may be adapted to calculate the quality of the radioactive analyte injection, such as to calculate the likelihood of injection infiltration. The computer program code could then transmit the result of this calculation to a desired storage. Additionally, the computer program code could alert the user of the calculation result using visual, audible or other indication means.

In one embodiment, the signal data comprises a plurality of pulses at a pulse frequency over time, and wherein the first module 61 is adapted to communicate a sampling frequency instruction to the sensor processor 22, the sampling frequency instruction being a function of the pulse frequency of the signal data. The first module 61 may be adapted to communicate an increasing sampling frequency instruction upon an increase in pulse frequency.

Processes that could be used in the manufacture of the measurement sensors 11 or other components may include many that are common within the electronics assembly industry, along with the following specific processes. For an embodiment of the system 10 that includes a gamma radiation mask or shield 38, for example, this mask or shield 38 may be glued, molded, swaged, screwed or otherwise mechanically fixed into the measurement sensor housing 25. Then, the mask or shield 38 may be used as a mounting plate for the other measurement sensor 11 components, including electrical components and additional housing components to create a lightproof sensor housing 25. As shown in FIGS. 57 and 58, in any number of embodiments the sensor housing 25 could include structure for placement and alignment of a backscatter material 82.

In another embodiment, the measurement sensor 11 components may be arranged within the measurement sensor housing 25, and then an epoxy, silicone or other curable fluid could be applied surrounding the components. This method would hold the optical components in alignment while also surrounding them with a light proof material.

In another embodiment of the measurement sensor 11 that includes a wireless output port 27 as an antenna, it may be embedded in the structure of the measurement sensor housing 25. For example, antenna wire may be arranged on a mold form, then molding plastic may be applied around the form thus encapsulating the wires. With this method, the antenna wires could be of numerous designs for the optimization of antenna efficiency. Additionally, this method could allow for a ferrite material to be placed within the antenna portion of the housing 25 to further optimize the antenna efficiency.

Figure 11:
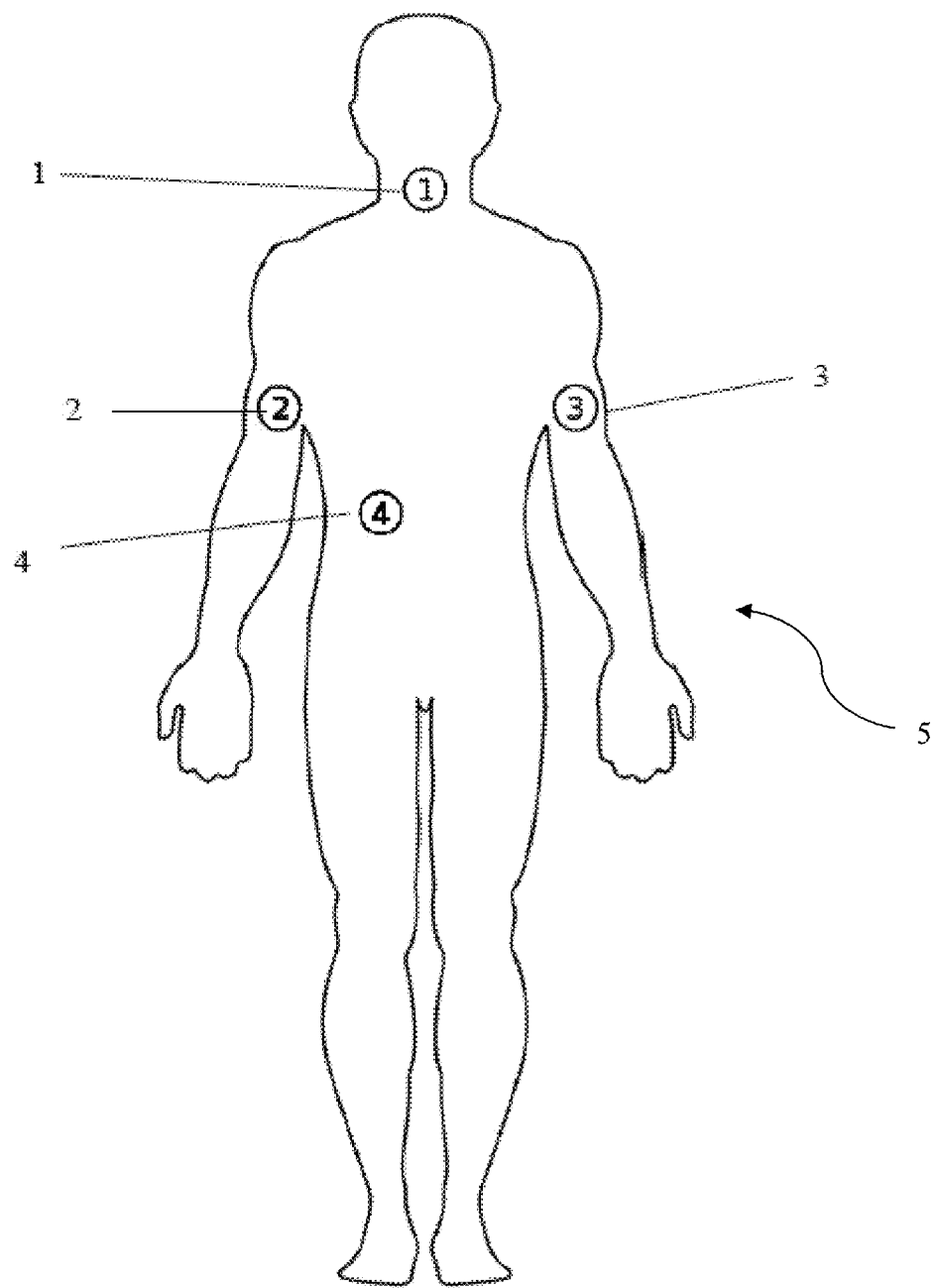
FIG. 11 is a diagram illustrating locations on a subject's body where sensors may be placed.
Figure 12:
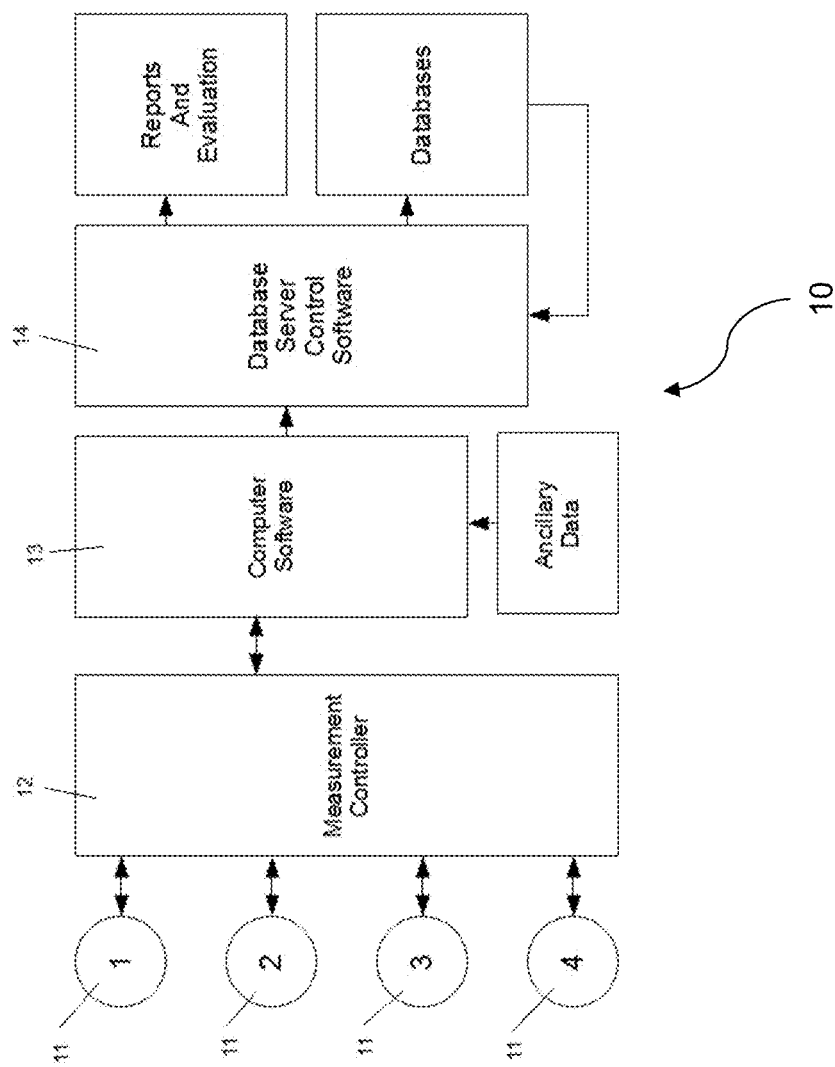
FIG. 12 is a flow diagram of an embodiment of components the system.
Figure 13:
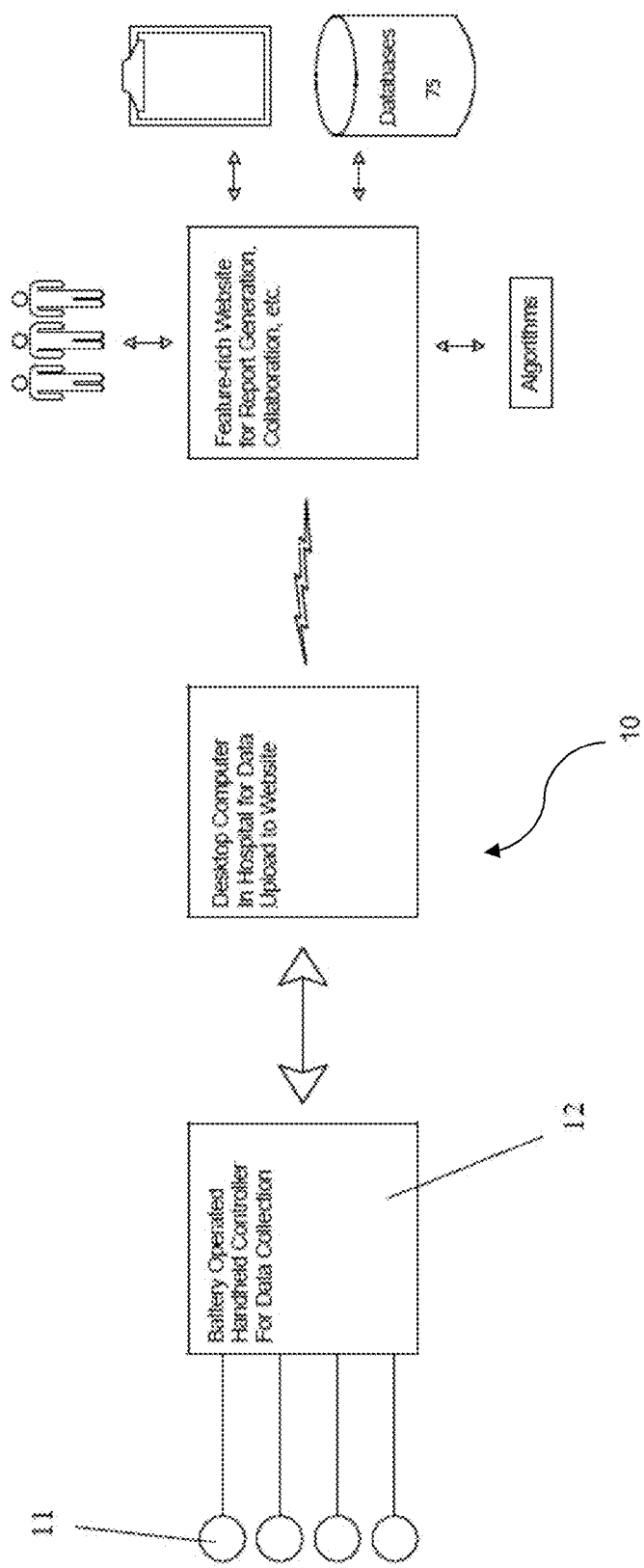
FIG. 13 is a schematic diagram illustrating aspects of an embodiment of the system.

Additional aspects or optional embodiments are provided below. The present system enables (but does not require) radiation sensitive sensors to be placed ex vivo, such as on or near a test subject's skin. These sensors may measure the localized uptake of a radio-labeled tracer which is injected into the subject 5, in an embodiment as shown in FIG. 1, measurement sensors 11 may be placed in one or more of the following locations of FIG. 11, for example: (a) directly over the tumor 1; (b) on the upper right arm 2, approximately 10 cm above the antecubital fossa; (c) on the upper left arm 3, approximately 10 cm above the antecubital fossa, and (d) over the liver 4, immediately below the ribs and directly below the nipple. As shown in FIG. 2, for example, an embodiment of the system 10 may comprise: (i) one or more measurement sensors 11; (ii) a measurement control device 12; (iii) computer software or computer program code 13 capable of executing certain functions, such as measurement and generation of predictive data or assessment as to the likelihood of an injection infiltration. The system 10 may also include a desired storage for data, etc., with appropriate databases, database management or server control software 14, etc.

Figure 14:
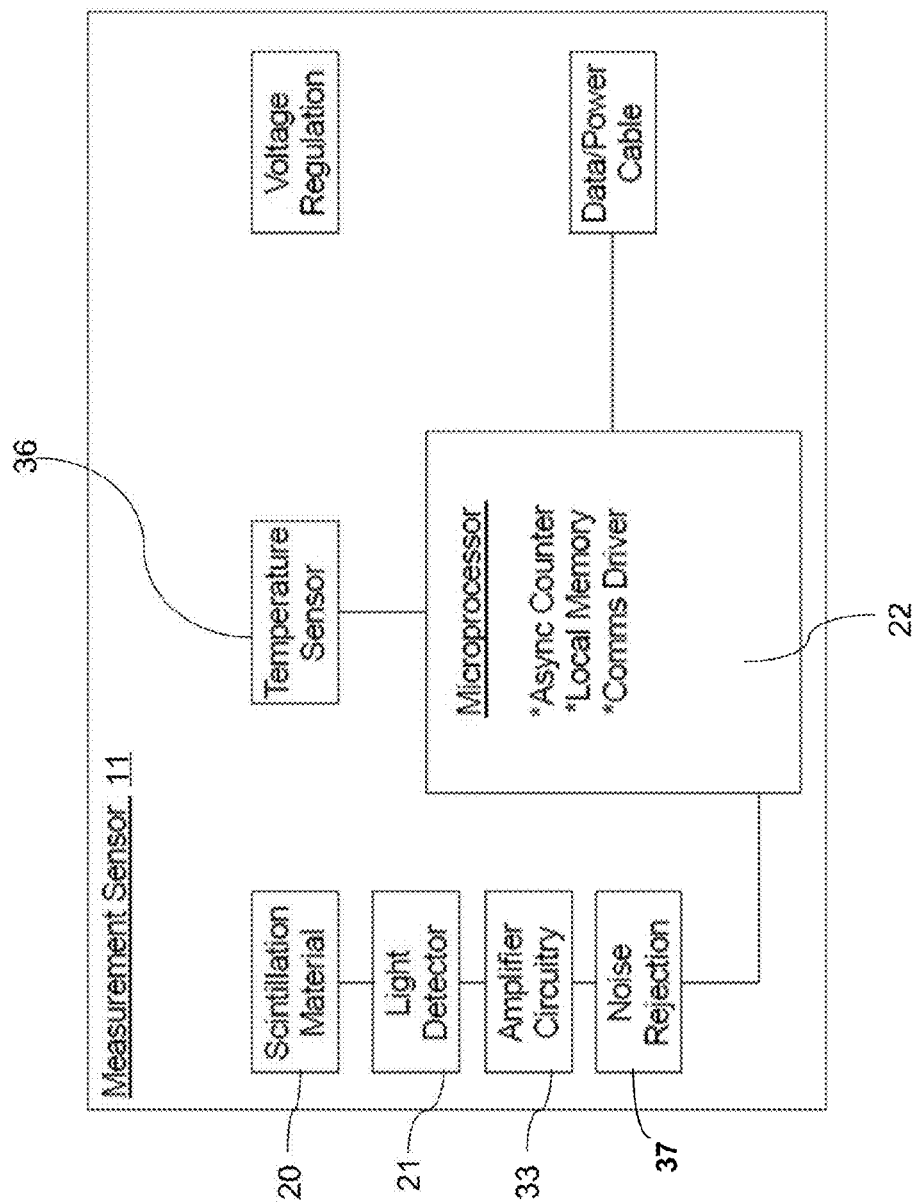
FIG. 14 is a schematic of an embodiment of a measurement sensor.
Figure 15:
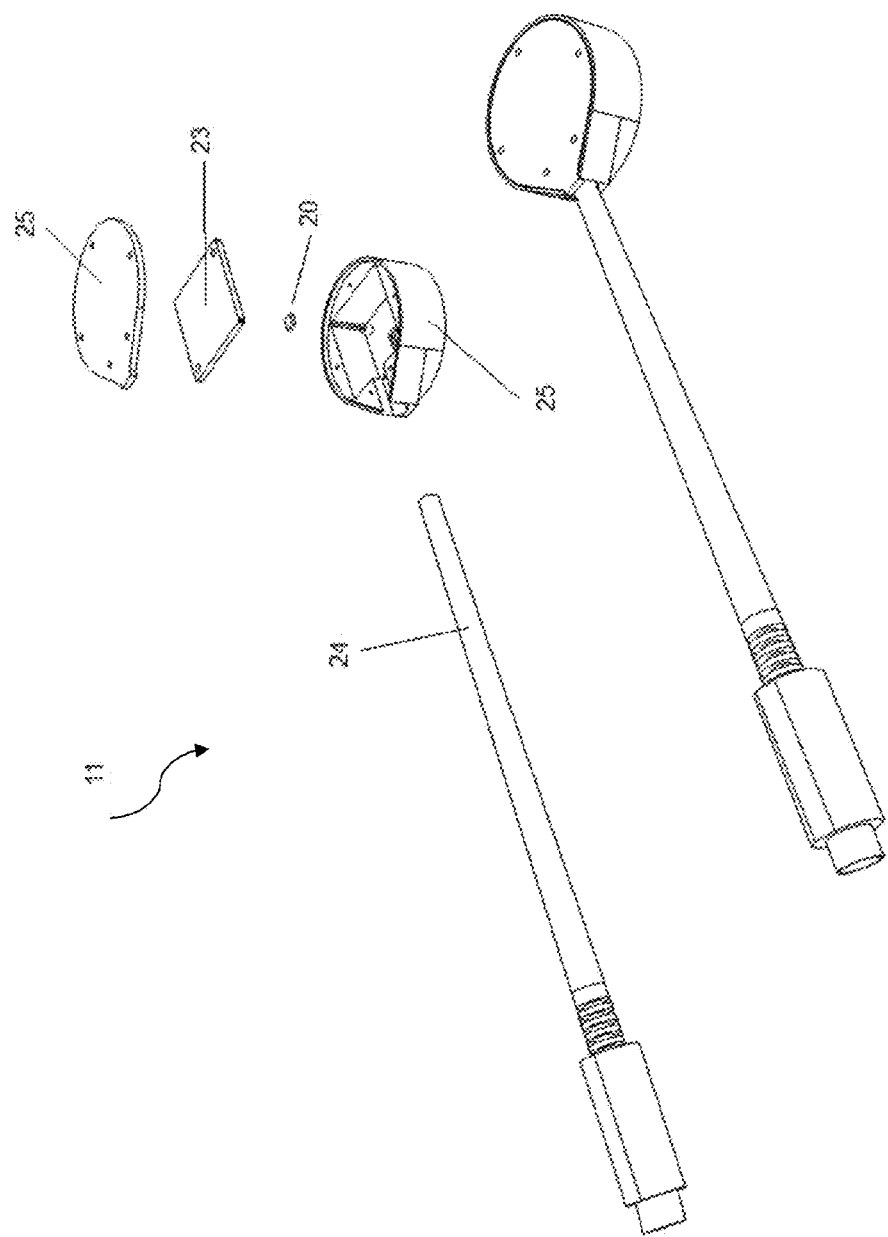
FIG. 15 is a schematic diagram illustrating aspects of an embodiment of a measurement sensor.
Figure 16:
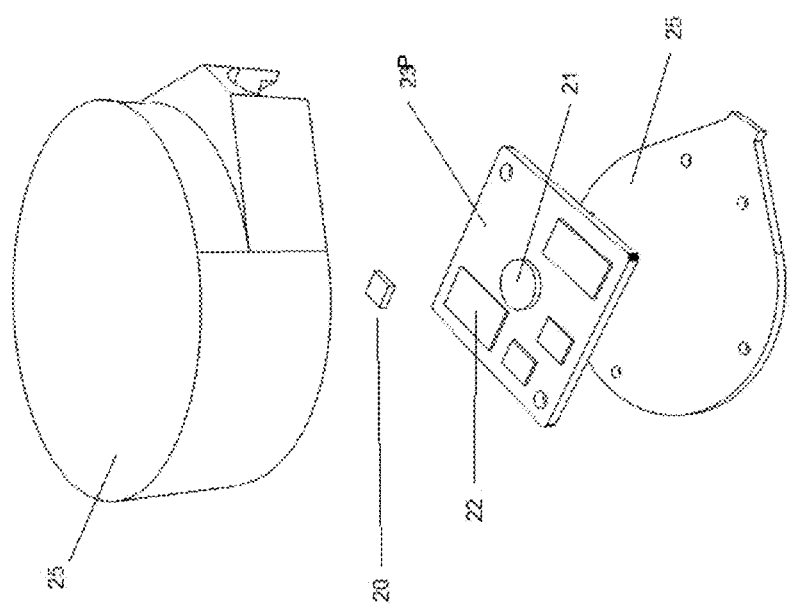
FIG. 16 is a detailed exploded view of an embodiment of a measurement sensor.
Figure 17:
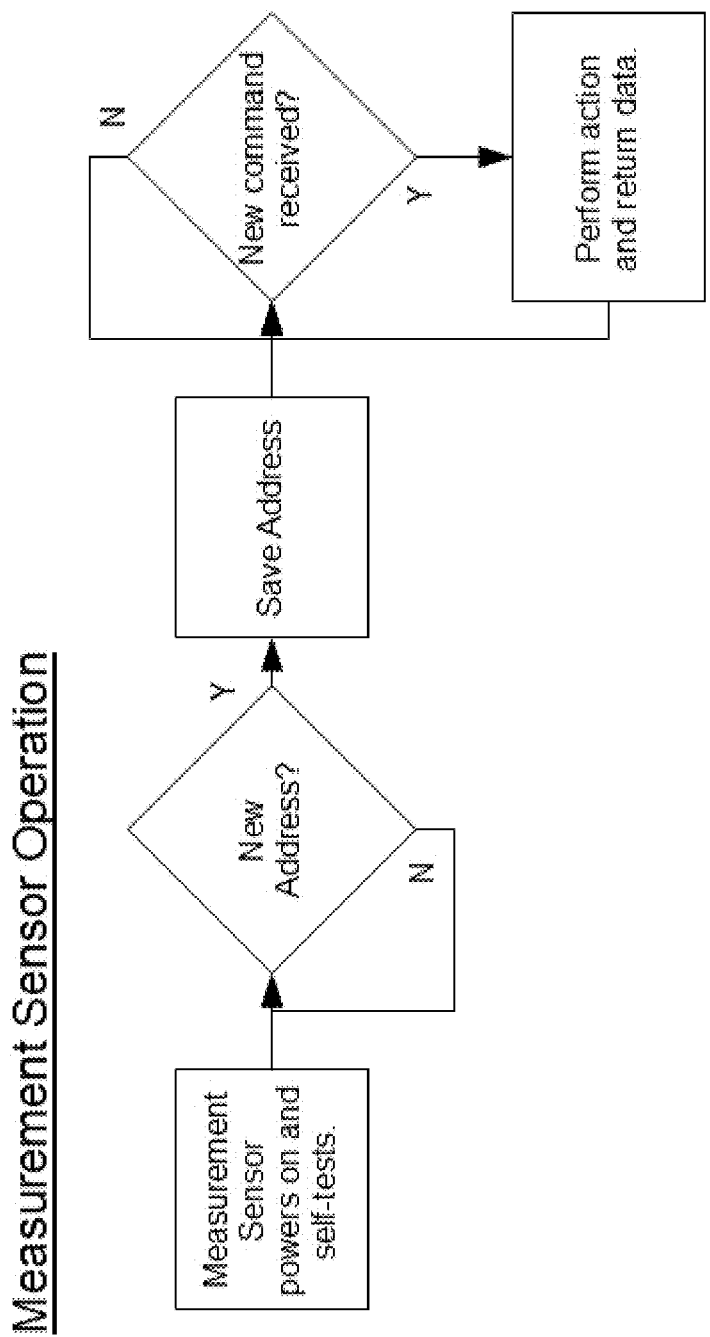
FIG. 17 is a flow diagram illustrating an embodiment of measurement sensor operation.
Figure 18:
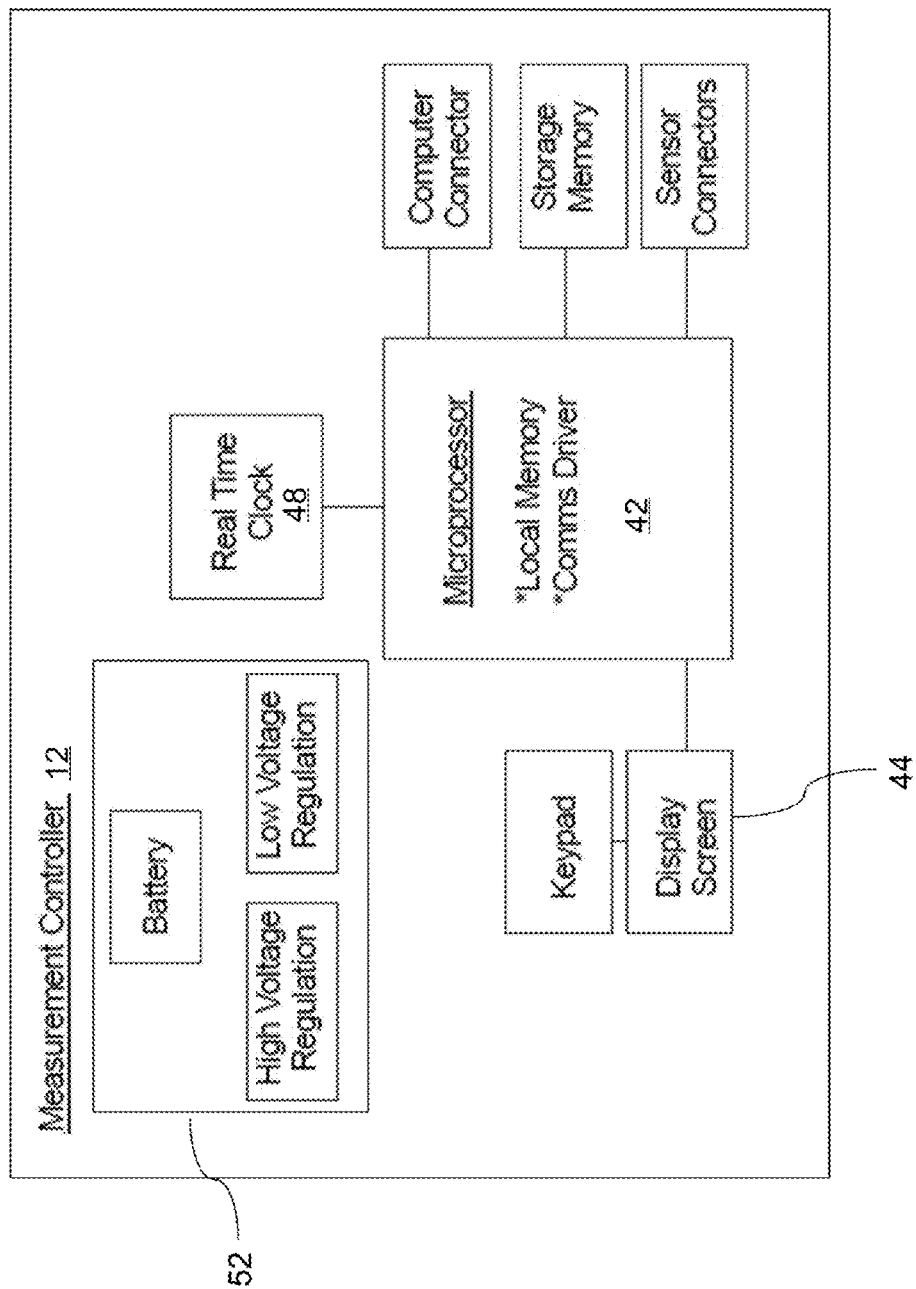
FIG. 18 a schematic diagram illustrating aspects of an embodiment of a measurement control device.
Figure 19:
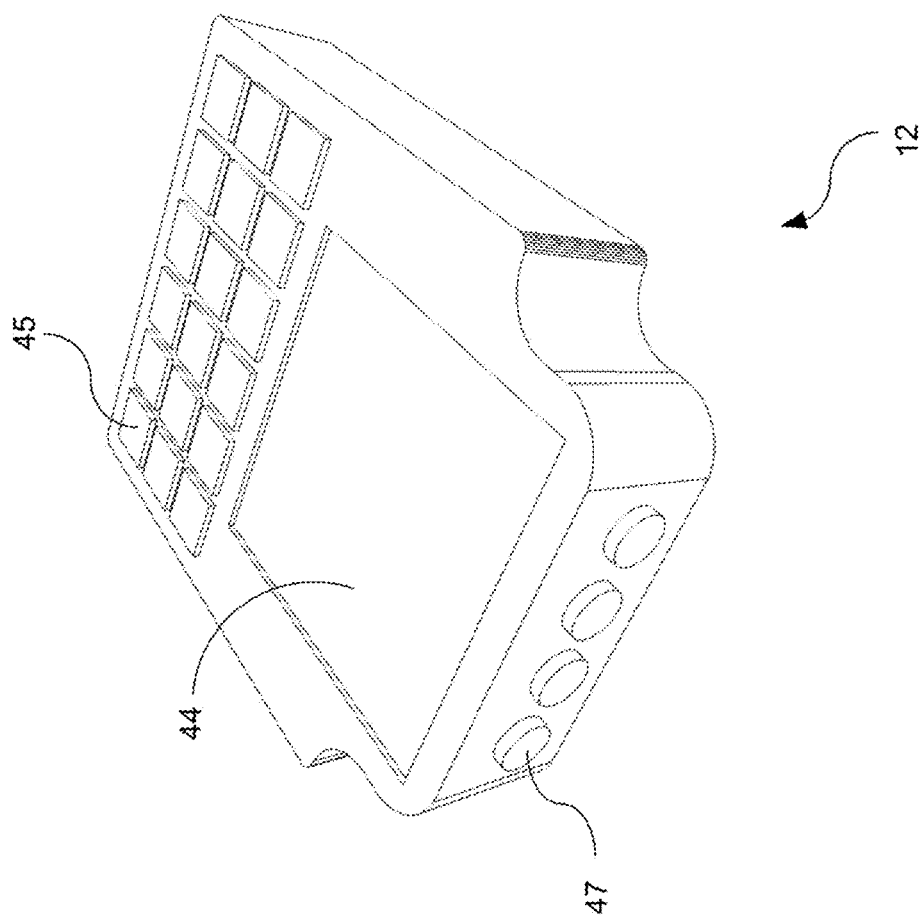
FIG. 19 is a front prospective view of an embodiment of a measurement control device.

As shown in FIGS. 14 through 16, a measurement sensor 11 can be, for example, a device comprising a scintillation material 20; a light detector 21; and a sensor processor 22 with associated non-transient sensor memory 30, logic or sensor software 26, and other circuitry supporting these components in operable communication, optionally with a printed circuit board 23P (FIG. 16). FIG. 17, for example, illustrates a flow diagram of operation of an embodiment of an ex vivo measurement sensor 11. In operation, a subject 5 may receive a systemic or local administration by injection of a radioactive substance (also referred to as a tracer). When this radioactive substance decays, it releases or emits positrons (also referred to as high energy particles). The measurement sensor 11 uses a scintillation material 20 to receive gamma radiation from positron emission decay and to convert the radiation into photons, such as pulses of light, which may then be detected by the light detector 21. The sensor processor 22 may enable measurement and collection of the photons, such as the number of light pulses detected over a given amount of time. For example, a large number of light pulses detected per unit of time may correspond to a large concentration of radioactive material. As the radioactive material concentration changes, the light pulses detected per unit of time changes accordingly. By graphing the light pulses counted versus time of data collection, a visual representation of radioactive concentration over time may be produced. This graph indicates how the radioactive concentration is changing. Optionally, noise rejection 37 (FIG. 14) may comprise a filter for filtering amplified signal data based on the height or amplitude of such pulses. For example, noise rejection 37 may include a voltage comparator or an analog to digital converter with computer program code to compare the digital output to a reference level.

Any number of small embedded processors are adequate for use in the measurement sensor 11, and sensor processor 22 may include a dedicated asynchronous counter of suitable size, if need for the application and if an external one is not included in the additional circuitry. The sensor processor 22 may be embedded in the measurement sensor, or an external sensor processor 22 may be provided as applicable. The sensor processor 22 may be specially configured to satisfy various embodiments of the system 10, depending on the requirements of the application. An FPGA or other programmable logic device, for example, may be well suited to this system, possibly incorporating a microprocessor sub-system within the FPGA design.

Possible scintillation materials 20 include, but are not limited to: Bismuth Germanate (BOO); Gadolinium Oxyorthosilicate (GSO); Cerium-doped Lutetium Oxyorthosilicate (LSO); Cerium-doped Lutetium Yttrium Orthosilicate (LYSO); Thallium-doped Sodium Iodide (NaI(T1)); Plastic Scintillator (Polyvinyltoluene); or Cadmium Zinc Telluride (CZT). In an embodiment of a measurement sensor 11, multiple scintillation materials 20 adapted to measure different radioisotopes may be used. In another embodiment of a measurement sensor 11, scintillation materials 20 that do not require the use of a light detector 21 may be used. In another embodiment of a measurement sensor, multiple scintillation materials 20, each with their own detection circuitry, may be included to enable a two dimensional array of measurements.

In an embodiment of measurement sensor 11, the light detector 21 may include a signal amplifier 33 or amplification circuitry to handle low level signals. In another embodiment, measurement sensor may further include a temperature sensor 36 which is coupled to a temperature compensator 50, the temperature sensor adapted to measure an ambient or local temperature of the scintillation material 20 and light detector 21, and to communicate or report such temperature to temperature compensator 50. Temperature compensator 50 being adapted to generate a temperature correction factor based on comparison of the ambient temperature to a reference temperature. The temperature compensator 50 may apply the correction factor to the signal data to produce temperature compensated signal data, or may be adapted to reporting the local temperatures of the scintillation material 20 and light detector 21. Depending on the embodiment, in vivo detection may not require temperature compensation in that the measurement sensor 11 might be calibrated for normative subject temperatures. Additionally, some embodiments of the measurement sensor 11 could include temperature response calibration, which would nullify the impact of temperature on system 10 operation. This nullification could be accomplished, for example, by measuring the response a sensor 11 has with respect to temperature, and then modifying the parameters of amplifier 33 or other circuit components so as to counteract this temperature response.

In another embodiment of the system, a measurement sensor 11 can be, for example, a device comprising a scintillation material 20; a light detector 21 and associated signal amplifier 33 or amplification circuitry and sensor processor 22 located on a printed circuit board 23P in the sensor portion of the system. Light detector 21 may be selected based on the application, such as a photodiode or photocathode, and signal amplifier 33 (or amplification circuitry, possibly incorporated into circuit board 23P) may include a photomultiplier or simply a signal amplifier 33. Other associated circuitry may then then moved to the measurement control device 12. In any number of embodiments, the measurement sensor 11 can be provided with microelectromechanical machine (MEMS) power generation capability such that a battery or external power source is not necessary, A MEMs generator may be piezoelectric based, adapted to generate electricity from a motion of the subject 5, body heat of the subject 5, or the blood pressure of subject 5. Alternatively, sensor power supply 32 may be a corded power connection to either the control device. In another embodiment, a measurement sensor 11 can be a wireless, with an independent power supply 32.

In an embodiment of a measurement sensor 11, for example, the electronics may be enclosed in a light-proof enclosure or housing 25 and there can be a multi-conductor cable 24 for data communications. Mechanical design of the housing 25 can be used to accurately control the placement of the scintillation material 20. As shown in FIGS. 57 and 58, in any number of embodiments, the sensor housing 25 could include structure for placement and alignment of backscatter material 82.

In an embodiment of a measurement sensor 11, the sensor may include sensor housing 25 which optionally may incorporate a shielding mask 38 for collimation of the incoming radiation for increased directional sensitivity or a backscatter material 82 for the reflection of incoming radiation which is not captured by the scintillation material 20. The shielding mask 38 can be made of any number of dense materials including, but not limited to lead, steel, iron, aluminum, iridium, platinum, copper, cement, dense plastic, etc. The shielding mask 38 can be tailored to protect against specific radiation depending on the application of the system of the present invention. As described above, sensor housing 25 may include structure for the placement and alignment of backscatter material 82.

In an embodiment of a measurement sensor 11, for example, the sensor could further include a removable and/or disposable protective sleeve or case, also referred to as carrier 35. This sleeve or carrier 35 can have adhesive (e.g., adhesive 35A) applied in order to attach the measurement sensor 11 to a test subject 5. This sleeve can also be used as a sanitary barrier between the measurement sensor 11 and a test subject 5. In some embodiments, measurement sensor 11 may further include housing 25 which itself has adhesive used to attach the sensor 11 to a test subject 5. Some embodiments of sensor 11 may include structure for attachment, such as an arm band, to the arm of a subject 5. Such an arm band may include hook and loop fasteners or other approaches of securing to subject 5. An embodiment may include a pocket or other structure by which sensor 11 is secured to the attachment structure or arm band.

In any number of embodiments, measurement sensor 11 and measurement control device 12 may include the necessary hardware and software to enable wireless communications between them. In such an embodiment, encryption techniques may be used to provide security for wireless signals.

In any number of embodiments of the system of the present invention, an individual measurement sensor can be calibrated for radiation sensitivity. This calibration can overcome measurement inconsistencies due to manufacturing and physical tolerances in the sensor. Since each measurement sensor 11 has unique manufacturing and physical tolerances and material characteristics, no two sensors will naturally report the same measurement given the same radiation source input. Therefore, each sensor may be exposed to a known activity radiation source and a correction factor can then be provided for each individual sensor. As a result, each measurement sensor 11 used in the system 10 may be calibrated with one another with regard to radiation sensitivity.

In any number of embodiments, an individual measurement sensor 11 may be calibrated for temperature sensitivity. Various components of a measurement sensor 11 are sensitive to temperature changes and the repotted radiation activity due to temperature. It is known that a scintillation crystal or material 20, a light detector 21, and, to a lesser degree, amplifiers used for light detection, for example, may be sensitive to temperature. Therefore, a precision temperature sensor 36 may be placed locally or proximally to the temperature sensitive elements. Ambient temperature can then be recorded during the data collection process so that corrections or compensation can be made to signal data or measurement readings in order to compensate for any inaccuracies in the measurement readings resulting from certain elements' sensitivity to temperature, producing temperature compensated signal data. In order to determine temperature correction factors, a measurement sensor 11 may be subjected to a stable radiation test source while the surrounding temperature is swept through the range of the operating temperatures. This may be accomplished in a laboratory temperature chamber. Through this test process, radiation activity of a known, stable source as well as temperature data can be recorded. A calibration curve can then be calculated which adjusts the measured radiation activity to a normalized flat response corresponding to expected compensated signal data, Additionally, some embodiments of sensor 11 may include temperature response calibration, which could nullify the effect of temperature on system operation. Nullification may be accomplished by measuring the response a senor 11 has with respect to temperature, and then modifying the parameters of amplifier 33 or other circuit components to counteract this temperature response.

In another embodiment, a measurement sensor 11 may provide adaptive performance and measurement capabilities. For example, if the rate of tumor growth accelerates, the sensor can automatically respond to the change by increasing sampling frequency.

In any number of embodiments of the system, a measurement control device 12 can be, for example, a hand-held and battery powered device comprising a display screen, a keypad and data communications connectors. An alternative embodiment may include the measurement control device 12 and one or more sensors 11 contained within the same housing, and operably engaged with wires, printed circuit board traces etc. In an alternative embodiment of the system of the present invention, the measurement control device 12 can be a desktop-style powered device. In another embodiment, the measurement control device 12 or other portions of system 10 may include a cradle-style charging dock for the battery operated device. The cradle-style charging dock can charge batteries for a hand-held device and can also initiate the capture of any measurements in the hand-held device's memory. In another embodiment, the measurement control device 12 may provide MEMS power generation capability such that a battery or external power source is not necessary.

Figure 20:
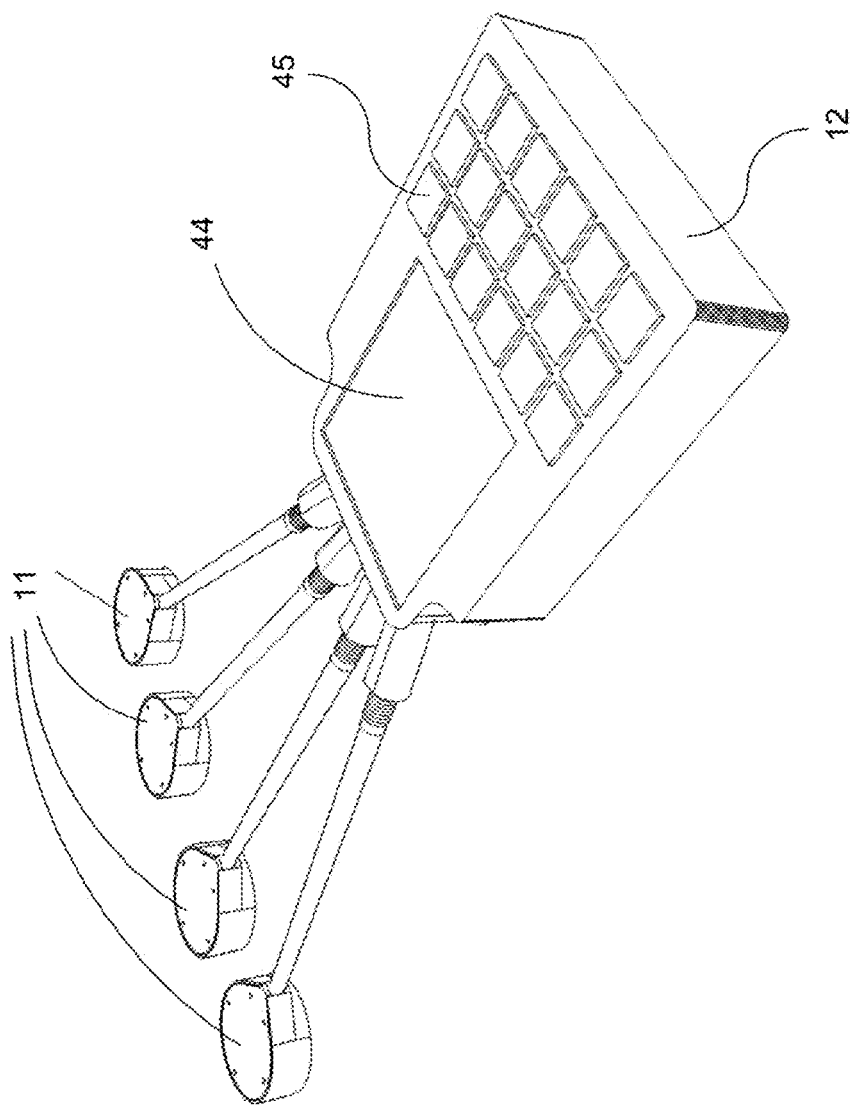
FIG. 20 is a front prospective view of an embodiment of a measurement control device with measurement sensors attached.
Figure 21:
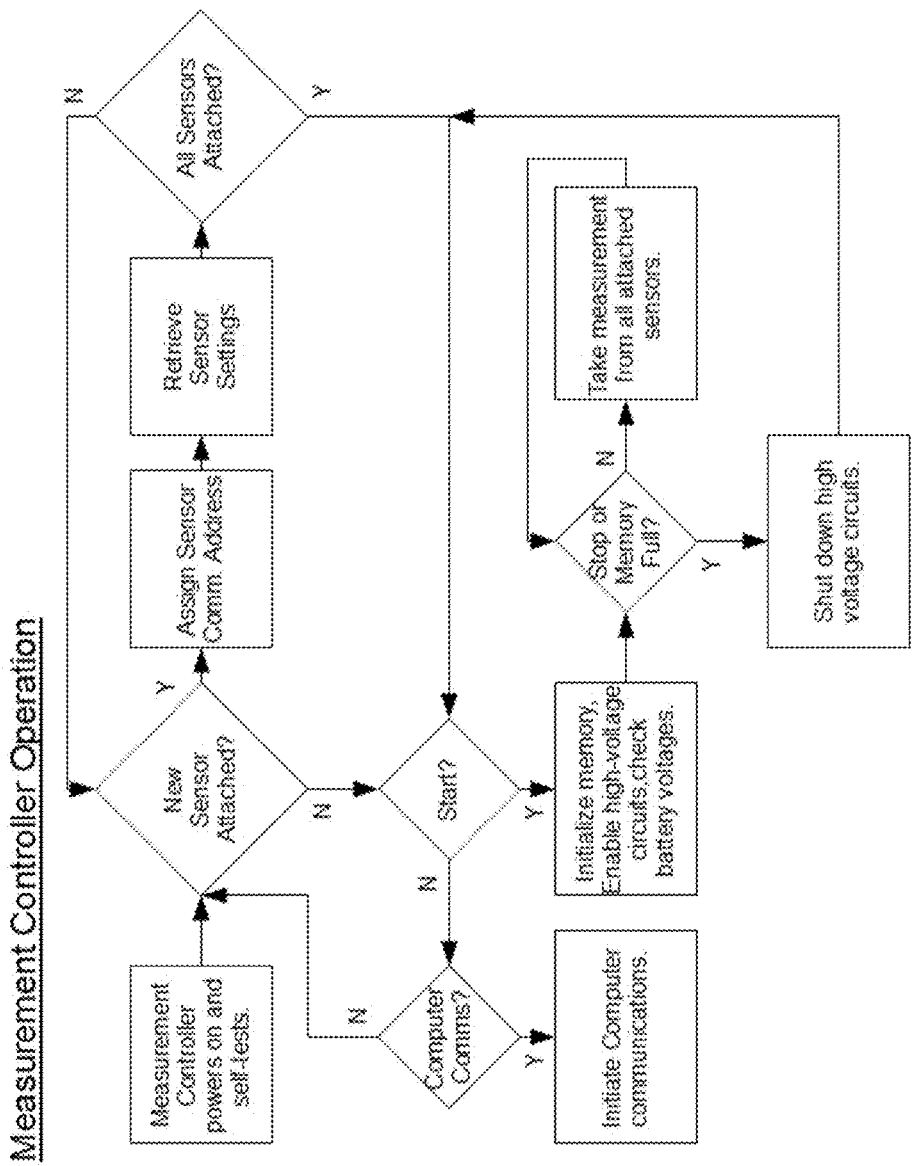
FIG. 21 is a flow diagram illustrating measurement control device operation in an embodiment.
Figure 22:
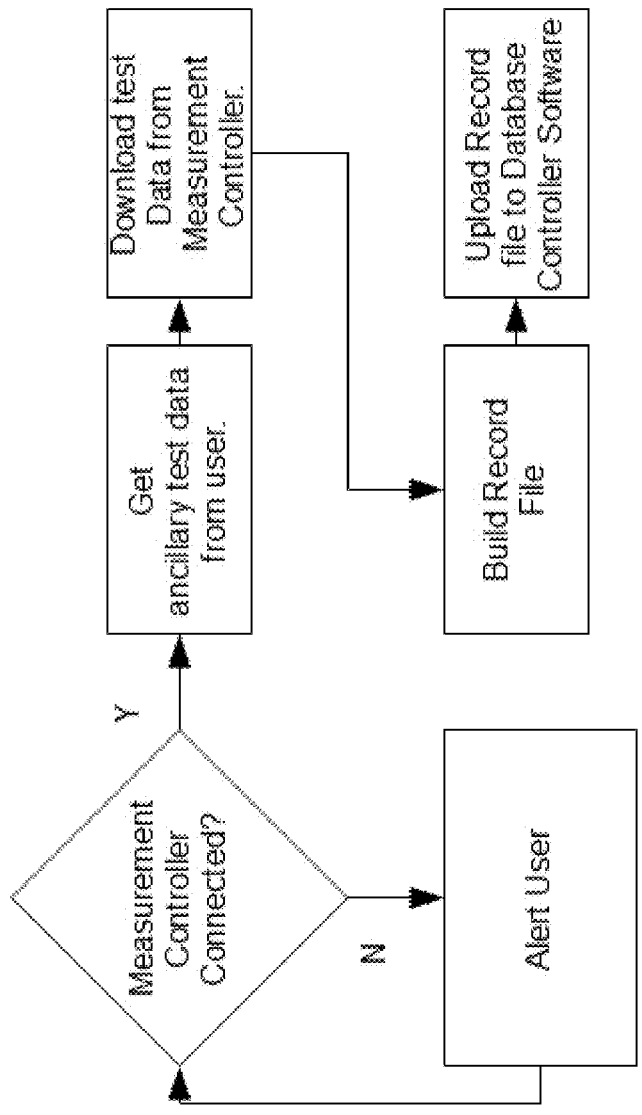
FIG. 22 is a flow diagram illustrating computer software operation in an embodiment.
Figure 23:
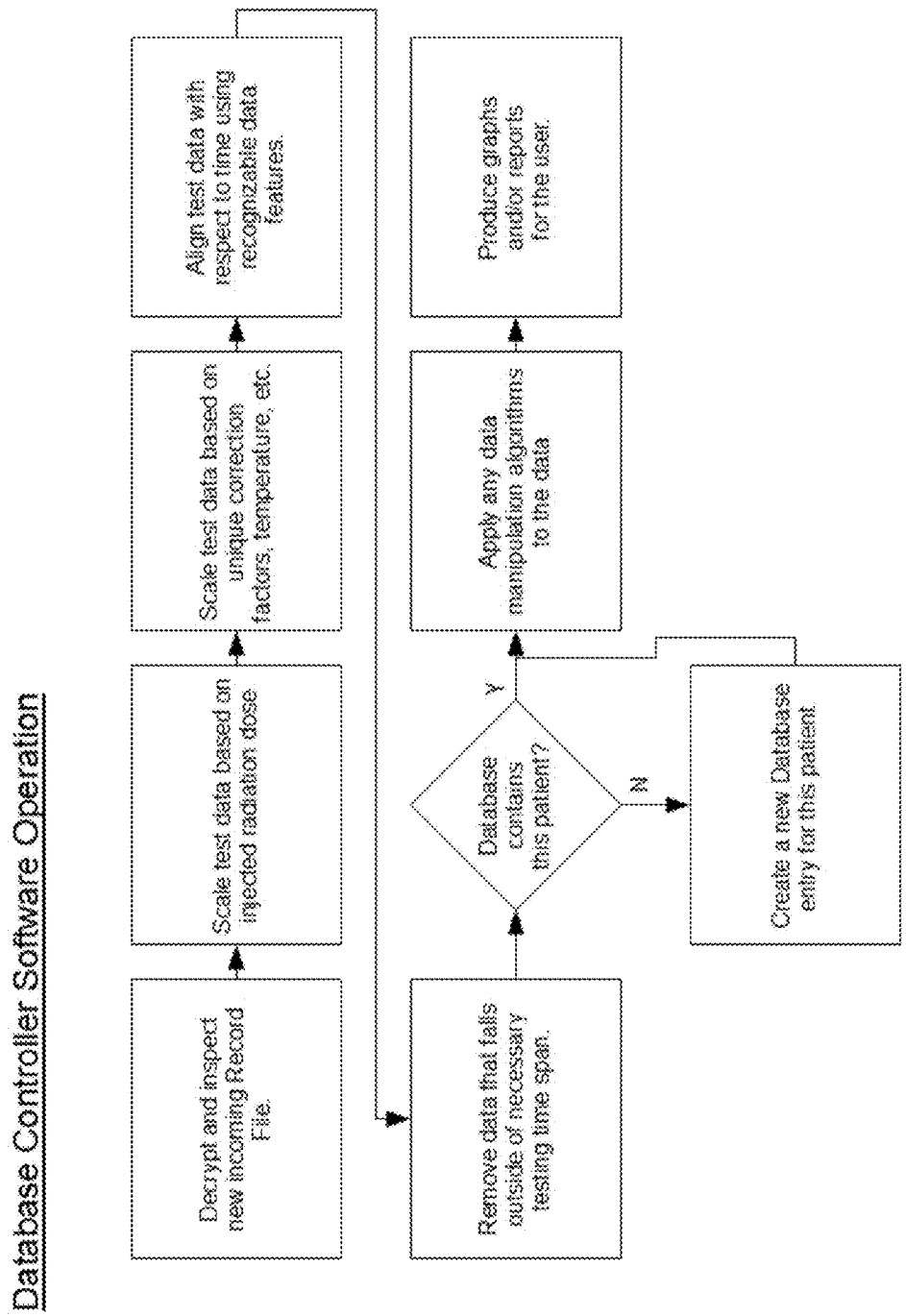
FIG. 23 is a flow diagram illustrating database controller software operation in an embodiment of the system.

In any number of embodiments of the system 10, as shown in FIGS. 20 through 21 for example, a measurement control device 12 comprises a control processor 42, control software 56 (optionally as embedded software), control memory 40, a real-time clock 48, and other associated logic and circuitry on a printed circuit board. The control processor 42 may be embedded in the measurement control device 12, provided as an external processor, or optionally merged with station 70. The control processor 42 is generally specially configured to satisfy embodiments of the system 10. The control device can control user-interface, data collection, and data transmission activities. There are various microprocessors capable of this including small embedded processors and single-board computers. FIG. 21 is a flow diagram illustrating operation of an embodiment of a measurement control device 12. The system 10 generally may respond to user input, keep track of sensor attachment or association, monitor operational parameters, such as battery level, and transfer measurement data to a desired storage, such as an external computer. In an embodiment of a measurement control device 12, as illustrated in FIG. 20 for example, there can be multiple data communications connectors to enable the attachment of multiple measurement sensors 11, as well as a data communication to a variety of desired storage devices or networks.

In an embodiment of a measurement control device 12, the device can further include network connectivity and control hardware and software to incorporate the functionality of the control computer software 56. This creates a stand-alone system at the test site which eliminates the need for a separate computer or computer software. Encryption and decryption methods known in the art can be provided in any number of embodiments to secure wireless communications.

An embodiment of a measurement control device 12 may further include a bar code scanner for recording pertinent identification numbers, calibration codes, etc. when printed on bar codes. An embodiment of a measurement control device 12 can further include a pulse-oxygen, skin resistivity, or other biological sensor in order to incorporate additional data into the measurements collected. Another embodiment of a measurement control device 12 can further include a digital camera system for incorporating photos into the data record tile. These photos could be used for sensor placement details, for example. One embodiment of a measurement control device 12 can further include functionality which communicates to the user specific details pertinent to the test or test subject being worked with. This communication can include, but is not limited to, non-standard placement locations for the measurement sensors 11, reminders of tumor size and location, general notes, test related photos, etc.

In an embodiment of a measurement control device 12, for example, a power switch can control power to all components of the device, except possibly a real-time clock 48. The clock 48 may have consistent hack-up power to avoid losing the programmed date and time. When the power switch is in the "ON" configuration, power may be applied to the device components, and a microprocessor can start operation and test operability. The microprocessor of control processor 42 may further test external peripherals such as the display 44, the real-time clock 48, etc. As the tests are performed, a display screen of the measurement control device 12 may display, for example, a waiting message. Next, at least one measurement sensor 11 may be attached to the control device 12 via a connector and a cable, such as multiconductor cable 24. Upon attachment of a measurement sensor 11, the control device 12 recognizes the attachment and performs duties described below to start up the measurement sensor 11.

In an embodiment of a measurement sensor 11, for example, power may be supplied to the sensor via the measurement control device 12. For example, a multiconductor cable 24 with a connector on the end or a plug that fits into a mating jack can be used to connect the measurement sensor 11 to the control device 12. Power can be supplied to the measurement sensors 11 over this cable from the measurement control device 12. The sensors can be connected to the measurement control device 12 before data collection and remain connected throughout data collection. In another embodiment, the measurement sensor 11 may include its own sensor power source 32 and non-transient sensor memory 30 to store recorded data such that no cable might be necessary and the sensor does not need to remain connected to the measurement control device 12 during operation. In order to retrieve the recorded data, wireless communications may be enabled and/or a cable may be connected to the measurement control device 12 at a desired time.

After power is turned on to the sensor 11, as shown in FIGS. 17 and 21 for example, the sensor processor 22 may start operation and test itself. If the self-test verifies that the measurement sensor 11 is operational, the sensor can alert the measurement control device 12 that the measurement sensor 11 is operational and ready to receive an address which is an address that the control device 12 will use to communicate with the identified measurement sensor 11. The measurement control device 12 can next send the measurement sensor 11 a unique address or identifier 16 assignment (i.e., unique being sufficiently individualized for the application to avoid confusion). After receiving the unique identifier 16 assignment, the measurement sensor 11 can accept the unique address and listen to a communications bus for commands specific to the individual sensor. A measurement control device 12 may send any of the following commands to any of its connected sensors: (1) connection check using the sensor's unique address; (2) Sensor LED on/off; (3) Set sensor PWM output; (4) Read/Write sensor EEPROM; (5) Measure Temperatures; and/or (6) Measure Radiation pulses for a set time period (for example, one second). Other commands not specifically listed can be sent by the measurement control device 12. After the measurement control device 12 sends a command to the measurement sensor 11, the sensor performs the commanded action and replies with a result if necessary.

In any number of embodiments of the system, when one or more measurement sensors 11 are attached to a measurement control device 12 and the sensors are operational, the measurement control device 12 can indicate, through a message on the display screen, for example, that the device is ready to begin data collection. When a user begins data collection, the measurement control device 12 first downloads each sensor's individual calibration data and stores the calibration data into control memory 40 or other desired memory or storage. The control device 12 can then request for a measurement of temperature and radiation pulses, for example, from each attached measurement sensor 11. All received readings can be stored, along with a time stamp, in the control memory 40, When the control memory 40 might be full or if the user stops the data collection, the measurement control device 12 may simply stop accepting readings from the measurement sensors 11. A user may download the saved data collected from the control memory 40 to a computer or other desired storage.

In any number of embodiments, computer program code used in the system may be capable of: (1) performing diagnostic tests on the measurement control device 12; (2) transferring measurement data from the measurement control device and saving it to a record file; (3) gathering ancillary test data from the user or other sources (radiation dose administered, test subject weight, PET scan data, etc.) and including it in the data record file; (4) transferring the data record file to the database server control software; and (5) calculating the likelihood of an improperly performed radioactive analyte injection and reporting or displaying the same to a user, whether by audible, visual, or other signal. In any number of embodiments, database server control software can accept incoming data record files from the computer software and apply one or more algorithms to the data received. Measurement data may be stored in an optional central database 75 while the algorithm output can be used to generate reports for the user. These reports can indicate estimated parameters or even estimated future parameters of a tumor.

In an embodiment of the system, for example, a user may attach a measurement control device 12 to a computer and run computer software to transfer measurement data stored on the measurement control device 12 to the computer. The computer software or program code communicates with the control device 12 to determine what type and how much data is available for downloading. The computer software can ask the user for pertinent test-related information such as radiation dose administered, identification or number of test subject 5, placement locations of the sensors, tumor location and type, etc. Once measurement data has been transferred from the measurement control device 12 to the computer, a data record file can be built. Once complete, the data record file can be transferred to a database server and predictive model or algorithm system.

In any number of embodiments, pre-processing operations may be performed on a test subject data set. Session measurements for all channels can be normalized with respect to injected radiation dose, for example. The dose is recorded during the test and is used to adjust measurements on a scalar basis. A session is one specific data recording event which includes sensor placement on the subject 5, injection of radioactive material, and collection, recordation and transfer of recorded data. Measurements from each session can be aligned so that the rising edge on a "trigger" channel—right or left arm—is at time zero. The term "trigger" channel is used to mean a sensor that is sure to see a large amount of radioactive material so that it is ensured to have a dramatic and easily recognizable increase in the measurement. Having a rapidly changing "step" like this allows for time-alignment of data sets recorded at different times or "sessions." Any data which is before a predetermined time or after the predetermined time (for example, data before time −120 seconds or after time 3600 seconds) can be removed from the measurement data. In addition, session measurements for all channels can be normalized with respect to temperature sensitivity. Individual sensor's temperature correction coefficients can be retrieved and used to correct the radiation pulse count measurements.

In any number of embodiments of the system, session measurements for all channels can also be adjusted to account for the natural decay of the radioisotope used, for example. The radioisotope naturally decays in the test subject and this adds a decreasing function to the measurement data. Accounting for this natural decay and removing any data attributed to the natural decay can portray the data as the amount of radiation encountered without the decay function included.

In any number of embodiments of the system 10, measurements may be aligned with respect to the control channel(s). Control channels are stable and repetitive, therefore aligning all channels will make differences in the non-control channels visible.

In one embodiment of the system 10, a database server and predictive model may be provided. A hardware server which runs software to incorporate incoming data record files from the computer software and to save this incoming data to a database file along with data previously saved; and database server control software. FIGS. 14 and 15, for example, illustrate flow diagrams of operation of an embodiment of the computer software and the database server control software respectively. The database server and predictive algorithm system or model can apply one or more algorithms to this saved database in order to estimate parameters specific to the tumor under test or a group of tumors. Additionally, the database server control software can apply one or more models or algorithms in order to predict future parameters of the tumor or a group of tumors. The database server control software can also use the output of the algorithms to generate report files for the user which present the estimated and/or predicted parameters.

In an alternative embodiment of the system 10, a database server and predictive model comprises a dynamic website with server software running behind it, which allows for a multiple-user system for analysis and reporting. In another embodiment, the database server and predictive model or algorithm system further includes functionality which transfers the algorithm output and report back to the computer software for analysis and interpretation by the user. In one embodiment, the database server and predictive model further includes functionality which can provide real-time communication and updates about sensor data; notification parameters (e.g., situations with tumor development); and/or alert conditions.

In an alternative embodiment of the system 10, database server control software keeps a database of all measurement data that has been submitted previously. Any new data record files that are submitted can be added to the database. The user can include other data records such as, but not limited to, results from other tests (PET Scan, CT Scan, etc.), information about a particular subject (height, weight, etc.), or general notes, for example. The user can use the database server control software to generate graphs of measured data, to calculate various functions of the measured data and then graph those functions if necessary; and/or to apply prediction algorithms to the data. The prediction model may be capable of, although not limited to: (1) predicting the future outcome of tumor treatments; (2) predicting which tumor treatments have the best chance of success; (3) predicting the likelihood that metastatic disease is present in the subject; and/or (4) other. The database server control software can generate reports for the user of measured data and/or predictions based on the data. These reports include, but are not limited to, graphs, predictions with confidence levels, etc.

In any number of embodiments of the system of the present invention, the class of algorithms used is of the classification structure in machine learning. These algorithms use a training set of data to build a model of the data. Then, when new unknown data sets are introduced, the algorithms can determine where in the model the new data should fit. This approach allows for the system of the present invention to inspect a submitted data set and determine whether and how closely it has seen examples like the submitted data set in the past. If there have been similar examples in the past, the system can predict the outcome of the current data set based on the outcomes of the past data. For example, if there are various past examples that closely match the new data submitted, the algorithm can determine which treatments in the past led to the most favorable outcome. Physicians may then select treatments with the best outcome. In another embodiment, the algorithms can provide adaptive performance and measurement capabilities. For example, if the rate of tumor growth accelerates, the system can automatically respond to the change by increasing sampling frequency.

In an embodiment of the system 10, the ways in which new data submitted is matched to previously seen data or determined not to match any of the previous data are based on multiple mathematical or quantitative functions that can be applied to measurement data. For example, area under the curve, polynomial curve fit to a portion or all of the data, the ratio of two data measurement channels, etc., are all ways in which data sets can be matched.

Figure 27:
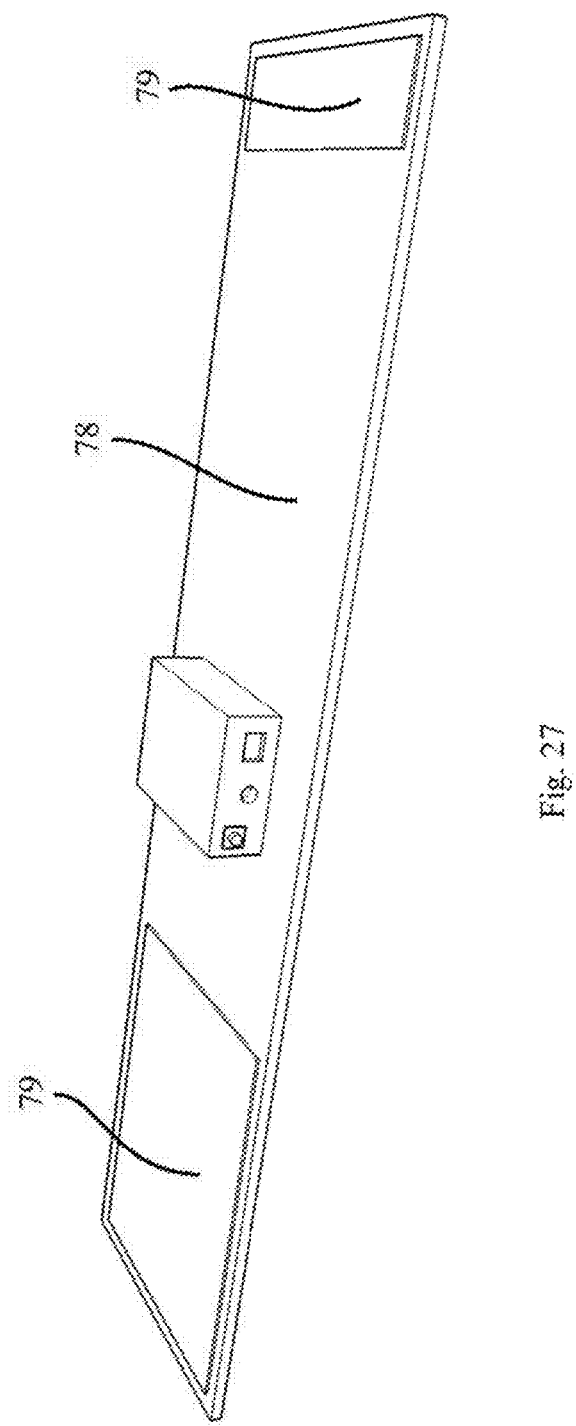
FIGS. 27 and 28 shows an embodiment of a combined measurement sensor and measurement controller, along with an embodiment of an arm band.
Figure 28:
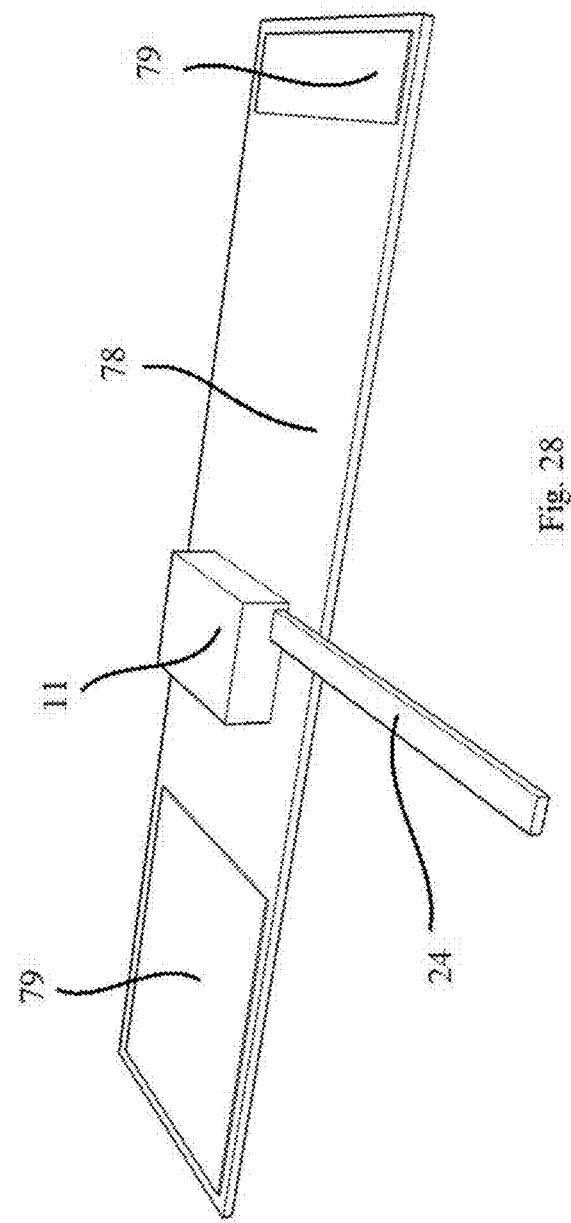
Figure 29:
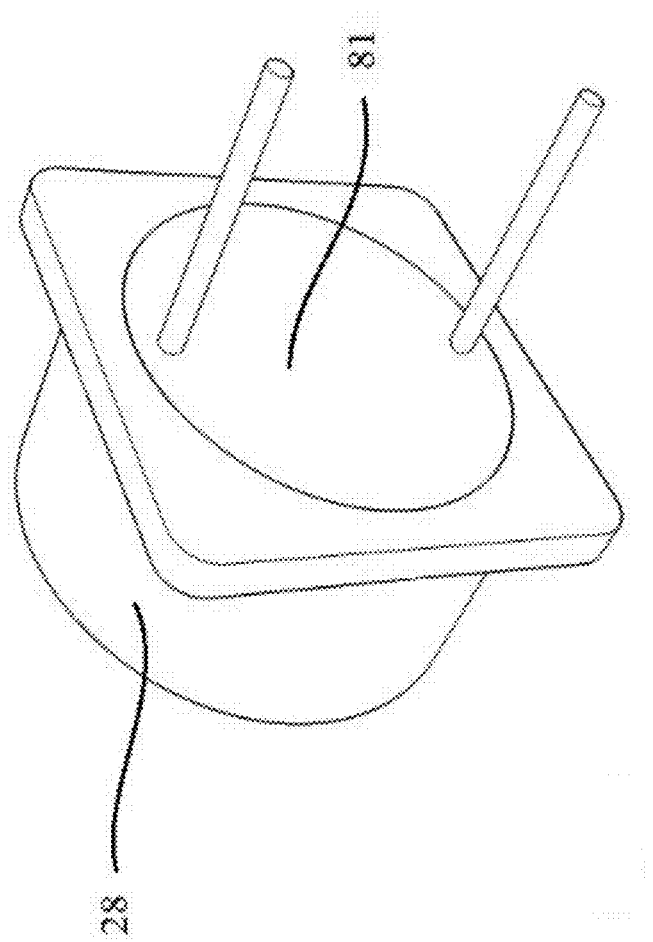
FIG. 29 shows an embodiment of a light shield.

Returning to the figures. FIG. 27 illustrates a detail of an embodiment highlighting arm band 78, with fasteners 79, such as hook and loop fasteners. Such an embodiment may combine measurement sensor and controller on arm band 78. FIG. 28 is another embodiment combined with arm band 78, with measurement sensor 11 and cable 24. FIG. 29 illustrates a detail of light shield 28 with light shield sealant 81.

Figure 30:
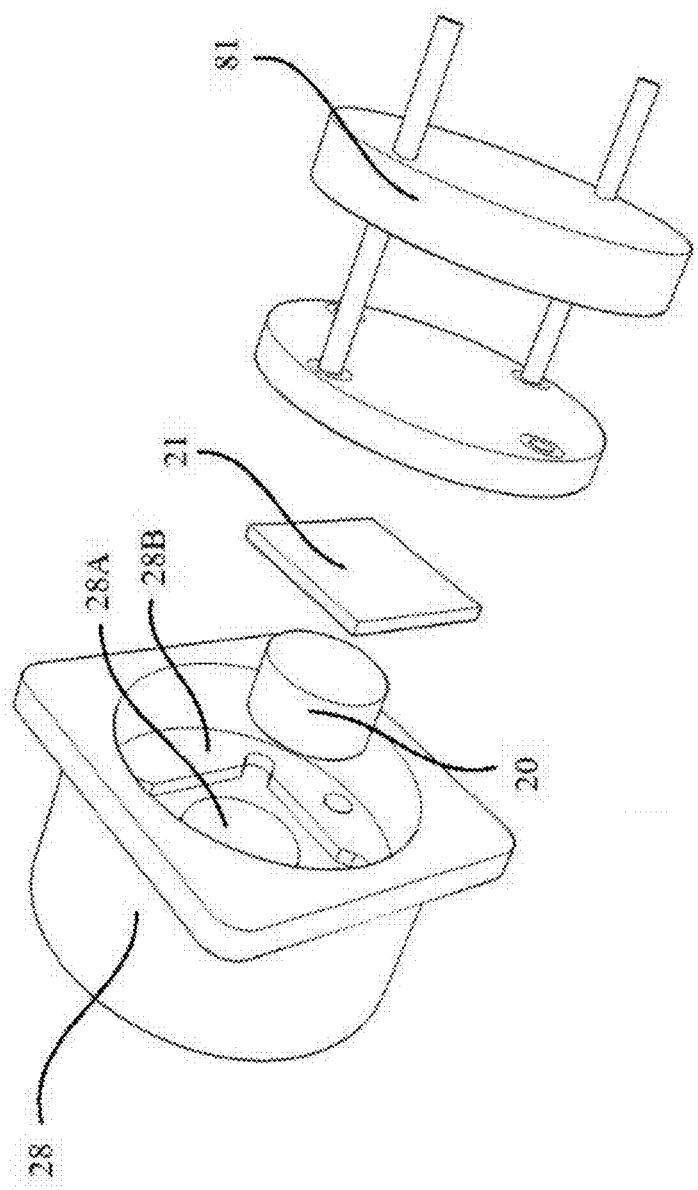
FIG. 30 shows an exploded view of an embodiment of a light shield and the internal components that are being shielded from light.
Figure 31:
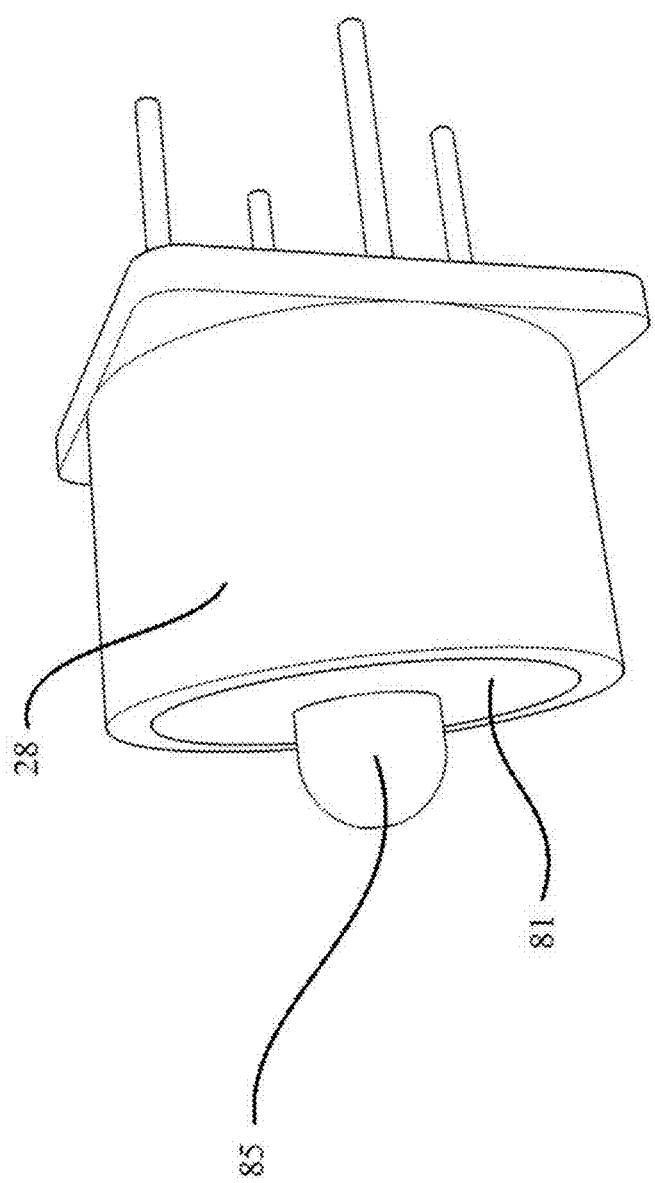
FIG. 31 shows an embodiment of a light shield combined with an alignment light source.
Figure 32:
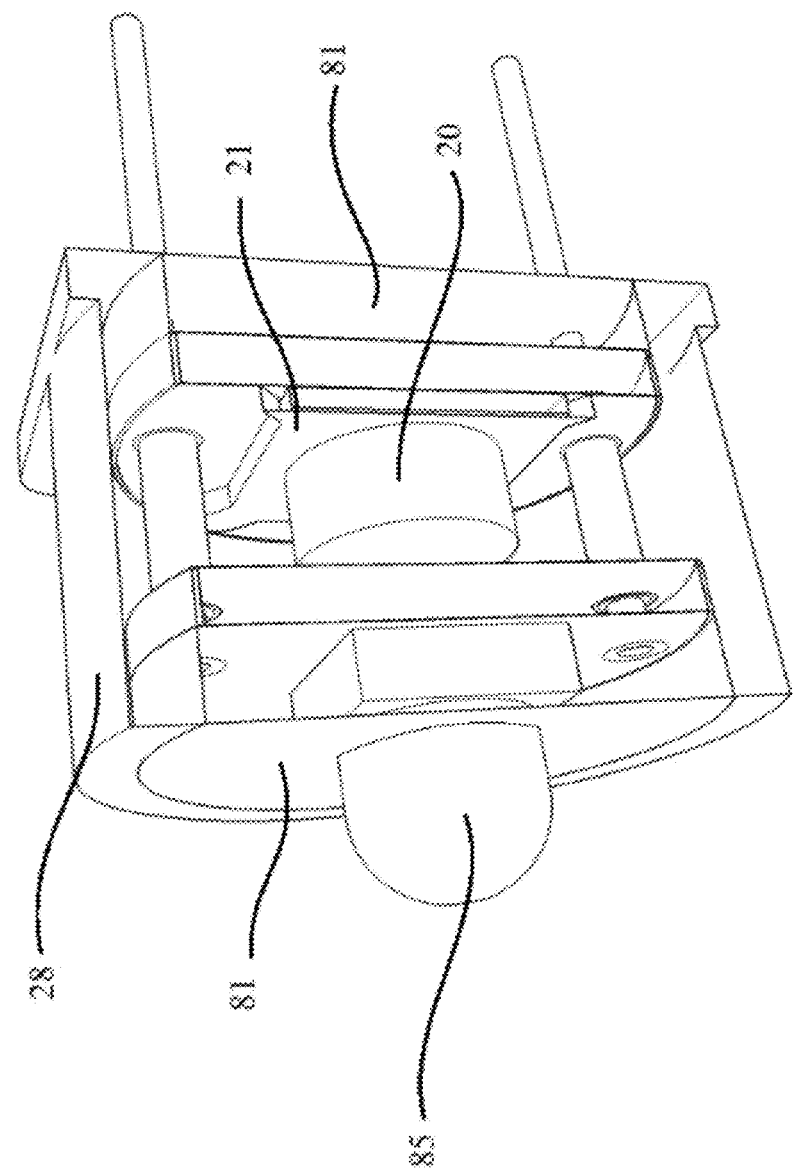
FIG. 32 shows a cut-away view of an embodiment of a light shield combined with an alignment light source.
Figure 33:
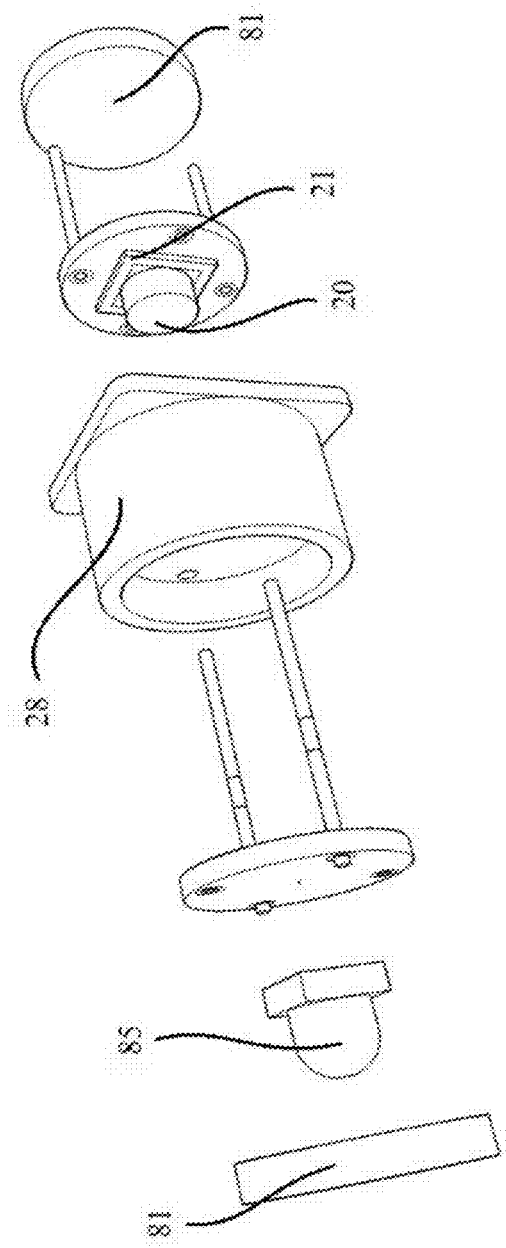
FIG. 33 shows an exploded view of an embodiment of a light shield combined with an alignment light source.

FIG. 30 is a perspective exploded view of an aspect of an embodiment, with light shield 28 having or defining light shield scintillation cavity 28A and detector cavity 28B. Scintillation crystal 20 and light detector 21 may thus fit within these cavities, protected by light shield sealant 81. FIG. 31 is another view of an embodiment of light shield 28, illustrating light shield sealant 81 and optional collimator alignment light or LED 85. FIG. 32 is a cutaway of FIG. 31 illustrating an embodiment with relative positioning of scintillation crystal 20, light detector 21 within light shield 28. FIG. 33 is a further exploded view of that embodiment, showing the inter-relation of the individual components, with collimator alignment light 850

Figure 34:
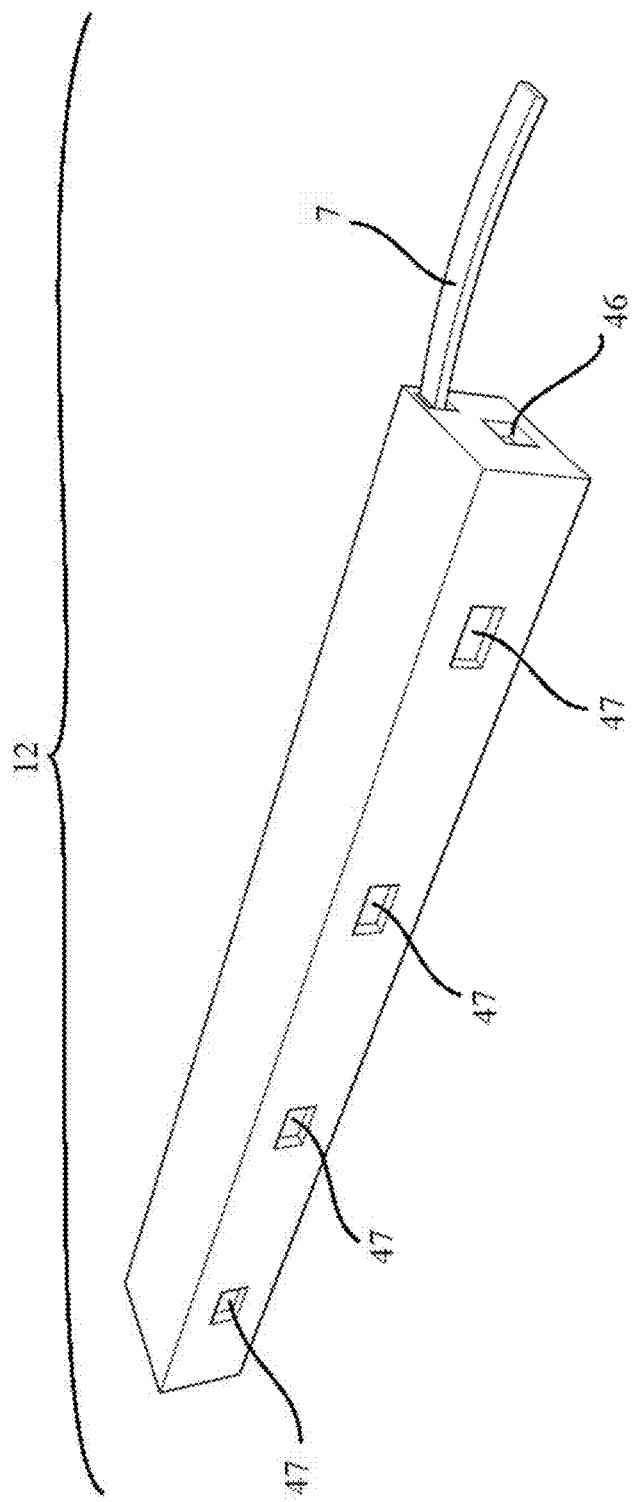
FIG. 34 shows an embodiment of a measurement controller.
Figure 35:
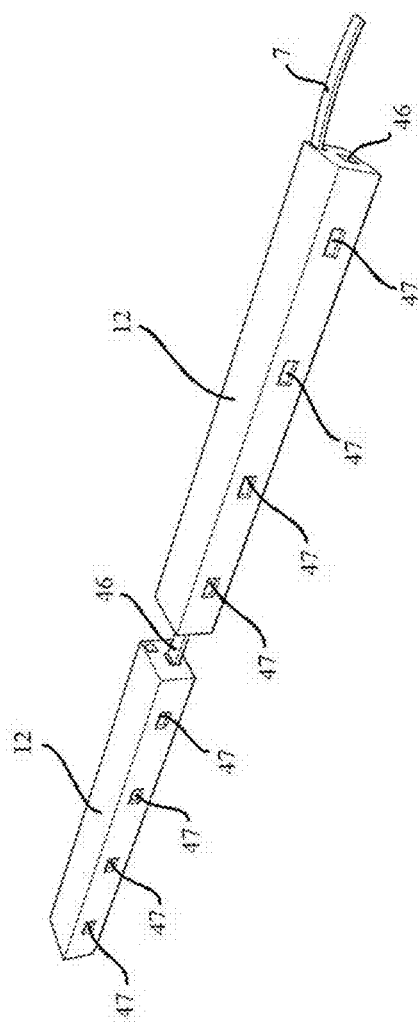
FIG. 35 shows an embodiment of two daisy chained measurement controllers.

FIG. 34 illustrates an embodiment of measurement controller 12, with communication link 7, a plurality of controller communications ports 47 and optional controller daisy chain port 46. FIG. 35 shows two daisy chained controllers.

Figure 36:
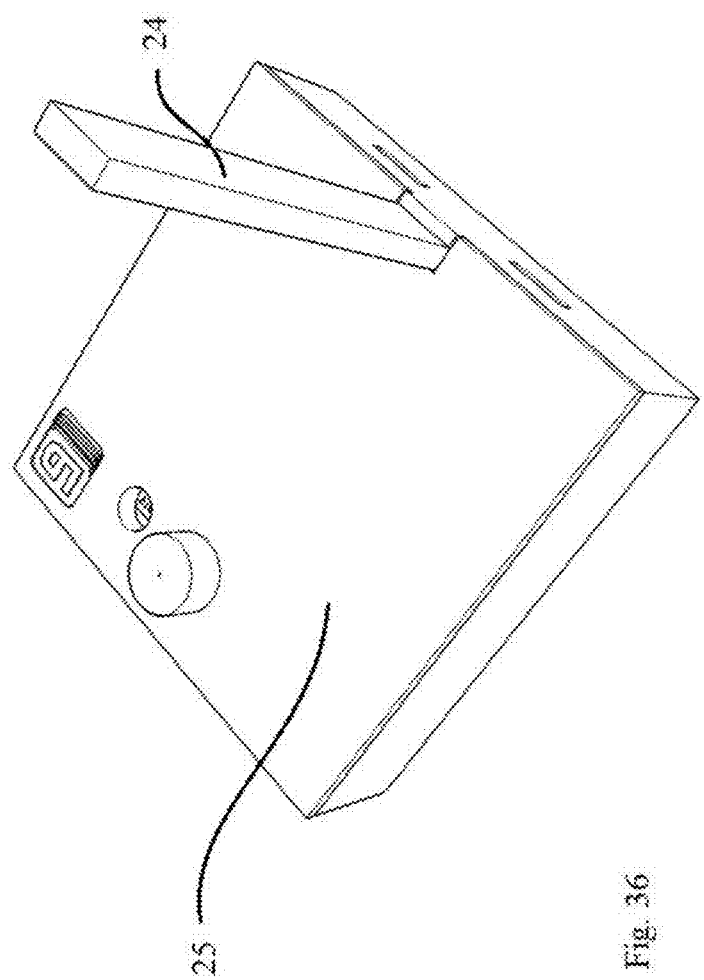
FIGS. 36 and 37 show embodiments of a measurement sensor.
Figure 37:
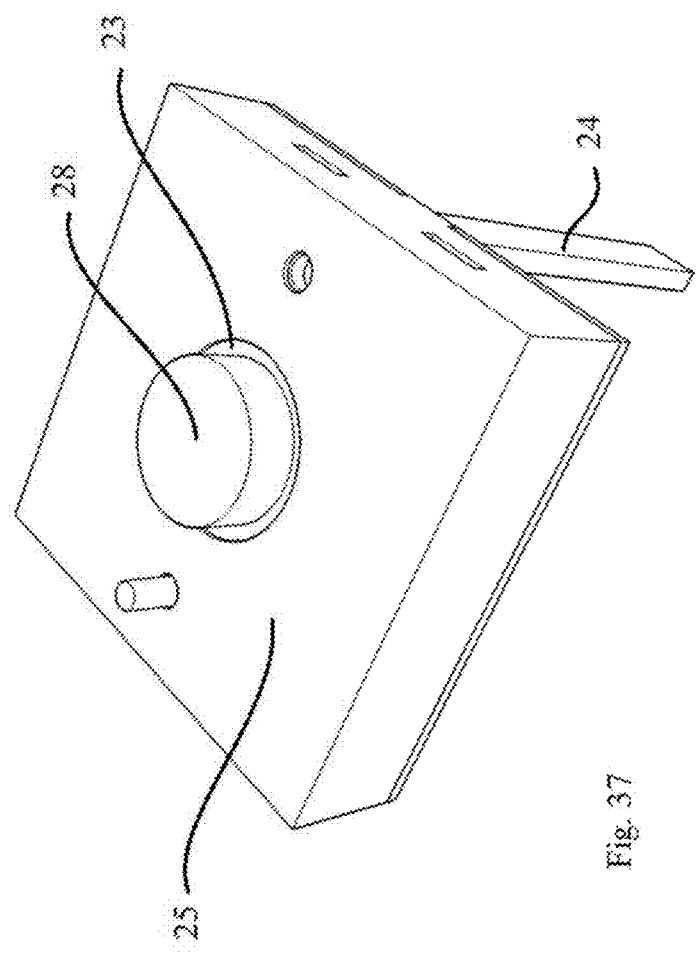
Figure 38:
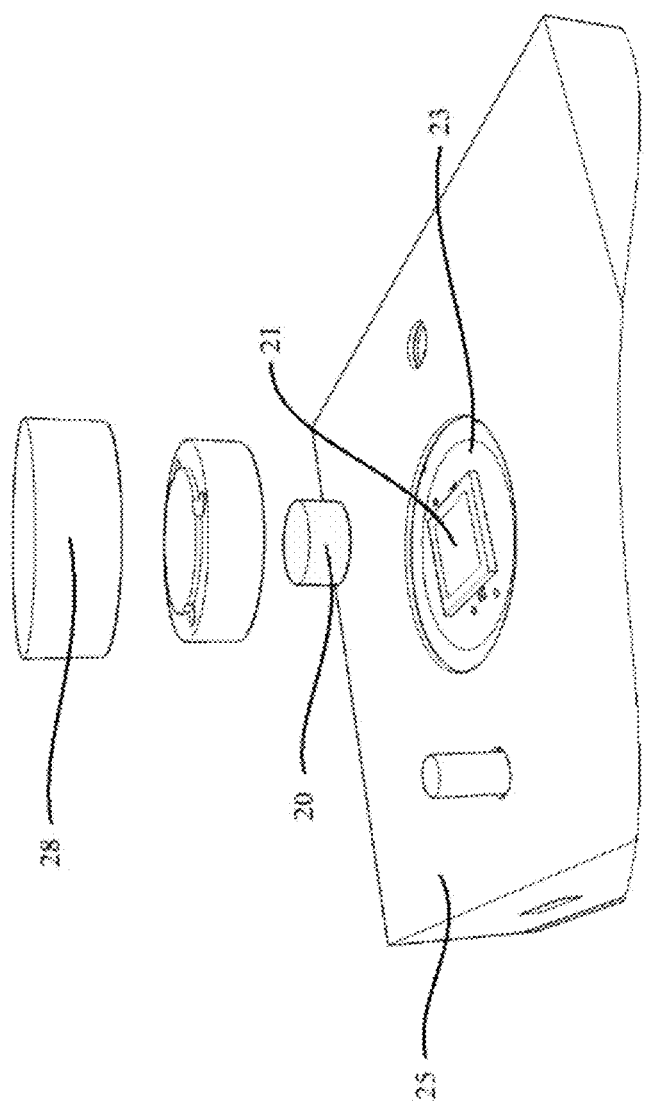
FIG. 38 shows an exploded view of an embodiment of a light shield on an embodiment of a measurement sensor.
Figure 39:
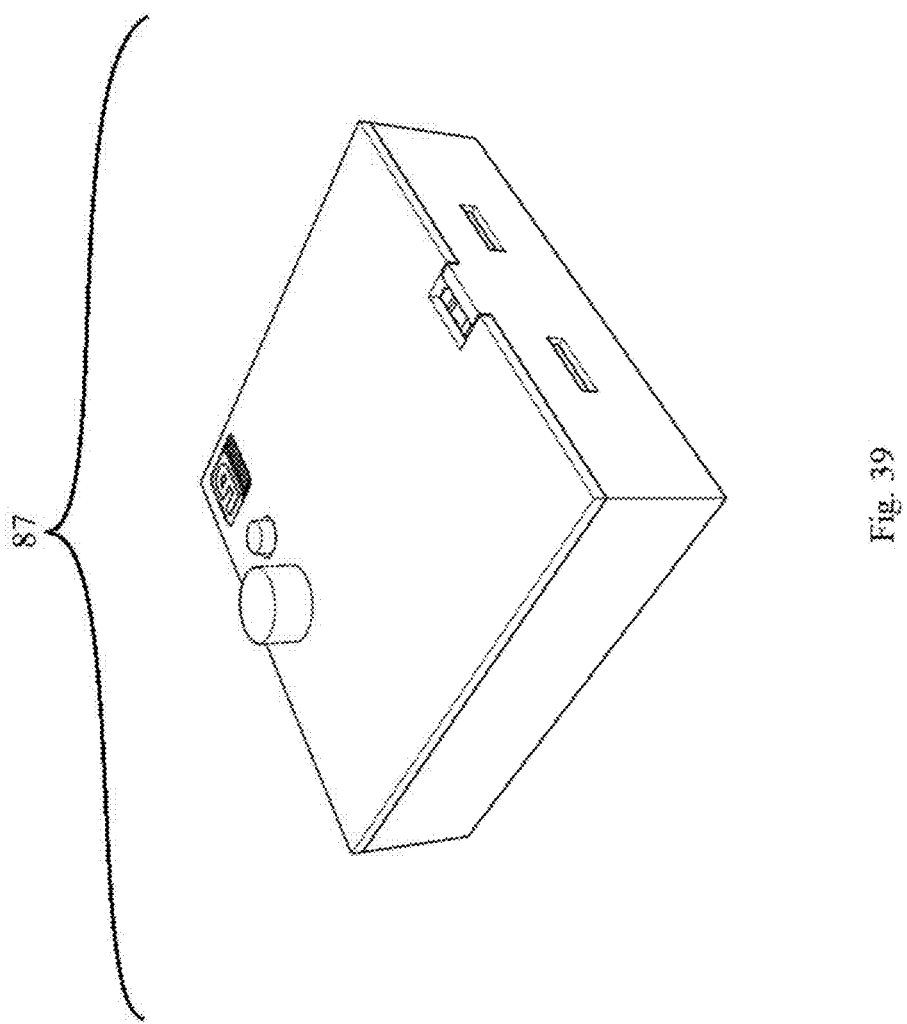
FIGS. 39 and 40 show a view of an embodiment of a radiation shielding mask alignment device.
Figure 40:
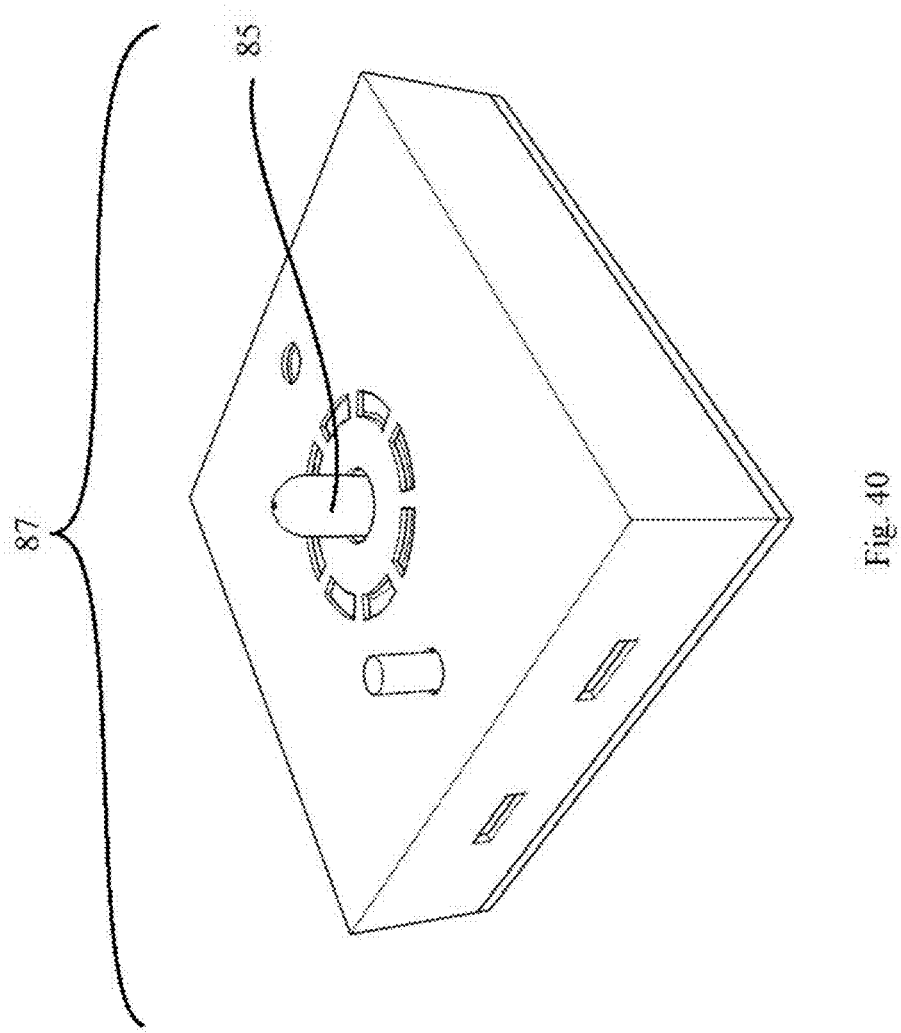
Figure 41:
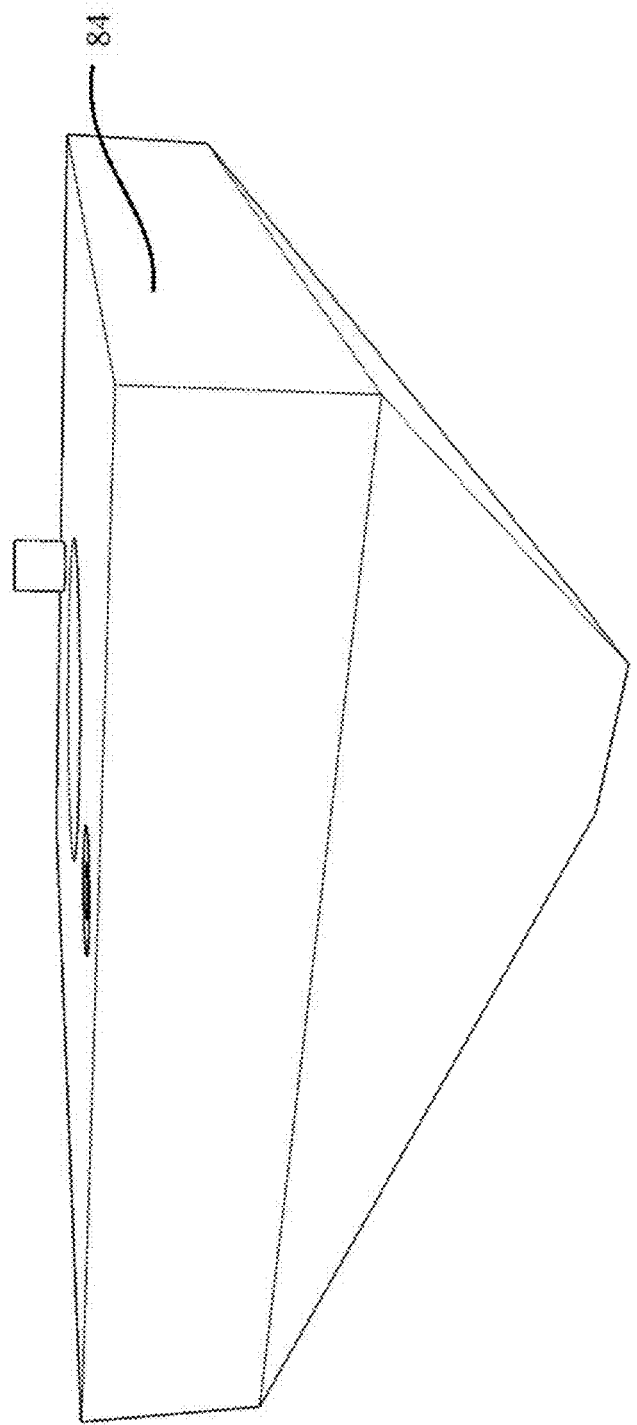
Figure 42:
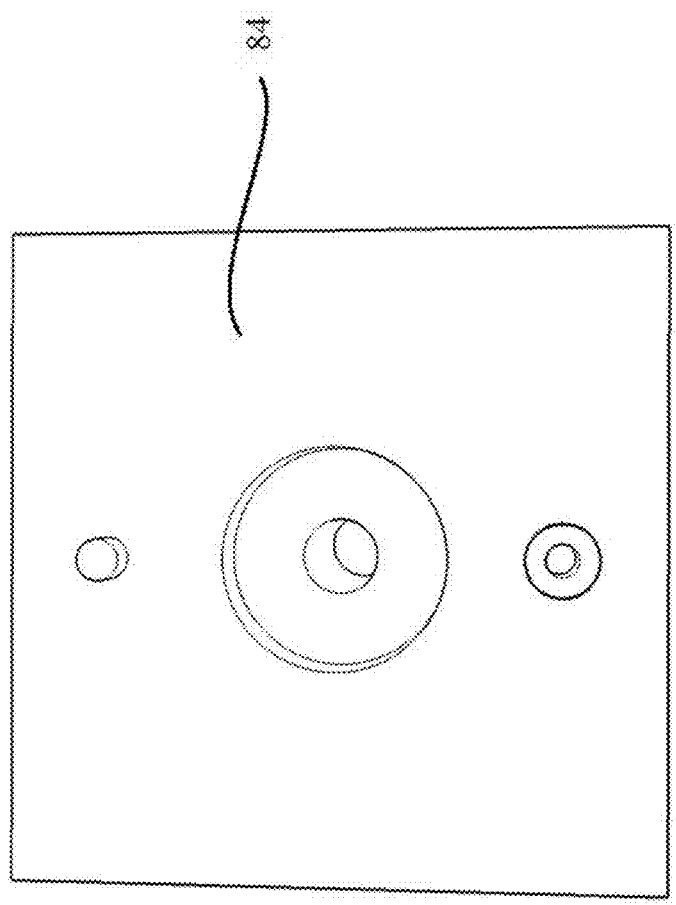
FIG. 42 shows a top view of an embodiment of a radiation shielding mask collimator.
Figure 43:
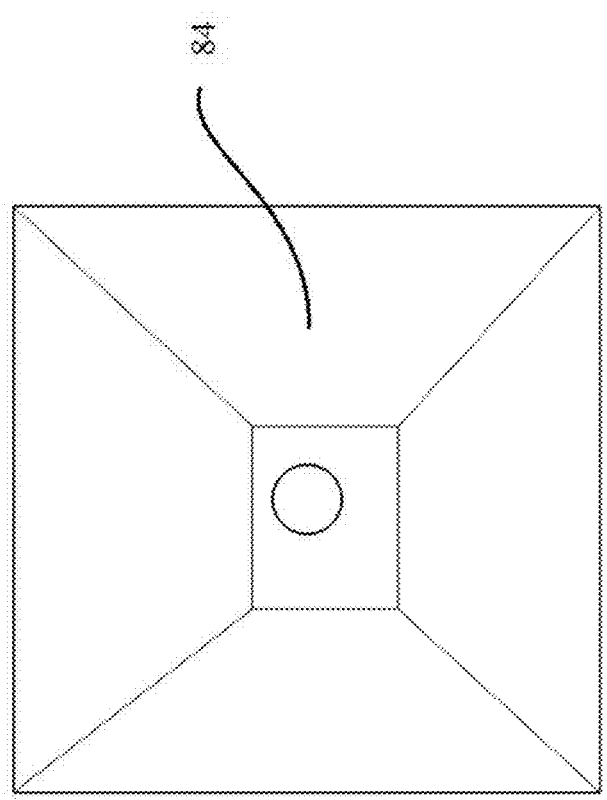
FIG. 43 shows a bottom view of an embodiment of a radiation shielding mask and collimator.
Figure 44:
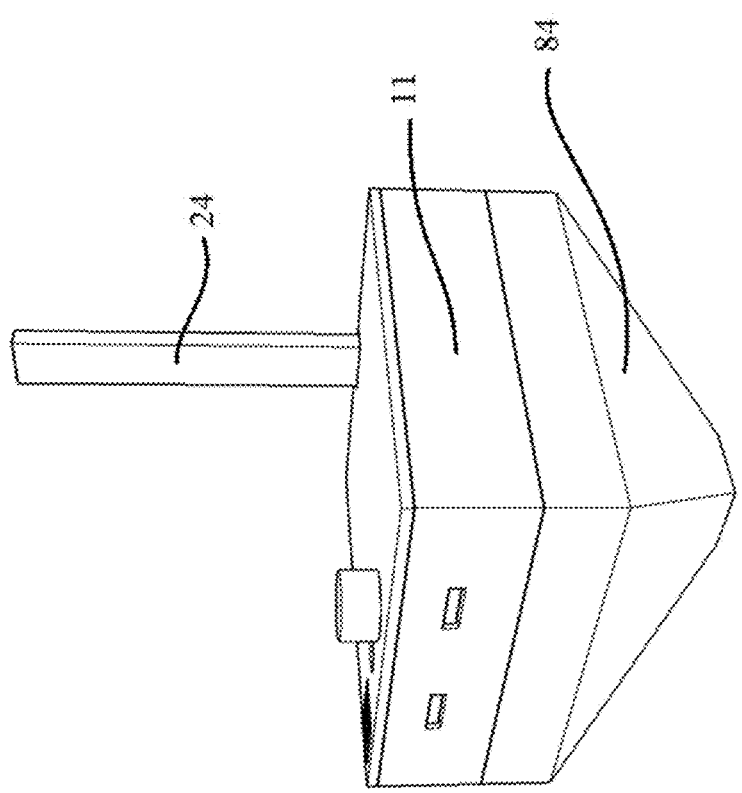
FIG. 44 shows an embodiment of a measurement sensor attached to an embodiment of a radiation shield.
Figure 45:
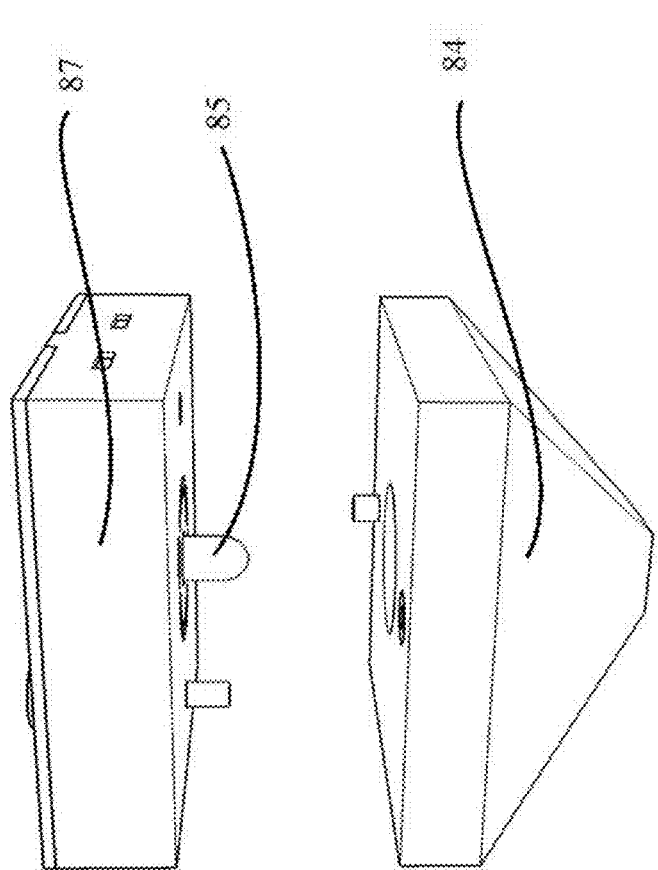
FIG. 45 shows an embodiment of a radiation shield alignment device and an embodiment of a radiation shield.

FIG. 36 shows an embodiment of measurement sensor housing 25, with cable 24. FIG. 37 is an external view of another embodiment of measurement sensor housing 25, with light shield 28 and sensor circuit board 23. FIG. 38 is a partial exploded view of the FIG. 37 embodiment, illustrating light detector 21 and scintillation material 20 with respect to light shield 28 and sensor housing 25. FIGS. 39 and 40 show different sides of an embodiment with a radiation shield alignment device 87 and collimator alignment device 85. FIG. 41 illustrates radiation shield 84. FIGS. 42-43 show details of radiation shield 84. In FIG. 44 is an external bottom side view of an embodiment of measurement sensor 11 with radiation shield 84, with FIG. 45 showing an exploded view of the same embodiment with components separated.

Figure 46:
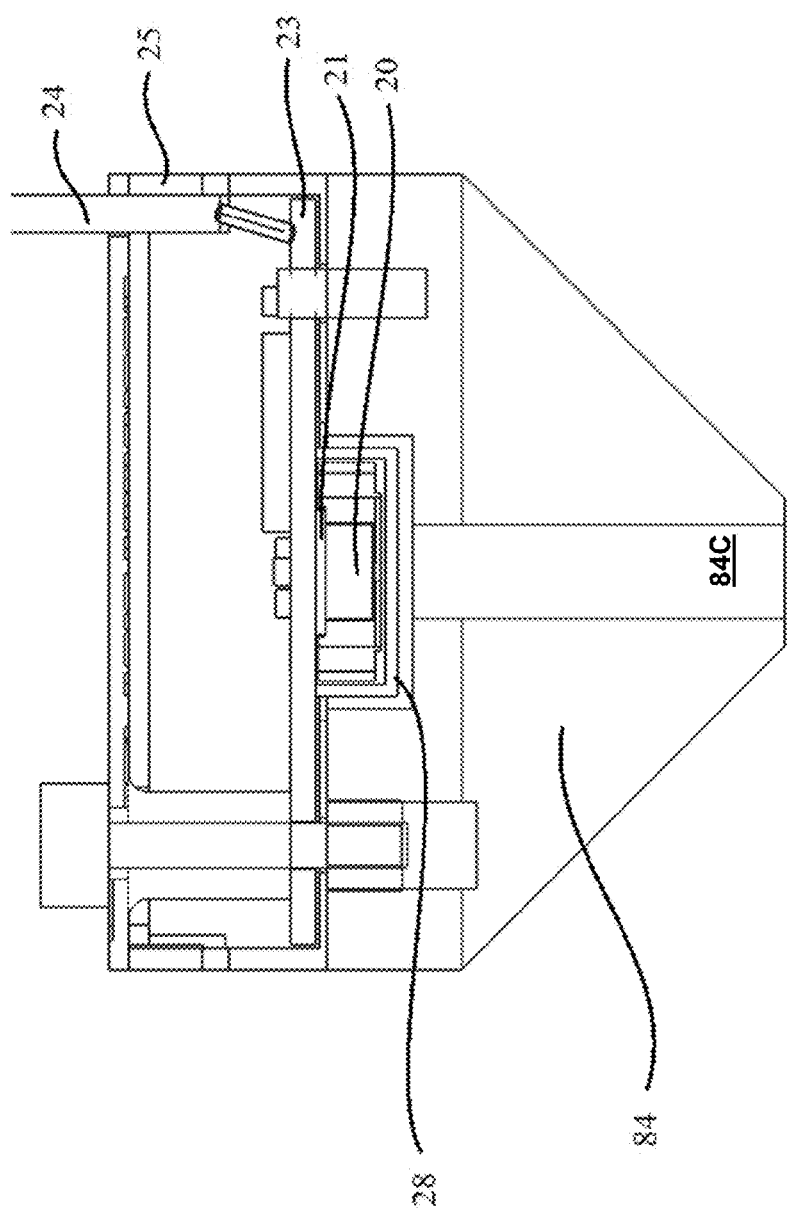
FIG. 46 shows a cut away view of an embodiment of a measurement sensor attached to an embodiment of a radiation shield.
Figure 47:
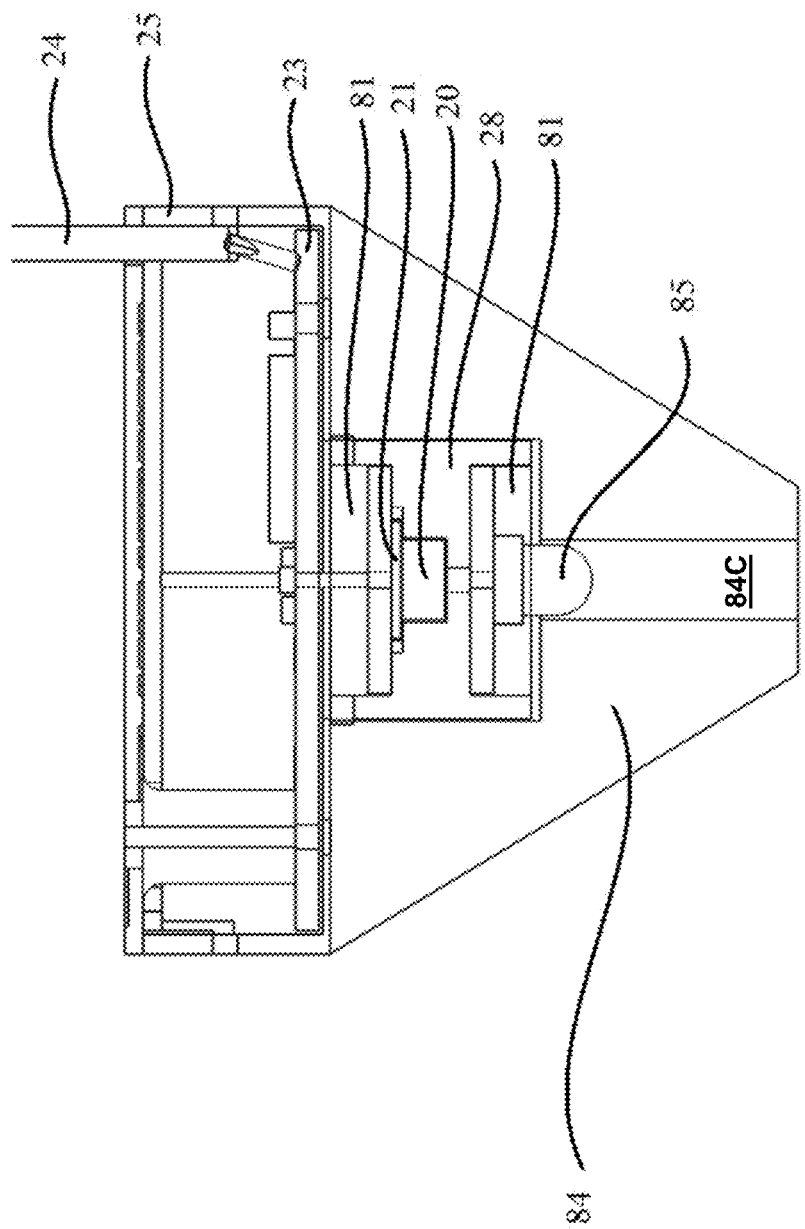
FIG. 47 shows a cut away view of an embodiment of a measurement sensor attached to an embodiment of a radiation shield.
Figure 48:
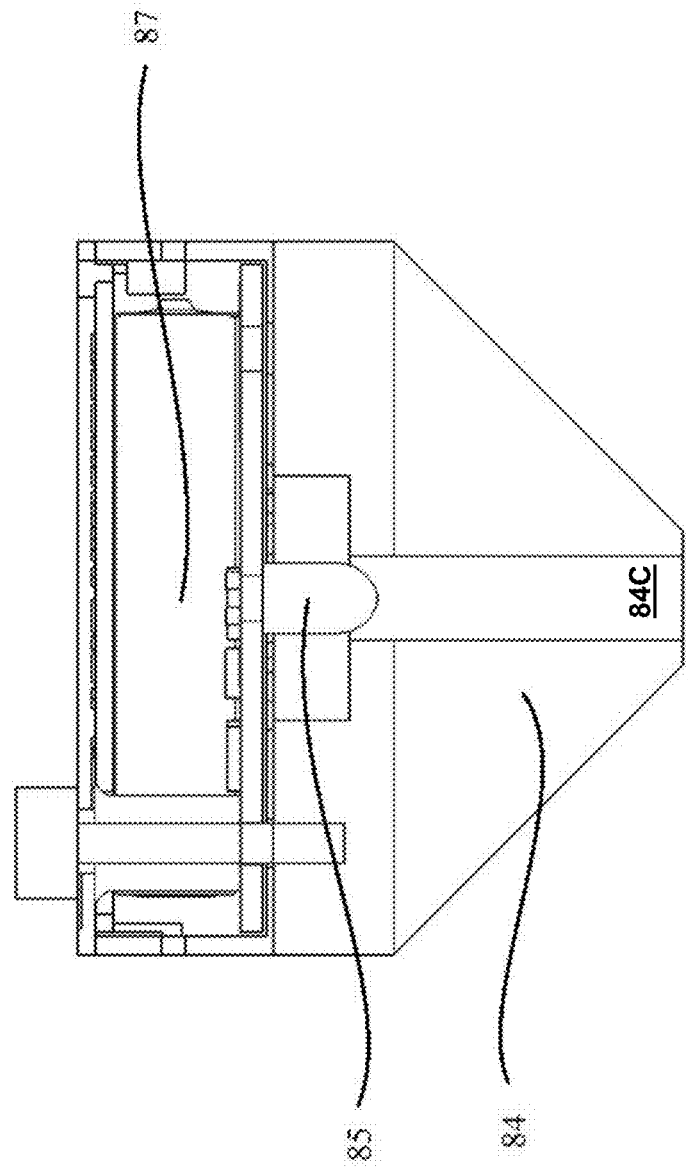
FIG. 48 shows a cut away view of an embodiment of a radiation shield alignment device attached to an embodiment of a radiation shield.

FIG. 46 is a cutaway view of an embodiment of measurement sensor 11 attached to a radiation shield 84 defining a collimator, with scintillation material 20 and light detector 21. FIG. 47 is a cutaway view of another embodiment of measurement sensor 11, illustrating optional collimator alignment device 85. FIG. 48 is a further cutaway view of an embodiment with a different configuration for collimator alignment device 85.

Figure 49:
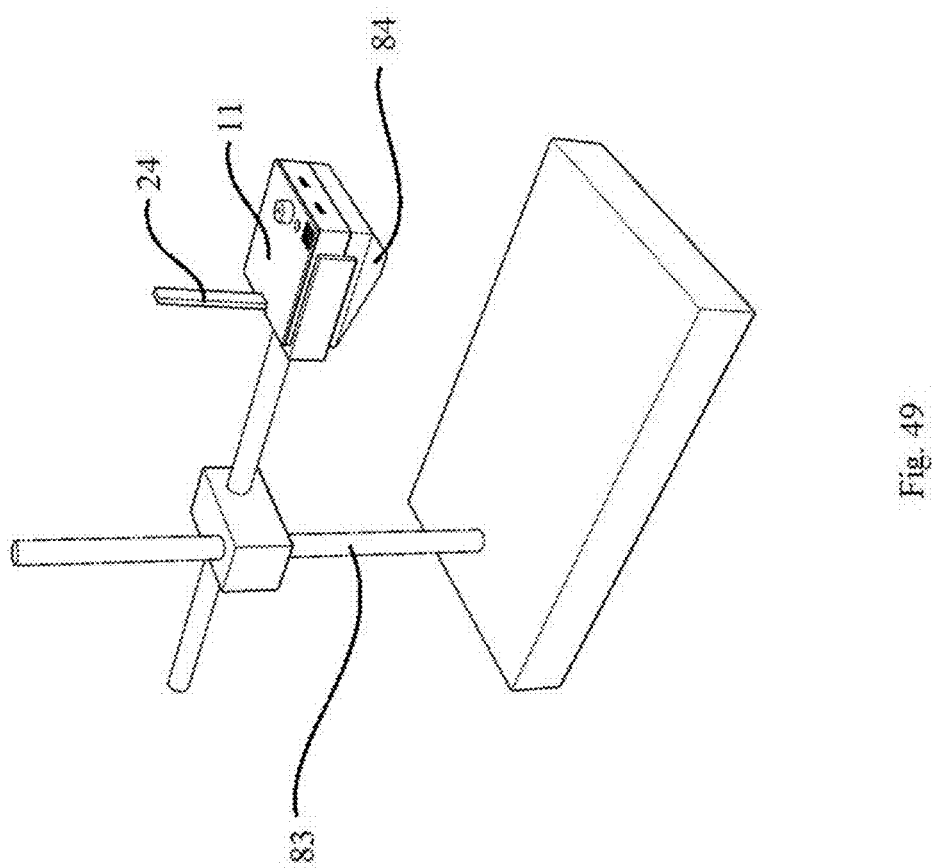
FIG. 49 shows an embodiment of a measurement sensor and attached radiation shield attached to a measurement sensor stand.
Figure 50:
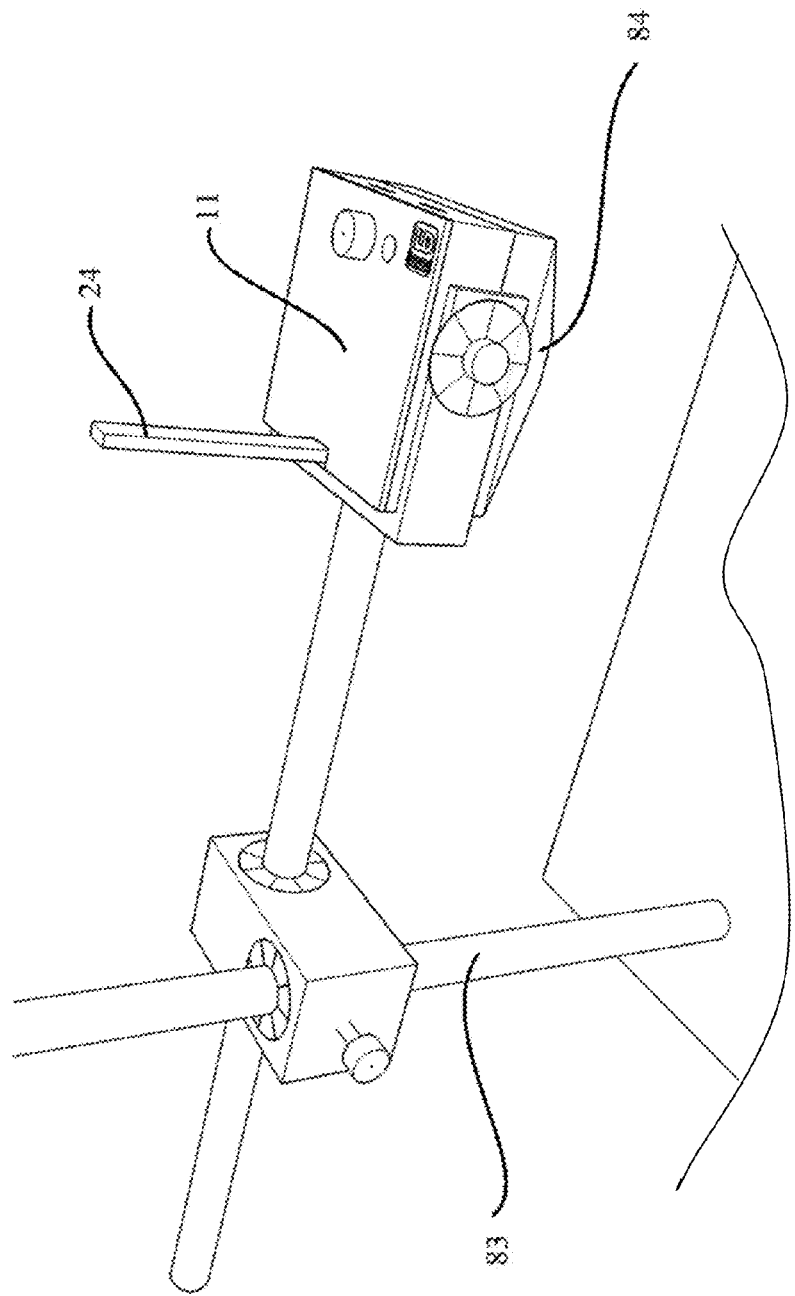
FIG. 50 shows a detailed view of an embodiment of a measurement sensor
Figure 51:
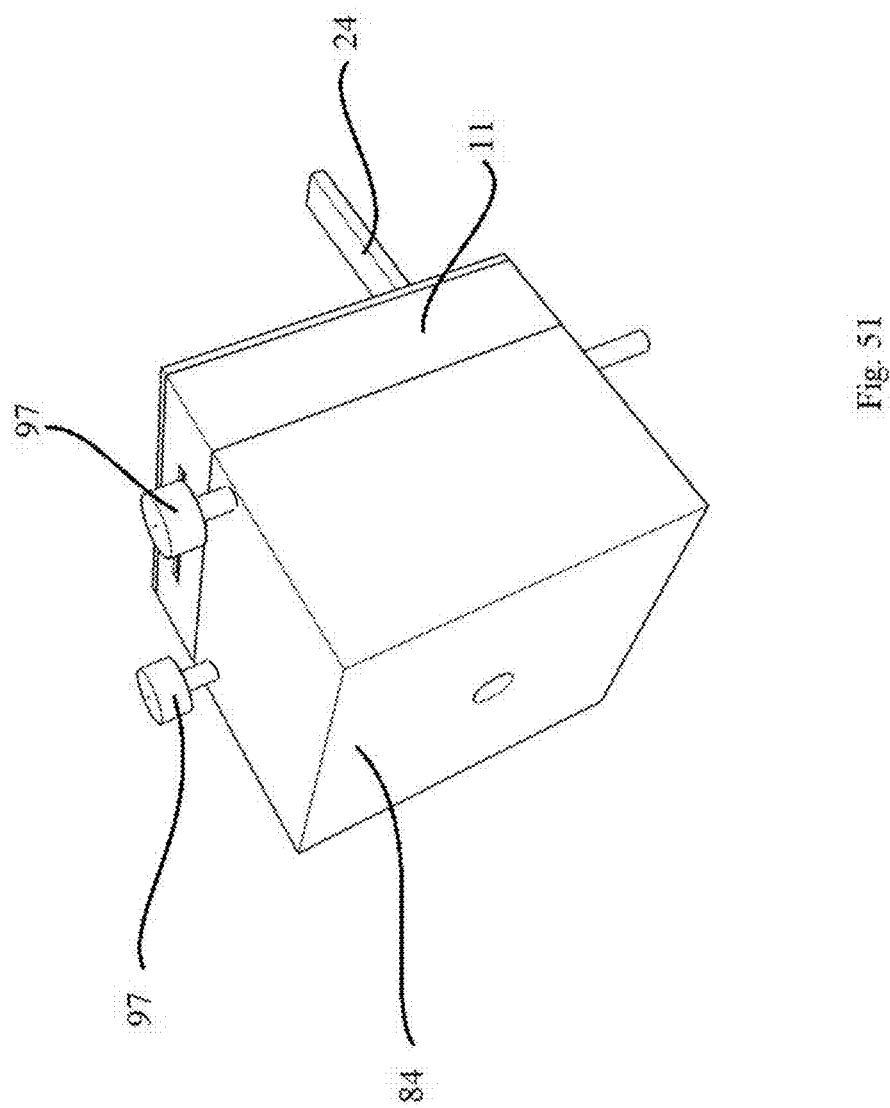
FIG. 51 shows an embodiment of a measurement sensor attached to an embodiment of a radiation shielding mask with adjustment legs.
Figure 52:
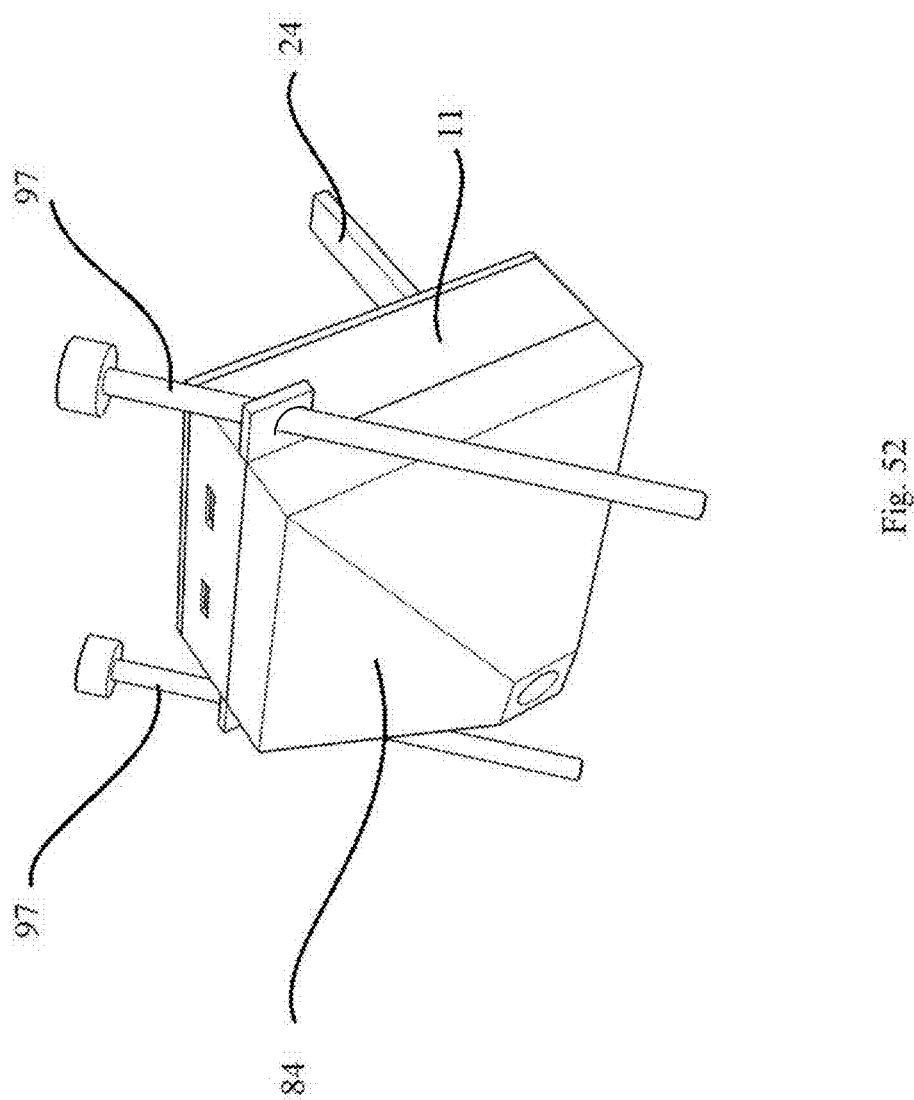
FIG. 52 shows an embodiment of a measurement sensor attached to an embodiment of a radiation shielding mask with adjustment legs.

FIG. 49 is a perspective view of an embodiment of measurement sensor 11 with measurement sensor stand 83. FIG. 50 is a closer view of the embodiment of FIG. 49. FIGS. 51-52 show two different perspective views of an embodiment detail with optional radiation shield adjustment legs 97.

Figure 53:
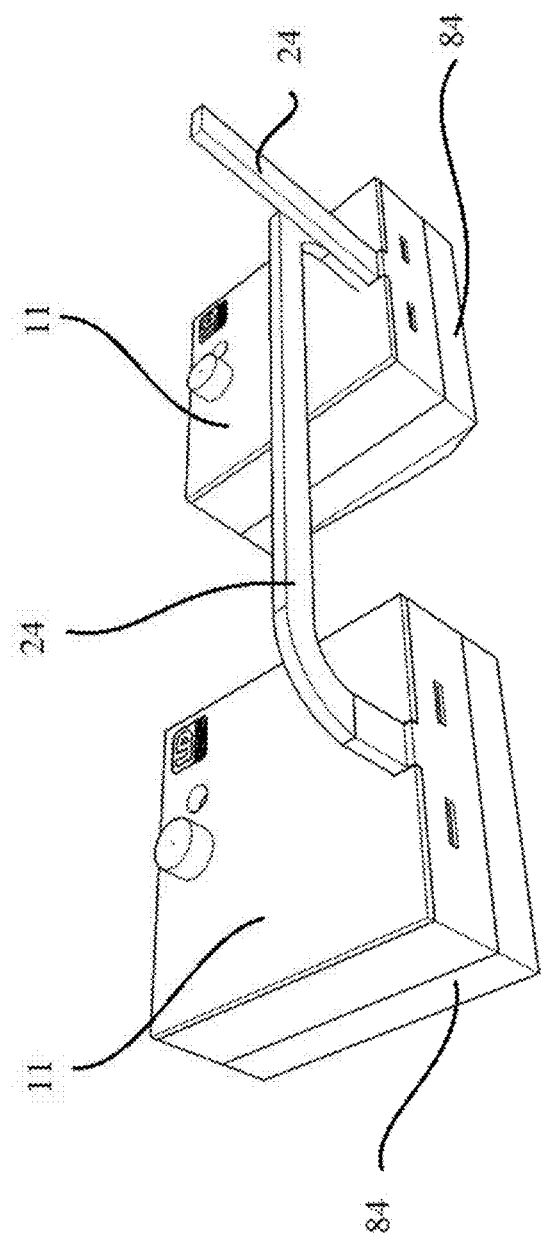
FIGS. 53 and 54 show embodiments of measurement sensors daisy chained together.
Figure 54:
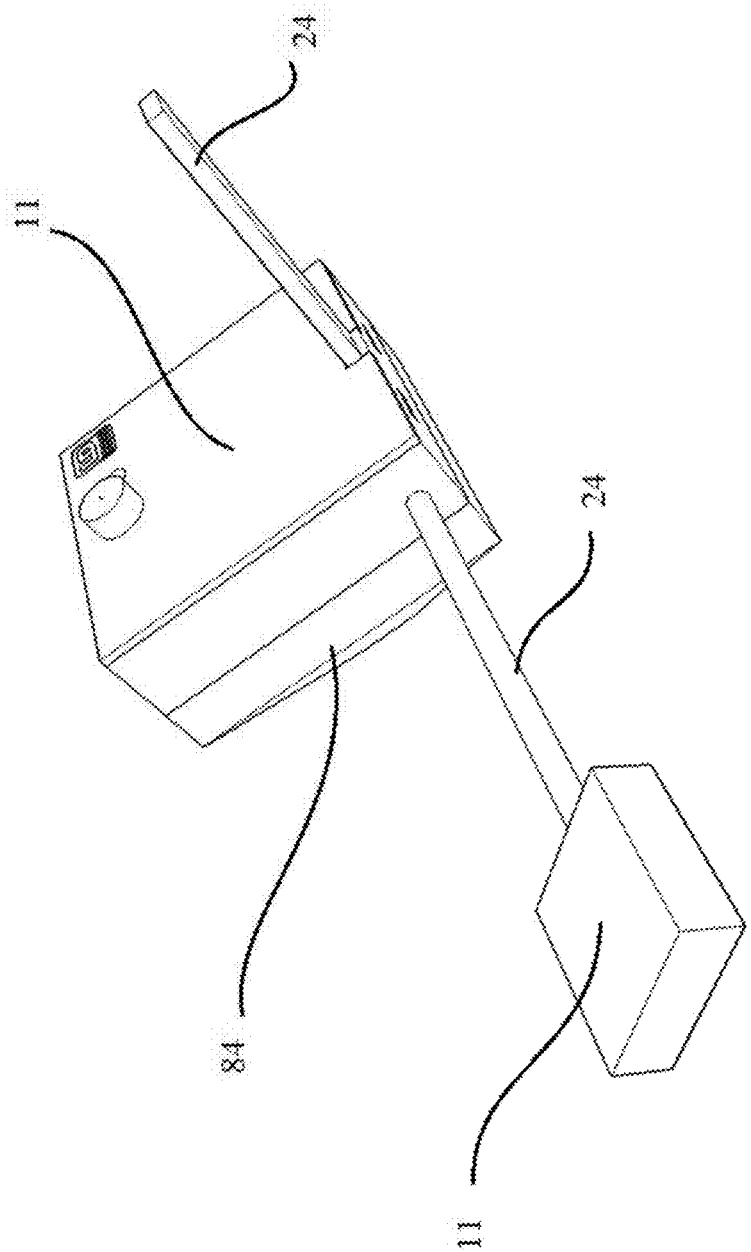
Figure 55:
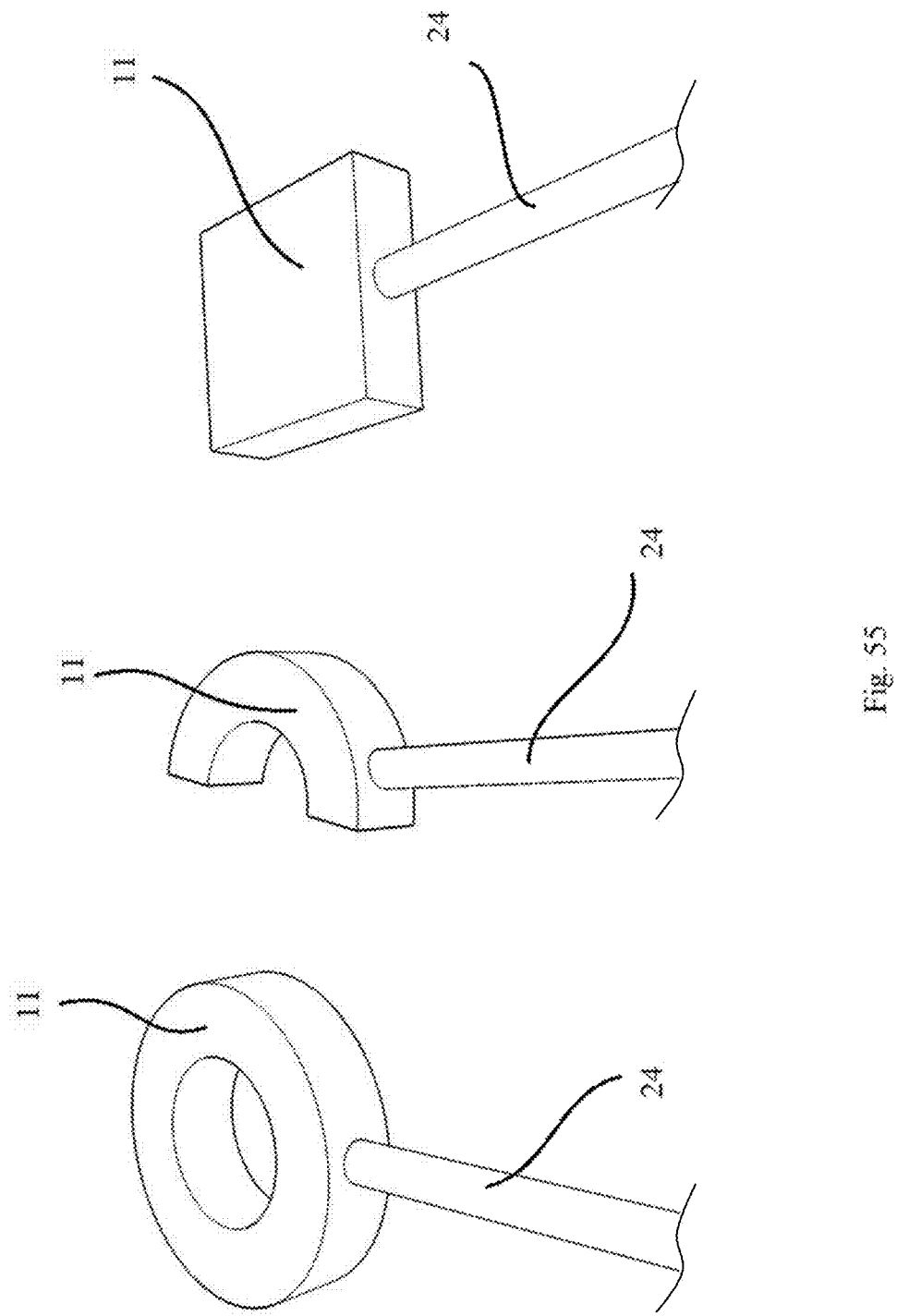
FIG. 55 shows three embodiments of measurement sensors.
Figure 56:
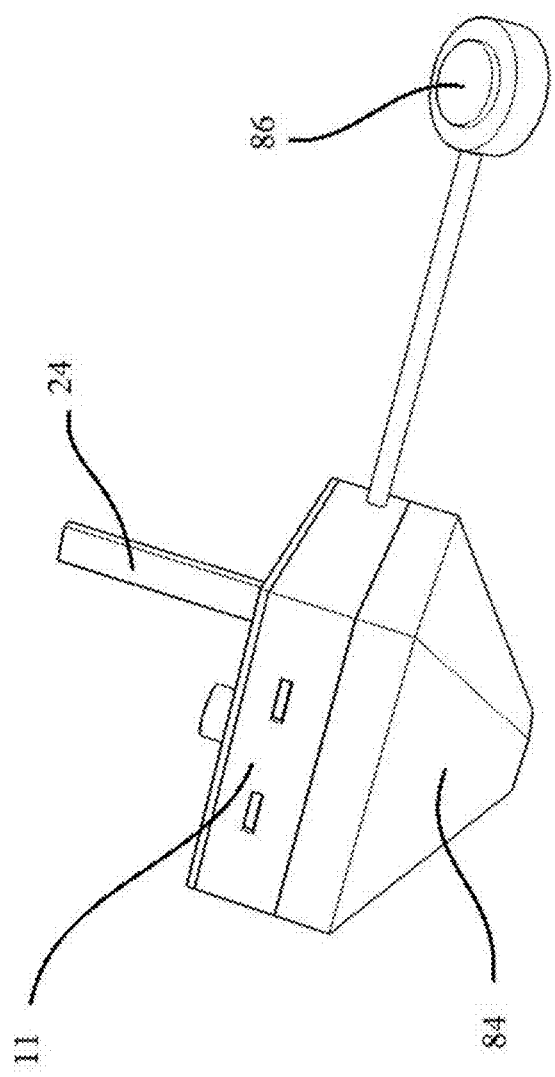
FIG. 56 shows an embodiment of a measurement sensor with attached external push button.

FIG. 53 illustrates an aspect of some embodiments, with two measurement sensors 11 daisy chained with cable 24. FIG. 54 is another embodiment in which a secondary measurement sensor 11 is daisy changed to a primary measurement sensor 11 having shielding mask 84. FIG. 55 illustrates various form factors for specific embodiments of measurement sensor 11 having specific applicability. FIG. 56 is an embodiment with an optional sensor trigger pushbutton 86.

FIG. 57 is a cutaway view of measurement sensor 11, highlighting backscatter material 82. FIG. 58 details structure of measurement sensor housing 25 serving as structure for backscatter materials 82.

Some system 10 embodiments may be directed to the ex vivo real-time detection of gamma radiation emitted by a subject from administration and uptake over a period of time of a radioactive analyte that decays in vivo by positron emission. These systems 10 may include at least one ex vivo measurement sensor 11, at least one computer processor 42 (which may or may not be the same as computer/processing station 70) having a non-transient memory 40 and a clock 48, the computer processor 42 in operable communication with the measurement sensor 11, a temperature compensator 50, and computer program code. An ex vivo measurement sensor 11 may have a sensor housing 25, a scintillation material 20, a light detector 21, a temperature sensor 36, a signal amplifier 33, and a sensor power source 32 (whether corded, battery, solar, etc). The light detector 21, temperature sensor 36, signal amplifier 33, and sensor power source 32 may generally be in operable communication. The scintillation material 20 and light detector 21 may be disposed within the sensor housing 25 in a light proof manner, with the scintillation material 20 adapted to receive a level of gamma radiation over the period of time from the in vivo radioactive analyte and to emit photons representative of the gamma radiation level. The light detector 21 may be disposed with respect to the scintillation material 20 so as to receive and convert the photons into signal data representative of the frequency level over time of gamma radiation received. The signal amplifier 33 may be adapted to amplify the signal data, the measurement sensor 11 having at least one sensor output for such amplified signal data, The at least one computer processor 42 may include a non-transient memory 40 and a clock 48, with the computer processor 42 being in operable communication with the measurement sensor 11. The memory 40 may have control computer program code executable by the at least one computer processor 42. The control computer program code may include a number of software modules, such as a first module 61 for measurement, a second module 62 for data management.

An optional temperature compensator 50 may be coupled with the temperature sensor 36, such that the temperature sensor 36 is adapted to measure an ambient temperature. The system 10 may thus be adapted to communicate the ambient temperature to the temperature compensator 50, so that the temperature compensator 50 may generate a temperature correction factor based on comparison of the ambient temperature to a reference temperature. The temperature compensator 50 further adapted to apply the temperature correction factor to the signal data to produce temperature compensated signal data.

The first module 61 may be adapted to receive the signal data in a record file format, and the second module 62 may be adapted to receive the signal data of a record file from the first module 61 and to transmit the compensated signal data to a desired storage. The computer program code 56 may further include a third module 63 adapted to receive stored data of a record file from the second module 62, and to apply such stored data to calculate changes in the compensated signal data over a desired period. This module may also apply stored data to a predictive model to generate predictive data values over a desired period for such record file as a predictive outcome, and to transmit such changes to a desired storage, such as database storage 75.

Optionally, the ex vivo measurement sensor 11 may include a radiation shielding mask 84 for gamma radiation. The shielding mask 84 may define an aperture in the form of a collimator 84c for gamma radiation incident into the scintillation material 20. An alignment feature 87 may be included for removable alignment of the measurement sensor 11 with respect to the subject 5. In some cases, the alignment, feature 87 may include a light emitter 85 disposed within the sensor 11 so as permit alignment of the collimator aperture 84c to a desired portion of the subject 5 by illumination of the subject 5. Optionally, the light emitter 85 may be a light emitting diode (LED) disposed within the aperture, and optionally the ex vivo measurement sensor 11 may further include light proof sealant 81 about the LED 85 to prevent the output of the diode or ambient light to strike the scintillation material 20, while permitting the scintillation material 20 to receive incident gamma radiation.

Optionally, the ex vivo measurement sensor 11 may further include a radiation shielding mask 84 for gamma radiation, with the shielding mask defining an aperture in the form of a collimator 84c for gamma radiation incident into the scintillation material 20; and the system 10 may further provide a stand 83 as alignment feature 87 for the removable mounting of the ex vivo measurement sensor 11 in a configuration relative to the subject 5 so as to permit alignment of the collimator 84c aperture to a desired portion of the subject 5.

Optionally, the third module 63 may detect infiltration conditions. In one approach, the third module 63 calculates changes in the compensated signal data in order to determine infiltration of radioactive analyte. In another approach, the predictive model includes data representative of radiation frequency over time associated with infiltration of the analyte within the subject for determining an infiltration. Such a predictive model may include data representative of spike of radiation frequency over time associated with administration of the analyte for determining proper administration of the analyte. An alarm or indicator may be included to announce the determination of infiltration. Also optionally, some embodiments may include an arm-band 78 for removable affixation of the ex vivo measurement sensor 11 to an arm of the subject 5.

Optionally, a filter in noise reduction 37 may be included for filtering the amplified signal data based on amplitude. Such a filter may be implemented with a voltage comparator. Alternatively, the filter may comprises an analog to digital converter and control computer program code adapted to compare digital amplified signal data to a reference level.

A further system 10 embodiment may also be directed to the ex vivo real-time detection of gamma radiation emitted at an area of interest by a subject from administration and uptake over a period of time of a radioactive analyte that decays in vivo by positron emission. Such an embodiment may include a primary ex vivo measurement sensor 11 and a secondary ex vivo measurement sensor 11. The primary ex vivo measurement sensor 11 may include a sensor housing 25 with a radiation shield 84, the sensor housing 25 with the radiation shield 84 defining a cavity, the radiation shield 84 further defining an aperture into the cavity as a collimator 84c disposed within the aperture so as to admit a collimated gamma radiation into the cavity from the area of interest, a scintillation material 20 disposed within the cavity such that the collimated gamma radiation is incident on the scintillation material 20, a light detector 21 disposed within the sensor housing 25 to detect light emitted from the scintillation material 20, a temperature sensor 36, a signal amplifier 33, and a sensor power source 32. The light detector 21, temperature sensor 36, signal amplifier 33, and sensor power source 32 in operable communication.

In general, the scintillation material 20 and light detector 21 may be disposed within the sensor housing 25 with the scintillation material 20 adapted to receive a level of gamma radiation over the period of time from the in vivo radioactive analyte, and to emit photons representative of the gamma radiation level. As above, the light detector 21 may be disposed with respect to the scintillation material 20 in a manner adapted to receive and convert the multiplied photons into signal data representative of the frequency level over time of gamma radiation received. The signal amplifier 33 may amplify the signal data, and the measurement sensor 11 may have at least one sensor output (e.g., port 27) for such amplified signal data.

In this embodiment, there is a secondary ex vivo measurement sensor 11 that is unshielded for measuring background gamma radiation, and a collimator alignment system 87 in operable engagement with the sensor housing 25 for aligning the collimator 84c to the area of interest.

A temperature compensator 50 may be coupled with the temperature sensor 36, such that the temperature sensor 36 is adapted to measure an ambient temperature. The system 10 may thus be adapted to communicate the ambient temperature to the temperature compensator 50, so that the temperature compensator 50 generates a temperature correction factor based on comparison of the ambient temperature to a reference temperature. The temperature compensator 50 is further adapted to apply the temperature correction factor to the signal data to produce temperature compensated signal data.

The at least one computer processor 42 includes a non-transient memory 40 and a clock 48, with the computer processor 42 in operable communication with the primary and secondary measurement sensors 11. The memory 40 may have or store control computer program code 56 executable by the at least one computer processor 42, the control computer program code 56 may have a first module 61 for measurement and a second module 62 for data management. The first module 61 may be adapted to receive the signal data in a record file format. The second module 62 may be adapted to receive the signal data of a record file from the first module 61 and to transmit the compensated signal data to a desired storage (e.g., database storage 75). Also included may be third and fourth modules 63, 64 of computer program code 56, the third module 63 adapted to receive stored data of a record file from the second module, (i) to apply such stored data to a predictive model to generate predictive data values over a desired period for such record file as a predictive outcome, and to transmit such predictive outcome to a desired storage; and (ii) to apply such stored data to calculate changes in the compensated signal data over a desired period, and to transmit such changes to a desired storage and the fourth module 64 adapted to subtract signal data from the secondary ex vivo measurement sensor 11 from signal data from the primary ex vivo measurement sensor 11 having radiation shield 84.

This embodiment may include the various options corresponding to the options of the foregoing embodiments, though as appropriate, for the shielded primary ex vivo measurement sensor 11. The secondary measurement sensor 11 remaining unshielded for the detection of background radiation.

Some embodiments may specifically be directed to the identification of proper or improper administration of the radioactive analyte to the subject, including, but not limited to, infiltration, for example. One such embodiment might be a system 10 for the ex vivo real-time detection over a period of time of gamma radiation emitted by a subject 5 from the administration of a radioactive analyte that decays in vivo. The parametric pattern of data amplitude, slope, and/or time) from either or both proper and improper administration may be used as reference data. The system can compare the amplified signal data of an administration to this reference data using a parametric model to determine the probability of proper (or improper) administration of the radioactive analyte to the subject.

In this case, system 10 may include at least one ex vivo gamma radiation measurement sensor 11 to detect gamma radiation over a desired period of time, and to produce signal data associated with the desired period of time. The ex vivo measurement sensor 11 may be adapted to sensing gamma radiation proximate to a point of administration on the subject 5 of the radioactive analyte. A signal amplifier 33 may be in operable communication with the gamma radiation sensor 11 to amplify the signal data. As above, the measurement sensor 11 may include at least one sensor output or port for communicating such amplified signal data. The data may be processed by at least one computer processor 42 in operable communication or associated with a non-transient memory 40. Computer processor 42 may also be in operable communication with the measurement sensor 11 via its output.

The non-transient memory 40 may have computer program code 56 executable by the computer or controller processor 42 to perform the steps of receiving the amplified signal data with the desired period of time, accessing reference data distributed over a reference period of time, comparing the amplified signal data to the reference data using a parametric model to determine the probability of a proper administration of the radioactive analyte to the subject 5. The computer program code 56 may be further adapted to normalize the amplified signal data, and the parametric model may be a time series function of one or more of the amplitude and slope of the amplified signal data.

Figure 59:
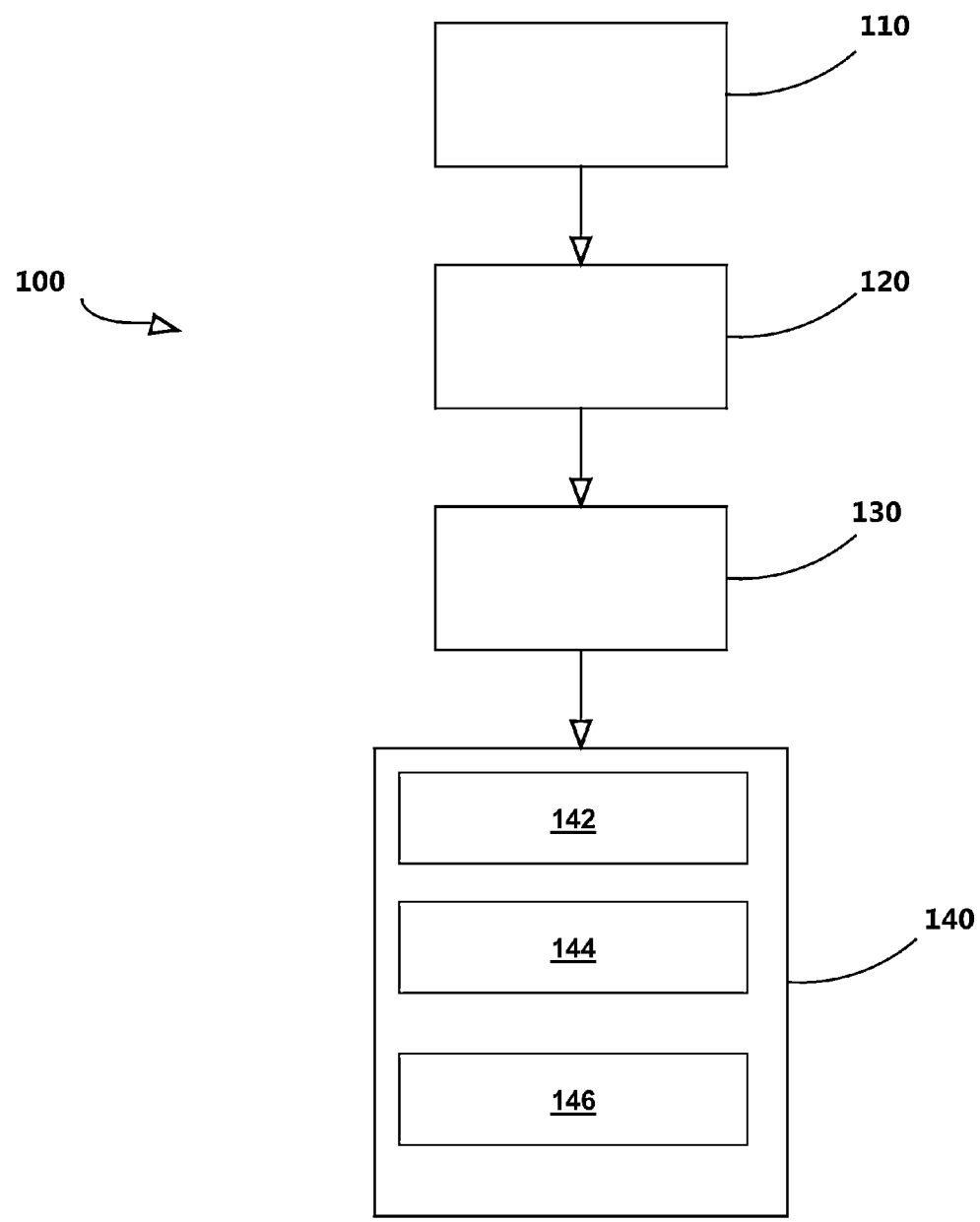
FIG. 59 is a method implementation of the present approach.

Embodiments may extend to a method 100 for the ex vivo real-time detection over a period of time of gamma radiation emitted by a subject from the administration of a radioactive analyte that decays in vivo, as shown in FIG. 59. Such a method may include the steps of (i) applying 100 an at least one ex vivo gamma radiation measurement sensor 11 proximate to a point of administration on the subject 5 of the radioactive analyte; (ii) detecting 120 gamma radiation over a desired period of time and producing signal data associated with the desired period of time; (iii) amplifying 130 the signal data using a signal amplifier in operable communication with the gamma radiation sensor, wherein the measurement sensor having at least one sensor output for such amplified signal data and outputting the amplified signal data; (iv) processing 140 the amplified signal data using a computer processor in operative communication with a non-transient memory and the measurement sensor output by performing the step of: (a) receiving 142 the amplified signal data associated with the desired period of time; (b) from the nontransient memory, accessing 144 reference data distributed over a reference period of time; and (c) determining 146 if the administration of the radioactive analyte properly administered the radioactive analyte into the subject by comparing the amplified signal data to the reference data using a parametric model. Optionally, the processing 140 of the amplified signal data may further comprises the step of normalizing the amplified signal data. The parametric model may also be a time series function of one or more of the amplitude and slope of the amplified signal data.

A system 10 embodiments may include, but are not limited to, an ex vivo measurement sensor 11 having a sensor housing 25, a scintillation material 20 as a gamma radiation detector or sensor, a light detector 21, a signal amplifier 33, and a sensor power source 32. Light detector 21, signal amplifier 33, and sensor power source 32 may be in operable communication. The scintillation material 20 and light detector 21 may be disposed within the sensor housing 25 in a light proof manner, with the scintillation material 20 adapted to receive a level of gamma radiation over the period of time from the in vivo radioactive analyte and to emit photons representative of the gamma radiation level. The light detector 21 may be disposed with respect to the scintillation material 20 to receive and convert the photons into signal data representative of the frequency level over time of gamma radiation received. The signal amplifier 33 may amplify the signal data, the measurement sensor 11 having at least one sensor output 27 for such amplified signal data. At least one computer processor 42 may be associated with a non-transient memory 40 and a clock 48, the computer processor 42 in operable communication with the non-transient memory 40 and the measurement sensor 11. The non-transient memory 40 may hold or include control computer program code 56 executable by the computer processor 42 to receive the amplified signal data in a record file format; transmit the amplified signal data to a desired storage; access reference data from a desired storage; and to apply such amplified signal data to a parametric model to compare the signal data to the reference data to determine the probability of a proper administration of the radioactive analyte to the subject. As before, the amplified signal data may be normalized, and the parametric model may be a time series function of one or more of the amplitude and slope of the amplified signal data.

Amplified signal data resulting from both proper and improper administrations of radioactive analyte would both include variability related to the total radioactivity of the radio analyte as well as the method and process used for the injection. For instance, the injection spike signal may have varying amplitude depending on the total injected activity, or the rate of increase of the amplified signal data would change based on the speed at which the radio analyte is injected.

One approach to account for for the variances caused by the above would be to normalize the amplified signal data based on the maximum amplified signal value recorded. By scaling the amplified signal data such that its scaled maximum value is, for instance, 1, then various instances of amplified signal data could be compared against each other even though their total injected activities may differ. Another method, for example, of normalizing the amplified signal data could be to scale the amplified signal data based on the otherwise measured total activity of the injected radio analyte.

With respect to the analysis or parametric model that may be done with respect to the amplified signal data in order to determine the likelihood or probability that administration of the radioactive analyte is proper (e.g., accurate and consistent with clinical protocol), the parametric model may include various algorithms for comparing the amplified signal data to reference data in order to calculate similarities or differences. As noted above, the parametric model may be a time series function of one or more of the amplitude and slope of the amplified signal data.

For the parametric model, one or more representative sets of amplified signal data may be used as references that represent administrations of radio analyte which were proper, whereas one or more other sets of amplified signal data could be used as references that represent administrations of radio analyte which were improper. In one embodiment, for example, over a given portion of the amplified signal data, a calculation may be made that would sum the number of seconds during which the amplified signal data is larger than a specified threshold value. For instance, in FIG. 24, setting a threshold value of 500 would count only the time period between 0 and 10. This desired amount of time that the amplified signal data is higher than the threshold could be compared to the same algorithm being applied to reference data. Then, the relative similarity or difference in the calculated time of threshold crossing would indicate the likelihood or probability that the amplified signal data represents a proper or improper administration of radio analyte to the subject.

Similarly, in another embodiment of parametric model, instead of calculating the time period that the amplified signal data surpasses a threshold, an integral of the amplified signal data during the threshold surpassing time period may be calculated. Then, applying this same algorithm to reference data will, similarly, indicate the likelihood that the amplified signal data represents a proper or improper administration of radio analyte.

Additionally, a parametric model comprising a polynomial could be statistically fit to the amplified signal data samples so as to provide a best fit. The same order polynomial would be fit to reference data sets as well. Then, the polynomial coefficients could be compared in order to indicate the likelihood that the amplified signal data represents a proper or improper administration of radio analyte.

Also, an artificial intelligence neural network or cluster analysis algorithm could be used as parametric models to compare the amplified signal data to sets of reference data. These algorithms would compare the amplified signal data to reference data that is known to represent proper administrations and to those that are known to represent improper administrations. The algorithms would then indicate the likelihood that the amplified signal data belongs to one of those groups.

It will be apparent to one skilled in the art that a computer system that includes suitable programming means or modules for operating in accordance with the disclosed methods also falls well within the scope of the present invention. A specially configured computer system including suitable programming means to satisfy the objects described above can be provided. Suitable programming means include any means for directing a computer system to execute the steps of the system and method of the invention, including for example, systems comprised of processing units and arithmetic-logic circuits coupled to computer memory, which systems have the capability of storing in computer memory, which computer memory includes electronic circuits configured to store data and program instructions, with programmed steps of the method of the invention for execution by a processing unit. Aspects of the present invention may be embodied in a computer program product, such as a non-transient recording medium, for use with any suitable data processing system. The present system can further run on a variety of platforms, including any of a variety of software operating systems. Appropriate hardware, software and programming for carrying out computer instructions between the different elements and components of the present invention are provided.

The invention may be embodied in other specific forms without departing from the spirit or essential characteristics thereof The present embodiments are therefore to be considered in all respects as illustrative and not restrictive, the scope of the invention being indicated by the claims of the application rather than by the foregoing description, and all changes which come within the meaning and range of equivalency of the claims are therefore intended to be embraced therein.

What is claimed is:

1. A system for the ex vivo real-time detection of gamma radiation emitted by a subject from administration and uptake over a period of time of a radioactive analyte that decays in vivo by positron emission, the system comprising:
at least one ex vivo measurement sensor having a sensor housing, a scintillation material, a light detector, a temperature sensor, a signal amplifier, and a sensor power source,
the light detector, temperature sensor, signal amplifier, and sensor power source in operable communication,
the scintillation material and light detector disposed within the sensor housing in a light proof manner, with the scintillation material adapted to receive a level of gamma radiation over the period of time from the in vivo radioactive analyte and to emit photons representative of the gamma radiation level,
the light detector disposed with respect to the scintillation material to receive and convert the photons into signal data representative of the frequency level over time of gamma radiation received,
the signal amplifier adapted to amplify the signal data, the measurement sensor having at least one sensor output for such amplified signal data;
at least one computer processor having a non-transient memory and a clock, the computer processor in operable communication with the measurement sensor;
wherein the memory includes control computer program code executable by the at least one computer processor, the control computer program code including a first module for measurement, a second module for data management;
wherein the first module is adapted to receive the signal data in a record file format;
a temperature compensator coupled with the temperature sensor, the temperature sensor adapted to measure an ambient temperature with the system adapted to communicate the ambient temperature to the temperature compensator, such that the temperature compensator is adapted to generate a temperature correction factor based on comparison of the ambient temperature to a reference temperature, the temperature compensator further adapted to apply the temperature correction factor to the signal data to produce temperature compensated signal data;
wherein the second module is adapted to receive the signal data of a record file from the first module and to transmit the compensated signal data to a desired storage; and
wherein the computer program code further comprises a third module adapted to receive stored data of a record file from the second module, to apply such stored data to calculate changes in the compensated signal data over a desired period, to apply stored data to a predictive model to generate predictive data values over a desired period for such record file as a predictive outcome, and to transmit such changes to a desired storage.

2. The ex vivo measurement sensor of claim 1, further comprising a radiation shielding mask for gamma radiation.

3. The ex vivo measurement sensor of claim 2, wherein the shielding mask defines an aperture in the form of a collimator for gamma radiation incident into the scintillation material.

4. The ex vivo measurement sensor of claim 2, further comprising an alignment feature for removable alignment of the measurement sensor with respect to the subject.

5. The ex vivo measurement sensor of claim 4, wherein the alignment feature comprises a light emitter disposed within the sensor so as permit alignment of the collimator aperture to a desired portion of the subject by illumination of the subject.

6. The ex vivo measurement sensor of claim 5, wherein the light emitter is a light emitting diode disposed within the aperture, the ex vivo measurement sensor further comprising light proof sealant about the light emitting diode to prevent the output of the diode or ambient light to strike the scintillation material, while permitting the scintillation material to receive incident gamma radiation.

7. The system of claim 1, wherein the ex vivo measurement sensor further comprises a radiation shielding mask for gamma radiation, the shielding mask defining an aperture in the form of a collimator for gamma radiation incident into the scintillation material; and the system further comprising a stand alignment feature for the removable mounting of the ex vivo measurement sensor in a configuration relative to the subject so as to permit alignment of the collimator aperture to a desired portion of the subject.

8. The system of claim 1, further comprising a filter for filtering the amplified signal data based on amplitude.

9. The system of claim. 8, wherein the filter comprises a voltage comparator.

10. The system of claim 8, wherein the filter further comprises an analog to digital converter and control computer program code adapted to compare digital amplified signal data to a reference level.

11. A device for the detection of radiation, the device comprising:
a measurement sensor having a housing, a scintillation material, a light detector, a light shield, a temperature sensor, a signal amplifier, a sensor processor, a non-transient sensor memory, and a sensor power supply,
the light detector, signal amplifier, sensor processor, sensor memory, and sensor power supply in operable communication by a printed circuit board assembly, the printed circuit board assembly having a board defining a plane having a first surface and an opposing second surface, the light shield adapted for mounting onto the first surface of the board and shielding the scintillation material and light detector from ambient light;
wherein the scintillation material has first width parallel with the plane and the light detector has a second width parallel with the plane;
the light shield defines a first cavity with a third width equal or greater than the first width such that the first cavity is adapted to receive the scintillation material and the light shield defines a second cavity with a fourth width equal or greater than the second width such that the second cavity is adapted to receive the light detector; and
the scintillation material and light detector disposed within the light shield with the scintillation material adapted to receive a level of gamma radiation and to emit photons representative of the gamma radiation level, the light detector disposed with respect to the scintillation material so as to be adapted to receive and convert the multiplied photons into signal data representative of the level of radiation received,
wherein the first and second cavities are in communication and in such proximal relation that the light shield optically aligns the scintillation material to the light detector when the scintillation material is received by the first cavity and the light detector is received by the second cavity, and operably engaged with the printed circuit board assembly; and
the signal amplifier adapted to amplify the signal data, the sensor memory including a measurement sensor identifier, the measurement sensor having at least one sensor output port for such amplified signal data.

12. The device of claim 11,
wherein the light shield is mounted to the first surface of the board with solder; and
wherein the light shield is selected from a group consisting of metal: copper, brass, bronze, steel, aluminum, nickel-silver, beryllium copper, silver, gold, and nickel.

13. A system for the ex vivo real-time detection of gamma radiation emitted at an area of interest by a subject from administration and uptake over a period of time of a radioactive analyte that decays in vivo by positron emission, the system comprising:
a primary ex vivo measurement sensor having a sensor housing with a radiation shield, the sensor housing with the radiation shield defining a cavity, the radiation shield further defining an aperture into the cavity, a collimator disposed within the aperture so as to admit a collimated gamma radiation into the cavity from the area of interest, a scintillation material disposed within the cavity such that the collimated gamma radiation is incident on the scintillation material, a light detector disposed within the sensor housing to detect light emitted from the scintillation material, a temperature sensor, a signal amplifier, and a sensor power source, the light detector, temperature sensor, signal amplifier, and sensor power source in operable communication,
the scintillation material and light detector disposed within the sensor housing with the scintillation material adapted to receive a level of gamma radiation over the period of time from the in vivo radioactive analyte and to emit photons representative of the gamma radiation level, the light detector disposed with respect to the scintillation material so as to receive and convert the multiplied photons into signal data representative of the frequency level over time of gamma radiation received,
the signal amplifier adapted to amplify the signal data, the measurement sensor having at least one sensor output for such amplified signal data;
a secondary ex vivo measurement sensor that is unshielded for measuring background gamma radiation;
a collimator alignment system in operable engagement with the sensor housing for aligning the collimator to the area of interest;
at least one computer processor having a non-transient memory and a clock, the computer processor in operable communication with the primary and secondary measurement sensors;
wherein the memory includes control computer program code executable by the at least one computer processor, the control computer program code including a first module for measurement, a second module for data management;

wherein the first module is adapted to receive the signal data in a record file format;

a temperature compensator coupled with the temperature sensor, the temperature sensor adapted to measure an ambient temperature with the system adapted to communicate the ambient temperature to the temperature compensator, such that the temperature compensator generates a temperature correction factor based on comparison of the ambient temperature to a reference temperature, the temperature compensator further adapted to apply the temperature correction factor to the signal data to produce temperature compensated signal data;

wherein the second module is adapted to receive the signal data of a record file front the first module and to transmit the compensated signal data to a desired storage; and wherein the computer program code further comprises third and fourth modules, the third module adapted to receive stored data of a record file from the second module, (i) to apply such stored data to a predictive model to generate predictive data values over a desired period for such record file as a predictive outcome, and to transmit such predictive outcome to a desired storage; and (ii) to apply such stored data to calculate changes in the compensated signal data over a desired period, and to transmit such changes to a desired storage and the fourth module adapted to subtract signal data from the secondary ex vivo measurement sensor from signal data from the primary ex vivo measurement sensor.

14. The system of claim 13, wherein the primary ex vivo measurement sensor further comprises a radiation shielding mask for gamma radiation.

15. The system of claim 14, wherein the primary ex vivo measurement sensor shielding mask defines an aperture in the form of a collimator for gamma radiation incident into the scintillation material.

16. The system of claim 14, wherein the primary ex vivo measurement sensor further comprises an alignment feature for removable alignment of the primary ex vivo measurement sensor with respect to the subject.

17. The system of claim 16, wherein the primary ex vivo measurement sensor alignment feature comprises a light emitter disposed within the sensor so as permit alignment of the collimator aperture to a desired portion of the subject by illumination of the subject.

18. The system of claim 17, wherein the primary ex vivo measurement sensor light emitter is a light emitting diode disposed within the aperture, the ex vivo measurement sensor further comprising light proof sealant about the light emitting diode to prevent the output of the diode or ambient tight to strike the scintillation material, while permitting the scintillation material to receive incident gamma radiation.

19. The system of claim 13, wherein the primary ex vivo measurement sensor further comprises a radiation shielding mask for gamma radiation, the shielding mask defining an aperture in the form of a collimator for gamma radiation incident into the scintillation material; and the system further comprising a stand alignment feature for the removable mounting of the ex vivo measurement sensor in a configuration relative to the subject so as to permit alignment of the collimator aperture to a desired portion of the subject.

20. The system of claim 16, further comprising a filter for filtering the amplified signal data based on amplitude.

21. The system of claim 20, wherein the filter comprises a voltage comparator.

22. The system of claim 20, wherein the filter further comprises an analog to digital converter and control computer program code adapted to compare digital amplified signal data to a reference level.

* * * * *